(12) United States Patent
Yusibov et al.

(10) Patent No.: US 8,124,103 B2
(45) Date of Patent: *Feb. 28, 2012

(54) INFLUENZA ANTIGENS, VACCINE COMPOSITIONS, AND RELATED METHODS

(75) Inventors: Vidadi Yusibov, Havertown, PA (US); Vadim Mett, Newark, DE (US); Konstantin Musiychuck, Swarthmore, PA (US)

(73) Assignee: Fraunhofer USA, Inc, Plymouth, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/706,573

(22) Filed: Feb. 13, 2007

(65) Prior Publication Data

US 2007/0275014 A1 Nov. 29, 2007

Related U.S. Application Data

(60) Provisional application No. 60/773,378, filed on Feb. 13, 2006, provisional application No. 60/813,955, filed on Jun. 15, 2006.

(51) Int. Cl.
| A61K 39/145 | (2006.01) |
| A61K 39/12 | (2006.01) |
| A61K 39/295 | (2006.01) |
| A61K 39/00 | (2006.01) |
| C12P 21/04 | (2006.01) |
| C07H 21/04 | (2006.01) |

(52) U.S. Cl. ............... 424/210.1; 424/185.1; 424/192.1; 424/204.1; 424/201.1; 435/69.7; 536/23.4; 536/23.72

(58) Field of Classification Search ......................... None
See application file for complete search history.

(56) References Cited

U.S. PATENT DOCUMENTS

| 4,196,265 A | 4/1980 | Koprowski et al. |
| 4,270,537 A | 6/1981 | Romaine |
| 4,596,556 A | 6/1986 | Morrow et al. |
| 4,653,728 A | 3/1987 | Mochizuki et al. |
| 4,790,824 A | 12/1988 | Morrow et al. |
| 4,816,567 A | 3/1989 | Cabilly et al. |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brenneman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,693,493 A | 12/1997 | Robinson et al. |
| 5,693,761 A | 12/1997 | Queen et al. |
| 5,693,762 A | 12/1997 | Queen et al. |

(Continued)

FOREIGN PATENT DOCUMENTS

| EP | 404097 | 6/1990 |
| WO | WO9311161 | 6/1993 |
| WO | WO9602555 | 2/1996 |
| WO | WO9713537 | 4/1997 |
| WO | WO9737705 | 10/1997 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |

(Continued)

OTHER PUBLICATIONS

The World Health Organization Global Influenza Program Surveillance Network, Evolution of H5N1 Avian Influenza Viruses in Asia, 2005, Emerging Infectious Diseases, vol. 11, No. 10, pp. 1515-1521.*

(Continued)

Primary Examiner — Benjamin P Blumel
(74) Attorney, Agent, or Firm — Fish & Richardson P.C.

(57) ABSTRACT

The present invention relates to the intersection of the fields of immunology and protein engineering, and particularly to antigens and vaccines useful in prevention of infection by influenza virus. Provided are recombinant protein antigens, compositions, and methods for the production and use of such antigens and vaccine compositions.

25 Claims, 18 Drawing Sheets

U.S. PATENT DOCUMENTS

Figure 1:
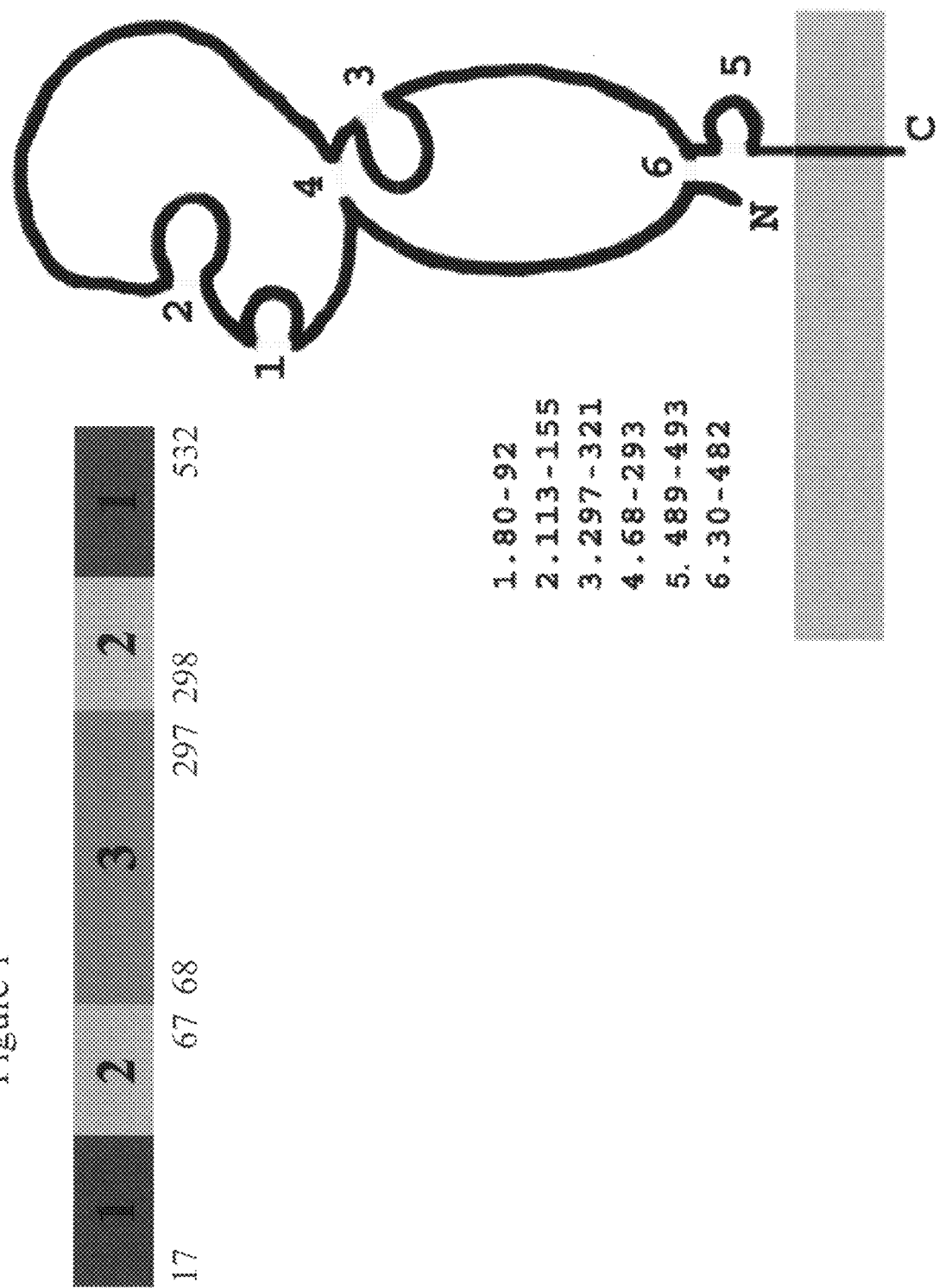

| | | | |
|---|---|---|---|
| 5,698,417 | A | 12/1997 | Robinson et al. |
| 5,698,426 | A | 12/1997 | Huse |
| 5,702,892 | A | 12/1997 | Mulligan-Kehoe |
| 5,704,911 | A | 1/1998 | Parsons |
| 5,705,154 | A | 1/1998 | Dalie et al. |
| 5,733,743 | A | 3/1998 | Johnson et al. |
| 5,750,078 | A | 5/1998 | Shitara et al. |
| 5,759,817 | A | 6/1998 | Barbas |
| 5,770,403 | A | 6/1998 | Dalie et al. |
| 5,770,429 | A | 6/1998 | Lonberg et al. |
| 5,855,866 | A | 1/1999 | Thorpe et al. |
| 5,877,289 | A | 3/1999 | Thorpe et al. |
| 5,888,789 | A | 3/1999 | Rodriguez et al. |
| 5,893,397 | A | 4/1999 | Peterson et al. |
| 5,965,132 | A | 10/1999 | Thorpe et al. |
| 5,993,412 | A | 11/1999 | Deily et al. |
| 6,042,832 | A | 3/2000 | Koprowski et al. |
| 6,044,555 | A | 4/2000 | Jacob et al. |
| 6,093,399 | A | 7/2000 | Thorpe et al. |
| 6,261,535 | B1 | 7/2001 | Thorpe et al. |
| 6,524,825 | B1 | 2/2003 | Mizzen et al. |
| 6,649,172 | B2 * | 11/2003 | Johnson ............... 424/278.1 |
| 6,740,740 | B2 | 5/2004 | Garger et al. |
| 6,797,491 | B2 | 9/2004 | Neefe, Jr. et al. |
| 6,841,659 | B2 | 1/2005 | Turpen et al. |
| 7,888,135 | B2 | 2/2011 | Tarleton et al. |
| 2004/0093643 | A1 | 5/2004 | Ensle |
| 2004/0170606 | A1 | 9/2004 | Palmer et al. |
| 2004/0268442 | A1 | 12/2004 | Miller et al. |
| 2005/0026291 | A1 | 2/2005 | Fedorkin et al. |
| 2005/0042229 | A1 | 2/2005 | Yang et al. |
| 2005/0048074 | A1 * | 3/2005 | Cardineau et al. ......... 424/186.1 |
| 2005/0186621 | A1 * | 8/2005 | Galarza et al. .................. 435/6 |
| 2006/0008473 | A1 * | 1/2006 | Yang et al. ............... 424/204.1 |
| 2006/0265787 | A1 * | 11/2006 | Piruzian et al. ............... 800/288 |
| 2008/0124272 | A1 | 5/2008 | Yusibov et al. |
| 2008/0279877 | A1 | 11/2008 | Yusibov et al. |
| 2009/0324634 | A1 | 12/2009 | Knapp et al. |
| 2010/0227373 | A1 | 9/2010 | Yusibov et al. |
| 2011/0027304 | A1 | 2/2011 | Yusibov et al. |
| 2011/0059130 | A1 | 3/2011 | Yusibov |

FOREIGN PATENT DOCUMENTS

| | | | |
|---|---|---|---|
| WO | WO03040179 | | 5/2003 |
| WO | WO2004043886 | | 5/2004 |
| WO | WO 2005/026375 | * | 3/2005 |
| WO | WO2005049839 | | 6/2005 |
| WO | WO2005067620 | | 7/2005 |
| WO | WO2005081905 | | 9/2005 |
| WO | WO2006003018 | | 1/2006 |
| WO | WO2006124712 | | 11/2006 |
| WO | WO2007089753 | | 8/2007 |
| WO | WO2007095304 | | 8/2007 |
| WO | WO2007095318 | | 8/2007 |
| WO | WO2007149715 | | 12/2007 |
| WO | WO2008021959 | | 2/2008 |
| WO | WO2008033105 | | 3/2008 |
| WO | WO2008033159 | | 3/2008 |
| WO | WO2008048945 | | 4/2008 |
| WO | WO2008110937 | | 9/2008 |
| WO | WO2008134643 | | 11/2008 |
| WO | WO2009/009759 | | 1/2009 |
| WO | WO2009026397 | | 2/2009 |
| WO | WO2009054708 | | 4/2009 |
| WO | WO2009058355 | | 5/2009 |
| WO | WO2010036970 | | 4/2010 |
| WO | WO2010037046 | | 4/2010 |

OTHER PUBLICATIONS

Nagy et al., Thermal stability of chemically denatured green fluorescent protein (GFP)—A preliminary study, 2004, Thermochimica Acta, vol. 410, No. 1, abstract.*

Piruzian et al., A reporter system for prokaryotic eukaryotic cells based on the thermostable lichenase from *Clostridium thermocellum*, 2002, Molecular and General Genetics, vol. 266, pp. 778-786.*

Piruzian et al., The use of a thermostable b-glucanase gene from *Clostridium thermocellum* as a reporter gene in plants, 1998, Molecular and General Gentics, vol. 257, pp. 561-567.*

Alvarez et al., "Plant-made subunit vaccine against pneumonic and bubonic plague is orally immunogenic in mice", *Vaccine*, Elsevier, Ltd., GB, vol. 24, No. 14, Jan. 13, 2006, pp. 2477-2490.

Barfield et al., "Gene Transfer in Plants of *Brassica juncea* Using *Agrobacterium tumefaciens* Mediated Transformation", *Plant Cell Reports* 1991, 10(6/7): 308-14.

Bates, "Genetic Transformation of Plants by Protoplast Electroporation", *Molecular Biotechnol.*, 1994, 2(2):135-145.

Beachy et al., "A Genetic Map for the Cowpea Strain of TMV" *Virology* 1976, 73: 498-507.

Bedell et al., "The E6-E7 Region of Human Papillomavirus Type 18 is Sufficient for Transformation of NIH 3T3 and Rat-1 Cells", *J. Virol.*, 1987, 61:3635-40.

Bisaro et al., "Genetic Analysis of Tomato Golden Mosaic Virsu", *Current Communications in Molecular Biology: Viral Vectors*, Cold Spring Harbor Laboratory, Cold Spring Harbor, NY, pp. 172-189, 1988.

Bol et al., "A Functional Equivalence of Top Component a RNA and Coat Protein in the Initiation of Infection by Alfalfa Mosaic Virus" *Virology* 1971, 46: 73-85.

Bol et al., "Alfalfa Mosaic Virus and Ilarviruses: Involvement of Coat Protein in Multiple Steps of the Replication Cycle" *J., Gen. Virol.* 1999, 80: 1089-1102.

Boyd, M. R. and Beeson, M. F., "Animal models for evaluation of compounds against influenza viruses", *Journal of Antimicrobial Chemotherapy*, (1975) 1 (*Suppl.*), 43-47.

Brett et al., "Immunization against influenza A virus: comparison of conventional inactivated, live-attenuated and recombinant baculovirus produced purified hemagglutinin and neuraminidase vaccines in a murine model system", *Virology*, vol. 339, No. 2, Sep. 1, 2005, pp. 273-280.

Bruening et al., "In Vitro and In Vivo Translation of the Ribonucleic Acids of a Cowpea Strain of Tobacco Mosaic Virus" *Virology* 1976, 71: 498-517.

Buscaglia et al., "Tandem amino acid repeats from *Trypanosoma cruzi* shed antigens increase the half-life of proteins in blood", *Blood*, vol. 93(6), pp. 2025-2032, Mar. 15, 1999.

Canizares et al., "Use of viral vectors for vaccine production in plants", *Immunol. Cell Biol.*, 2005, 83:263-270.

Chen et al., "Complete sequence of the binary vector pBI121 and its application in cloning T-DNA insertion from transgenic plants", *Mol. Breed.*, 2003, 11, 287-293.

Chen et al., "Induction and relief of nasal congestion in ferrets infected with influenza virus", *Int. J. Exp. Path.*, (1995), 76, pp. 55-64.

Corbel, M. J., "Reasons for instability of bacterial vaccines", *Developments in Biological Standardization*, vol. 87, pp. 113-124, 1996.

Costa et al., "Conformational stability and antibody response to the 18kDa heat-shock protein formulated into different vehicles", *Applied Biochemistry and Biotechnology*, vol. 73(1), pp. 19-28, Apr. 1998.

Crossway, A., et al., "Integration of foreign DNA following microinjection of tobacco mesophyll protoplasts"*Mol. Gen. Genet.*, 1986, 202:179-185.

Curtis and Nam, "Transgenic radish (*Raphanus sativus* L. *longipinnatus* Bailey) by floral-dip method—plant development and surfactant are important in optimizing transformation efficiency", *Transgenic Research*, 2001, 10(4):363-371.

DeGraff, et al., "In Vitro Evidence That the Coat Protein of Alfalfa Mosaic Virus Plays A Direct Role in The Regulation of Plus and Minus RNA Synthesis Implications for the Life Cycle of Alfalfa Mosaic Virus" *Virology* 1995, 208: 583-589.

Desfeux et al., "Female Reproductive Tissues Are the Primary Target of *Agrobacterium*-Mediated Transformation by the Arabidopsis Floral-Dip Method", *Plant Physiology*, 2000, 123(3):895-904.

Dréau et al., "Human Papilloma Virus in Melanoma Biopsy Specimens and Its Relation to Melanoma Progression", *Annals of Surgery*, 2000, 231:664-671.

Fenton et al., "Immunity to Influenza in Ferrets. XIV: Comparative Immunity Following Infection or Immunization With Live or Inactivated Vaccine", *Br. J. exp. Path.,* (1981) 62, 297.

Fernando et al., "Expression, purification and immunological characterization of the transforming protein E7, from cervical cancer-associated human papillomavirus type 16", *Clin Exp Immunol,* 1999, 115:397-403.

Flick-Smith et al., "A Recombinant Carboxy-Terminal Domain of the Protective Antigen of *Bacillus anthracia* Protects Mice against Anthrax Infection", *Infect. Immun.,* 2002, 70:1653-1656.

Fraley et al., "Liposome-Mediated Delivery of Tobacco Mosaic Virus RNA Into Tobacco Protoplasts: A Sensitive Assay for Monitoring Liposome-Protoplast Interactions" *Proc. Natl. Acad. Sci. USA* 1982, 79: 1859-1863.

Fraley et al., "Expression of Bacterial Genes in Plant Cells" *Proc. Natl. Acad. Sci. USA* 1983, 80: 4803-4807.

Franconi et al., "Plant-derived Human Papillomavirus 16 E7 Oncoprotein Induces Immune Response and Specific Tumor Production", *Cancer Res.,* 2002, 62:3654.

Fromm et al., "Expression of Genes Transferred Into Monocot and Dicot Plant Cells by Electroporation" *Proc. Natl. Acad. Sci. USA* 1985, 82: 5824, 1985.

Gelvin, "*Agrobacterium*-Mediated Plant Transformation: the Biology behind the 'Gene-Jockeying' Tool", *Microbiol. Mol Biol. Rev.,* 2003, 67(1):16-37.

Giri and Narasu, "Transgenic hairy roots: recent trends and applications", *Biotechnol. Adv.,* 2000, 18:1-22.

Gleba et al., "Magnifection—a new platform for expressing recombinant vaccines in plants", *Vaccine,* 2005, 23:2042-2048.

Goldenkova et al., "A Thermostable *Clostridium thermocellum* Lichenase-based Reporter System for Studying the Gene Expression Regulation in Prokaryotic and Eukaryotic Cells", *Mol. Biol.,* 2002, 36:698-704.

Green et al., "Transient protein expression in three Pisum sativum (green pea) varieties", *Biotechnology Journal,* vol. 4, No. 2, Feb. 2009, pp. 230-237.

Grierson et al., "Plant Viruses", *Plant Molecular Biology,* Blackie, London, pp. 126-146, 1984.

Gu et al., "Protection against anthrax toxin by vaccination with a DNA plasmid encoding anthrax protective antigen", *Vaccine,* 1999, 17:340.

Hahn et al., "Native-like in-vivo folding of a circularly permuted jellyroll protein shown by crystal structure analysis", *Proc. Natl. Acad. Sci., USA,* 1994, 91(22):10417-10421.

Hellens et al., "pGreen: a versatile and flexible binary Ti vector for *Agrobacterium*-mediated plant transformation" *Plant Molecular Biology 2000,* 42: 819-832.

Hobson et al., "The role of serum haemagglutination-inhibiting antibody in protection against challenge infection with influenza A2 and B viruses", *J. Hyg.,* 1972, 70:767.

Huang et al., "Plant-derived measles virus hemagglutinin protein induces neutralizing antibodies in mice", *Vaccine,* Feb. 28, 2001, vol. 19, No. 15-16, pp. 2163-2171.

Hull et al., "Human-derived, plant-produced monoclonal antibody for the treatment of anthrax", *Vaccine,* 2005, 23:2082-2086.

Hunter et al., "Messenger RNA for the Coat Protein of Tobacco Mosaic Virus" *Nature* 1976, 260: 759-760.

Ishikawa et al., "In Vitro Mutagenesis of the Putative Replicase Genes of Tobacco Mosaic Virus" *Nucleic Acids Res.* 1986, 14: 8291-8308.

Jaspars et al., "Plant Viruses With a Multipartite Genome" *Adv. Virus Res.* 1974, 19: 37-149.

Kao et al., "A Method for High-frequency Intergeneric Fusion of Plant Protoplasts", *Planta,* 1974, 115:355.

Kapila et al., "An *Agrobacterium*-mediated transient gene expression system for intact leaves", *Plant Sci.,* 1997, 122:101-108.

Kapusta et al., "A plant-derived edible vaccine against hepatitis B virus", *FASEB J.,* 1999, 13:1796-1799.

Kikkert et al., "Biological Projectiles (Phage, Yeast, Bacteria) for Genetic Transformation of Plants", *In Vitro Cell. Dev. Bio.—Plant,* 1999. 35(1):43-50.

Klein et al., "High-velocity microprojectiles for delivering nucleic acids into living cells", *Nature,* 1987, 327:70-73.

Knudsen and Muller, "Transformation of the developing barley endosperm by particle bombardment", *Planta,* 1991, 185:330-336.

Krens et al., "In vitro transformation of plant protoplasts with Ti-plasmid DNA", *Nature,* 1982, 296:72-74.

Kumagai, et al., "Rapid, High-Level Expression of Glycosylated Rice α-Amylase in Transfected Plants by an RNA Viral Vector" *Gene* 2000, 245: 169-174.

Lambkin et al., "Strong local and systemic protective immunity induced in the ferret model by an intranasal virosome-formulated influenza subunit vaccine", *Vaccine,* 2004, 22:4390.

Lawton et al., "Expression of a Soybean (3-Conclycinin Gene Under the Control of the Cauliflower Mosaic Virus Virus 35S and 19S Promoters in Transformed Petunia Tissues" *Plant Mol. Biol* 1987, 9: 315-324.

Leite et al., "Expression of correctly processed human growth hormone in seeds of transgenic tobacco plants", *Molecular Breeding,* 2000, 6: 47-53.

Lim et al., "An Anthrax Lethal Factor-Neutralizing Monoclonal Antibody Protects Rats before and after Challenge with Anthrax Toxin", *Infection and Immunity,* 2005, 73:6547.

Lin et al., "Treatment of Established Tumors with a Novel Vaccine That Enhances Major Histocompatibility Class II Presentation of Tumor Antigen", *Cancer Research,* 1996, 56:21.

Little et al., "Passive Protection by Polyclonal Antibodies against *Bacillus anthracia* Infection in Guinea Pigs", *Infect. Immun.,* 1997, 65:5171-5175.

Loesch-Fries, et al., "Expression of Alfalfa Mosaic Virus RNA 4 cDNA Transcripts In Vitro and In Vivo" *Virology* 1985, 146: 177-187.

Maliga et al., "Transient Cycloheximide Resistance in a Tobacco Cell Line", *Mol. Gen. Genet.,* 1976, 149, 267-271.

Maassab et al., "Evaluation of a Cold-Recombinant Invluenza Virus Vaccine in Ferrets", *The Journal of Infectious Diseases,* vol. 146, No. 6, Dec. 1982, pp. 780-790.

McCormick et al., "Rapid Production of Specific Vaccines for Lymphoma by Expression of the Tumor-Derived Single-Chain Fv Epitopes in Tobacco Plants" *Proc. Natl. Acad. Sci. USA* 1999, 96: 703-708.

McHugh et al., "Improved stability of a protein vaccine through elimination of a partially unfolded state", *Protein Science,* 2004, vol. 13, pp. 2736-2743.

Mellin et al., "Human Papillomavirus (HPV) DNA in Tonsillar Cancer: Clinical Correlates, Rise of Relapse, and Survival", *International Journal of Cancer,* 2000, 89:300-304.

Menczel et al. "Streptomycin Resistant and Sensitive Somatic Hybrids of *Nicotiana tabacum* + *Nicotiana knightiana*: Correlation of Resistance to *N. tabacum* Plastids", *Theor. Appl. Genet.,* 1981, 59, 191-195.

Meshi et al., "Function of the 30 kd Protein of Tobacco Mosaic Virus: Involvement in Cell-To-Cell Movement and Dispensability for Replication" *EMBO J.* 1987, 6: 2557-63.

Mett et al., "A plant-produced influenza subunit vaccine protects ferrets against virus challenge", *Influenza and Other Respiratory Viruses,* Blackwell Publishing Ltd., UK, vol. 2, No. 1, Jan. 1, 2008, pp. 33-40.

Modelska et al., "Immunization against rabies with plant-derived antigen", *Proc. Nati. Acad. Sci., USA,* 1998, 95:2481-2485.

Murashige and Skoog, "A Revised Medium for Rapid Growth and Bio Assays with Tobacco Tissue Cultures", *Physiologia Plantarum,* 1962, 15:473.

Musiychuk et al., "A launch vector for the production of vaccine antigens in plants", *Influenza and Other Respiratory Viruses,* 2007, 1:1.

Musiychuk et al., "Preparation and properties of *Clostridium thermocellum* lichenase deletion variants and their use for construction of bifunctional hybrid proteins", *Biochemistry(MOSC),* vol. 65(12), pp. 1397-1402, Dec. 2000.

Nass, "Anthrax Vaccine—Model of a Response to the Biologic Warfare Threat", *Infect. Dis. Clin. North Am.,* 1999, 13,187-208.

NCBI GenBank Accession No. ABP96852, "Influenza A virus" (A/Egypt/2616-NAMRU3/2007(H5N1)) hemagglutinin (HA) gene, complete CDS, 30, Apr. 2007

NCBI GenBank Accession No. AAS93885, "Influenza A virus" (A/Cheju/274/2002(H3N2)) neuraminidase (NA) gene, complete CDS, 25, Apr. 2004.

Neeleman et al., "Role of Alfalfa Mosaic Virus Coat Protein Gene in Symptom Formation" *Virology* 1991, 181: 687-693.

Neeleman et al., "Infection of Tobacco With Alfalfa Mosaic Virus cDNAs Sheds Light on the Early Function of the Coat Protein" *Virology* 1993, 196: 883-887.

Park et al., "Molecular Biology of Cervical Cancer and Its Precursors", *Cancer*, 1995, 76:1902-1913.

Peres et al., 2001 , "Shoot regeneration capacity from roots and transgenic hairy roots of tomato cultivars and wild related species", *Plant Cell, Tissue, and Organ Culture*, 2001, 65:37-44.

Petosa et al., "Crystal structure of the anthrax toxin protective antigen", *Nature*, 1997, 385:833-838.

Pilon-Smits et al., "Overexpression of ATP Sulfurylase in Indian Mustard Leads to Increased Selenate Uptake, Reduction, and Tolerance" *Plant Physiol.* 1999, 119(1): 123-132.

Potter et al., "Immunity to Influenza in Ferrets II. Influence of Adjuvants on Immunization", *Br. J. Exp. Pathol.,* 1972, 53:168.

Potter et al., "Immunity to Influenza in Ferrets VI. Immunization with Adjuvanted Vaccines", *Arch. Gesamte Virusforsch.*, 1973, 42:285.

Potter et al., "Immunity to influenza in ferrets V. Immunization with inactivated virus in adjuvant 65", *J. Hyg. Lond.*, 1973, 71:97.

Qing et al., "Transformation of Pakchoi (*Brassica rapa* L. ssp. *chinensis*) by *Agrobacterium* Infiltration", *Molecular Breeding*, 2000, 1:67-72.

Rao and Ravishankar, "Plant cell cultures: Chemical factories of secondary metabolites", *Biotechnol. Adv.*, 2002, 20:101-153.

Reinstein et al., Degradation of the E7 human papillomavirus oncoprotein by the ubiquitin-proteasome system: targeting via ubiquitination of the N-terminal residue, *Oncogene*, 2000, 19, 5944-5950.

Riva et al., "*Agrobacterium tumefaciens*: a natural tool for plant transformation", *EJB Electronic J. Biotech.*, 1998, 1(3), 118-133.

Saito, et al., "Long-Distance Movement and Viral Assembly of Tobacco Mosaic Virus Mutants" *Virology* 1990, 176: 329-336.

Scheiblauer et al., "Pathogenicity of influenza A/Seal/Mass/1/80 virus mutants for mammalian species", *Arch Virol*, (1995), 140: 341-384.
Schell et al., "Transgenic Plants As Tools to Study the Molecular Organization of Plant Genes." *Science* 1987, 237: 1176-1183.
Seedorf et al., "Human Papillomavirus Type 16 DNA Sequence", *Virology,* 1985, 145:181.
Shivprasad et al., "Heterologous Sequences Greatly Affect Foreign Gene Expression in Tobacco Mosaic Virus-Based Vectors", *Virology,* 1999, 255(2):312-23.
Singh et al., "Gln277 and Phe544 residues are involved in thermal inactivation of protective antigen of *Bacillus anthracis", Biochemical and Biophysical Research Communications,* 2002, vol. 296, pp. 1058-1062.
Singh et al., "Study of Immunization against Anthrax with the Purified Recombinant Protective Antigen of *Bacillus anthracis*", *Infect. Immun.*, 1998, 66, 3447-3448.
Singh et al., "Thermal inactivation of protective antigen of *Bacillus anthracis* and its prevention by polyol osmolytes", *Biochemical and Biophysical Research Communications,* 2004, vol. 322, pp. 1029-1037.
Soini et al., "Presence of human papillomavirus DNA and abnormal p53 protein accumulation in lung carcinoma", *Thorax,* 1996, 51:887-893.
Spilliaert et al., "Cloning and sequencing of a Rhodothermus marinus gene, bg1A, coding for a thermostable beta-glucanase and its expression in *Escherichia coli", Eur. J. Biochem.*, vol. 224(3):923-930, Sep. 15, 1994.
Tacket et al., "Human Immune Responses to a Novel Norwalk Virus Vaccine Delivered in Transgenic Potatoes", *J. Infect. Dis.*, 2000, 182:302-305.
Thanavala et al., "Immunogenicity in humans of an edible vaccine for hepatitis B", *Proc. Natl. Acad. Sci., USA,* 2005, 102:3378-3382.
Thomas et al., "HPV-18 E6 mediated inhibition of p53 DNA binding activity is independent of E6 induced degradation", *Oncogene,* 1995, 10:261-8.
Toms et al., "Behaviour in Ferrets of Swine Influenza Virus Isolated from Man", *The Lancet,* Jan. 8, 1977, pp. 68-71.
Turpen et al., "Transfection of whole plants from wounds inoculated with *Agrobacterium tumefaciens* containing cDNA of tobacco mosaic virus", *J. Virol, Methods,* 1993, 42:227.
Van Der Kuyl et al., "Complementation and Recombination between Alfalfa Mosaic Virus RNA3 Mutants in Tobacco Plants", *Virology,* 1991, 183:731-738.
Van Der Kuyl et al., "Role of Alfalfa Mosaic Virus Coat Protein in Regulation of the Balance between Viral Plus and Minus Strand RNA Synthesis" *Virology,* 1991, 185:496-499.
Van Der Vossen, et al., "Early and Late Functions of Alfalfa Mosaic Virus Coat Protein Can Be Mutated Separately" *Virology* 1994, 202: 891-903.
Verch et al., "Expression and assembly of a full-length monoclonal antibody in plants using a plant virus vector", *J. Immunol. Methods,* 1998, 220, 69-75.
Volten-Doting, Plant Viruses Online (http://image.fs.uidaho.edu/vide/descr009.htm) (downloaded May 18, 2002) (11 pgs.).
Wagner et al., "Plant virus expression systems for transient production of recombinant allergens in *Nicotiana benthamiana", Methods: A Companion to Methods in Enzymology,* vol. 32, No. 3, Mar. 1, 2004; pp. 228-232.
Webster et al., "Measles virus hemagglutinin protein expressed in transgenic lettuce induces neutralizing antibodies in mice following mucosal vaccination", *Vaccine,* Apr. 24, 2006, vol. 24, No. 17, pp. 3538-3544.
Webster et al., "Protection of ferrets against influenza challenge with a DNA vaccine to the haemagglutinin", *Vaccine,* (1994), vol. 12, No. 16, pp. 1495-1498.
Wilson et al., "Structure of the haemagglutinin membrane glycoprotein of influenza virus at 3 Å resolution", *Nature,* 1981, 289:366.
Yusibov et al., "Antigens Produced in Plants by Infection With Chimeric Plant Viruses Immunize Against Rabies Virus and HIV-1" *Proc. Natl. Acad. Sci. USA* 1997, 94: 5784-5788.
Yusibov et al., "N-Terminal Basic Amino Acids of Alfalfa Mosaic Virus Coat Protein Involved In The Initiation of Infection" *Virology* 1995, 208: 405-407.
Yusibov, et al., "Functional Significance of Three Basic N-Terminal Amino Acids of Alfalfa Mosaic Virus Coat Protein" *Virology* 1998, 242: 1-5.
Yusibov et al., "Purification, characterization, assembly and crystallization of assembled alfalfa mosaic virus coat protein expressed in *Escherichia coli", J. Gen. Virol.*, 1996, 77:567-573.
Yusibov et al., "Expression in plants and immunogenicity of plant virus-based experimental rabies vaccine" *Vaccine,* 2002, 20:3155-3164.
Zumbach et al., "Antibodies Against Oncoproteins E6 and E7 of Human Papillomavirus Types 16 and 18 in Patients with Head-and-Neck Squamous-Cell Carcinoma", *International Journal of Cancer,* 2000, 85:815-818.
Advisory Action dated Jan. 15, 2010 for U.S. Appl. No. 11/706,568 (3 pgs.).
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003973 (6 pgs.).
International Preliminary Report on Patentability dated Aug. 19, 2008 for Int'l. Appln. No. PCT/US07/003969 (6 pgs.).
International Preliminary Report on Patentability dated Mar. 4, 2010 for Int'l. Appln. No. PCT/US08/073776 (6 pgs.).
International Search Report and Written Opinion dated Aug. 3, 2007 for Int'l. Appln. No. PCT/US07/003973 (9 pgs.).
International Search Report and Written Opinion dated Jun. 18, 2008 for Int'l Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Apr. 24, 2009 for Int'l. Appln. No. PCT/US08/073776 (11 pgs.).
Office Action (non-final) dated Nov. 4, 2008 for U.S. Appln. No. 11/706,568 (7 pgs.).

Office Action (non-final) dated Jan. 6, 2009 for U.S. Appln. No. 11/706,568 (8 pgs.).
Office Action (final) dated Jul. 15, 2009 for U.S. Appln. No. 11/706,568 (7 pgs.).
Supplementary European Search Report dated May 5, 2010 for European Appln. No. EP 07750784 (8 pgs.).
Anderson et al., "Recombinant V Antigen Protects Mice against Pneumonic and Bubonic Plague Caused by F1-Capsule-Positive and -Negative Strains of *Yersinia pestis*", *Infect. Immun.*, 64(11):4580-5, 1996.
Andrews et al., "Fraction 1 Capsular Antigen (F1) Purification from *Yersinia pestis* C092 and from an *Escherichia coli* Recombinant Strain and Efficacy against Lethal Plague Challenge", *Infect. Immun.*, 64(6):2180-7, 1996.
Brodzik et al., "Advances in alfalfa mosaic virus-mediated expression of anthrax antigen *in planta"*, *Biochem. Biophys. Res. Commun.*, 338( 2):717-722, 2005.
Chain et al., "Complete Genome Sequence of *Yersinia pestis* Strains Antigua and Nepal516: Evidence of Gene Reduction in an Emerging Pathogen", *J. Bacteriol.*, 188(12):4453-63, 2006.
Chichester et al., "Different response requirements for IFNγ production in ELISPOT assays by CD4+ T cells from mice early and late after submission", *J. Immunol. Methods*, 309:99-107, 2006.
Chichester et al , "Immunogenicity of a subunit vaccine against *Bacillus anthracis*", *Vaccine*, 25:3111-3114, 2007.
Deng et al., "Genome Sequence of *Yersinia pestis* KIM", *J. Bacteriol.*, 184(16):4601-11, 2002.
Heath et al., "Protection against experimental bubonic and pneumonic plague by a recombinant capsular F1-V antigen fusion protein vaccine", *Vaccine*, 16(11/12):1131-7, 1998.
Li et al , "Immunization with recombinant beta-tubulin from *Trypanosoma evansi* induced protection against *T. evansi, T. equiperdum* and *T. b. brucei* infection in mice", *Parasite Immunology*, 29:191-199, 2007.
Parkhill et al., "Genome sequence of *Yersinia pestis*, the causative agent of plague", *Nature*, 413:523-7, 2001.
UniProt Database accession No. P04107 Nov. 1, 1986.
Williamson et al., "Human Immune Response to a Plague Vaccine Comprising Recombinant F1 and V Antigens", *Infect. Immun.*, 73(6):3598-608, 2005.
Williamson et al., "A single dose sub-unit vaccine protects against pneumonic plague", *Vaccine*, 19:566-71, 2000.
Williamson et al., "A new improved sub-unit vaccine for plague: the basis of protection", *FEMS Immunol. Med. Microbiol.*, 12:223-30, 1995.
International Preliminary Report on Patentability dated Nov. 3, 2009 for Int'l Appln. No. PCT/US08/061782 (7 pgs.).
International Search Report and Written Opinion dated Oct. 21, 2008 for Int'l. Appln. No. PCT/US08/061782 (10 pgs.).
Accession CAA4959, Apr. 18, 2005.
Ahlquist et al., "Gene Expression Vectors Derived from Plant RNA Viruses", Current Communications in Molecular Biology—Viral Vectors, (Ed., Gluzman et al.) 183-189, 1988.
Air GM, "Mechanism of antigenic variation in an individual epitope on influenza virus N9 neuraminidase", *J. Virology*, 64(12):5797-5803, 1990.
Akol and Murray, "Trypanosoma congolense: Susceptibility of cattle to cyclical challenge," Exp. Parasitol., 55:386-393, 1983.
Alignment of 11706573-6 to SEQ ID No. 6 U.S. Appl. No. 10/558,109 on Feb. 24, 2009.
Alignment of 11706573-30 to SEQ ID No. 6 U.S. Appl. No. 10/558,109 on Feb. 24, 2009.
Alignment of 11706576-12 to SEQ ID No. 6 U.S. Appl. No. 10/558,109 on Feb. 24, 2009.
Alignment of 12110877-30 to SEQ ID No. 6 U.S. Appl. No. 10/558,109 on Feb. 24, 2009.
Ay et al., "Crystal structures and properties of de novo circularly permuted 1,3-1,4-beta-glucanases," Proteins, 30(2): 155-67, Feb. 1, 1998.
Aymard et al., "Role of antineuraminidase antibodies in protection against influenza", *Bulletin de l'Academie nationale de medicine*, 182(8): 1723-1736 (1998).
Aymard et al., "Neuraminidase assays," *Developments in Biologicals*, 115:75-83 (2003).
Barbas et al., "Assembly of combinatorial antibody libraries on phage surfaces: the gene III site," *Proc. Natl. Acad. Sci. USA* 88:7978 (1991).
Barbas et al., "Semisynthetic combinatorial antibody libraries: a chemical solution to the diversity problem," *Proc. Natl. Acad. Sci. USA* 89:4457 (1992).
Berger et al., "Therapeutic applications of monoclonal antibodies" *Am J Med Sci.*, 324(1):14-30 (2002).
Broothaerts et al. *Nature*, 433:629-33 (2005).
Burke et al. *Science* 236:806 (1987).
Calandrelli et al., "Purification and characterization of thermostable eylanase and beta-xylosidase by the termophilic bacterium Bacillus termantarcticus," *Res. Microbiol.*, 155(4): 283-9, 2004.
Chica et al., "Semi-rational approaches to engineering enzyme activity: combining the benefits of directed evolution and rational design," *Curr. Opin. Biotechnol.*, 16:378-384, 2005.
Chichester et al., *J. Immunol. Methods*, 309:99-107 (2006).
Dawson et al., "cDNA cloning of the complete genome of tobacco mosaic virus and production of infectious transcripts," *Proc. Natl Acad. Sci. USA*, 83:1832 (1986).
Floss, D. M. et al., "Production of vaccines and therapeutic antibodies for veterinary applications in transgenic plants: an overview", *Transgenic Research*, vol. 16, No. 3, Jun. 2007, pp. 315-332.
Fütterer et al., "Use of DNA Plant Viruses and Plant Viral Expression Signals for Gene Expression in Plants and Plant Protoplasts," *Curr. Commun. Mol. Biol.— Viral Vectors*, (Ed., Gluzman et al.) 178-182 (1988).
Herbert and Lumsden, "*Trypanosoma brucei*: A rapid 'matching' method for estimating the host's parasitemia," Exp. Parasitol, 40:427, 1976.
Huber et al., (2006), Clin. Vaccine Immunol., 13:981-90.
Huse et al. (1989) Science 246:1275.
Jirholt et al., (1998) Gene 215:471.
Johnson et al., Respiratory syncytial virus (RSV) G glycoprotein is not necessary for vaccine-enhanced disease induced by immunization with formalin-inactivated RSV, J. Virol, 78(11):6024-32, 2004.
Jones et al. (1986) Nature 321:522.
Kang et al. (1991) Proc. Natl. Acad. Sci USA 88:4363.
Katayama and Mine, 2006, J. Agric. Food Chem., 54:3271-6.
Knapp et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move", J. Virol., 2001, 75:5518.
Konieczny et al. (1981) Haematologia (Budap.) 14:95.
Kubler-Kielb, J. et al., "Long-lasting and transmission-blocking activity of antibodies to *Plasmodium falciparum* elicited in mice by protein conjugates of Pfs25", Proceedings of the National Academy of Sciences of USA, vol. 104, No. 1, Jan. 1, 2007, pp. 293-298.
Lee, J. T. and Air, G. M., "Contacts between influenza virus N9 neuraminidase and monoclonal antibody NC10", Virology, 300(2): 255-268, Sep. 1, 2002.
Lensen, A. et al., "Measurement by membrane feeding of reduction in *Plasmodium falciparum* transmission induced by endemic sera", Trans R Soc Trop Med Hyg. Jan.-Feb. 1996;90(1):20-2.
Lewandowski and Dawson, "Deletion of Internal Sequences Results in Tobacco Mosaic Virus Defective RNAs That Accumulate to High Levels without Interfering with Replication of the Helper Virus", Virology, 1998, 251:427-437.
Lorence and Verpoorte (2004), Methods Mol. Biol., 267:329-50.
Lubega et al , "Immunization with a tubulin-rich preparation from *Trypanosoma brucei* confers broad protection against African trypanosomosis," *Exp. Parasitol.*, 2002, 102:9-22.
Lubega et al., "*Trypanosome brucei*: anti-tubulin antibodies specifically inhibit trypanosome growth in culture," *Exp. Parasitol.*, 2002, 102:134-142.
Mathew, Plant Viruses Online—Cassava Indian mosaic bigeminvirus (http://imagels.uidaho.eduivide/), downloaded on Feb. 21, 2006, 5 pgs.
Mbawuike et al., 2007, Vaccine, 25:3263-9.

Mett, V. et al., "Plants as biofactories", Biologicals: *Journal of the International Association of Biological Standardization,* vol. 36, No. 6, Nov. 2008, pp. 354-358.
Mett, V., et al., "A plant-produced plague vaccine candidate confers protection to monkeys", Vaccine, Apr. 20, 2007, vol. 25, No. 16, pp. 3014-3017.

Moayeri et al., "The roles of anthrax toxin in pathogenesis," Curr Opin Michrobiol, 7(1):19-24, 2004.

Moreira et al., "A Thermostable Maltose-tolerant α-anylase from Asperillgus Tamarii," J. Basic Microbiology, 44: 29-35, 2004.

Morrison et al. (1984) Proc. Natl. Acad. Sci USA 81:6851.

Morrison et al. (1986) Mt. Sinai J. Med. 53:175.
Pruett PS, et al., "Critical interactions in binding antibody NC41 to influenza N9 neuraminidase: amino acid contacts on the antibody heavy chain", *Biochemistry,* 37:10660-10670, 1998.
Qian et al., "Conjugating recombinant proteins to *Pseudomonas aeruginosa* ExoProtein A: A strategy for enhancing immunogenicity of malaria vaccine candidate", Vaccine, vol. 25, No. 20, Apr. 24, 2007, pp. 3923-3933.

Rasooly-Balaban, "Trypanosome microtubule-associated protein p15 as a vaccine for the prevention of African sleeping sickness", Vaccine, vol. 22, No. 8, Feb. 25, 2004, pp. 1007-1015.

Riechmann et al. (1988) Nature 332:323.

Rowe et al., J. Clin. Microbiol., 1999, 37:937-43.

Sabbatini et al., 2007, Clin. Cancer Res., 13:4170-7.

Santi, V., et al., "Protection conferred by recombinant *Yersinia pestis* antigens produced by a rapid and highly scalable plant expression system", Proc. Natl. Acad. Sci. USA, Jan. 24, 2006, vol. 103, No. 4, pp. 861-866.
Saravolac EG, et al "Immunoprophylactic strategies against respiratory influenza virus infection." *Vaccine,* Mar. 21, 2001;19(17-19):2227-32.
Schild et al. (1975) Bull. World Health Org., 52:223-31.
Sen et al., Appl Biochem Biotechnol., 143(3):212-23, Dec. 2007.
Shima et al., "hyperthermaphilic and salt-dependent formytransferase from *Methanopyrus* kanleri," *Biochem Soc. Trans.,* 32:269-72, 2004.
Shimasaki et al., "Rapid diagnostics: the detection of neuraminidase activity as a technology for high-specificity targets", Philosophical transactions of the Royal Society of London. Series B, Biological sciences, 356(1416): 1925-1931 (Dec. 29, 2001).
Shoji, Y. et al , "Immunogenicity of hemagglutinin from A/Bar-headed/Goose/Qinghai/1A/05 and A/Anhui/1/05 strains of H5N1 influenza viruses produced in *Nicotiana benthamiana* plants", *Vaccine,* vol. 27, No. 25-26, May 26, 2009, pp. 3467-3470.
Shoji, Y. et al., "Plant-expressed HA as a seasonal influenza vaccine candidate", *Vaccine,* vol. 26, No. 23, Jun. 2, 2008, pp. 2930-2934.
Smahel et al., "Modified HPV16 E7 Genes as DNA Vaccine against E7-Containing Oncogenic Cells", Virology, 281, 231-238 (2001).
Snow et al, 2005, Nature, 434:214-7.
Soderlind et al. (1999) Immunotechnol. 4:279.
Soderlind et al. (2000) Nature Biotechnol. 18:852.
Stewart et al., "Mutant barley (1→3,1→4)-β-glucan endohydrolases with enhanced thermostability", Protein Engineering, vol. 14, No. 4, pp. 245-253, (2001).
Throsby, M. et al., "Heterosubtypic neutralizing monoclonal antibodies cross-protective against H5N1 and H1N1 recovered from human IgM+ memory B cells ", Plos One 2008 LNKD-PUBMED:19079604, vol. 3, No. 12, 2008, p. E3942.
Tsai et al., "Crystal structure of a natural circularly permuted jellyroll protein: 1,3-1,4-beta-D-glucanase from Fibrobacter succinogens," J Mol Biol., 330(3):607-20, Jul. 11, 2003.
UniProt Database [Online] EBI Accession No. Q0PDN1, "SubName: Full=Hemagglutinin", Sep. 5, 2006.
UniProt Database [Online] EBI Accession No. A9X0E7, "SubName: Full=Hemagglutinin; Flags: Precursor", Feb. 5, 2008.
Van der Kolk, M. et al., Parasitology, Jan. 2005; 130(Pt 1): 13-22 (Erratum in: Parasitology Oct. 2005; 131(Pt 4):578.
Voinnet et al. (2003) Plant J. 33:949.
Wang et al , "Immunogenicity of *Plasmodium yoelii* merozoite surface protein 4/5 produced in transgenic plants", International Journal of Parasitology, vol. 38, No. 1, Dec. 22, 2007 pp. 103-110.
Wang et al., "Structural Basis for Thermostability of β-Glycosidase from the Thermophilic Eubacterium Thermus Nonproteolyticus HG102," J. Bacteriology, 185: 4248-55, 2003.
Webster RG, et al., "Antigenic Structure and Variation in an Influenza Virus N9 Neuraminidase", *J. Virology,* 61:2910-2916, 1987.
Wiesmuller et al., "Peptid Vaccines and Peptide Libraries," Biol Chem., 382(4): 571-9, Apr. 2001.
Winter and Milstein (1991) Nature 349:293.
Woo, P. T. K., "The Haematocrit Centrifuge Technique for the Diagnosis of African Trypanosomiasis", Acta Tropica, 27:384, 1970.
Yang, M. et al., "Production and diagnostic application of monoclonal antibodies against influenza virus H5", *Journal of Virological Methods,* vol. 162, No. 1-2, Aug. 21, 2009, pp. 194-202.
Yusibov et al., "An influenza N1 neuraminidase-specific monoclonal antibody with broad inactivating activity against H5N1 viruses", *Human Antibodies,* vol. 16, No. 1-2, 2007, p. 33.
Yusibov et al., "An influenza N1 neuraminidase-specific monoclonal antibody protects animal against live challenge with homologous H5N1 virus", *Human Antibodies,* vol. 17, No. 1-2, 2008, p. 15.
Zapata et al., (1995) Prot. Eng., 8:1057.
Communication dated Sep. 23, 2009 for corresponding European Appln. No. 04 776 107.7 (3 pgs.).
Communication dated Feb. 18, 2010 for EP Appln. No. EP 07750905.7 (2 pgs.).
International Preliminary Report on Patentability dated Mar. 17, 2009 for Int'l. Appln. No. PCT/US07/004103 (5 pgs.).
International Preliminary Report on Patentability dated Jan. 12, 2010 for International Appln. No. PCT/US2008/069860 (5 pgs.).
International Preliminary Report on Patentability for International Appln. No. PCT/US2009/058640 dated Mar. 29, 2011 (7 pgs.).
International Preliminary Report on Patentability dated Mar. 29, 2011 for Int'l Appln. No. PCT/US2009/058669 (12 pgs.).
International Search Report dated Dec. 23, 2005 for International Appln. No. PCT/US04/16452 (2 pgs.).
International Search Report and Written Opinion dated Aug. 7, 2007 for Int'l. Appln. No. PCT/US07/004103 (9 pgs).
International Search Report and Written Opinion dated May 29, 2009 for International Appln. No. PCT/US2008/069860 (8 pgs.).
International Search Report and Written Opinion dated May 11, 2010 for International Appln. No. PCT/US2009/058488 (20 pgs.).
International Search Report and Written Opinion for International Appln. No. PCT/US2009/058640 dated Feb. 2, 2010 (13 pgs.).
International Search Report and Written Opinion dated May 19, 2010 for International Appln. No. PCT/US2009/058669 (21 pgs.).
International Search Report and Written Opinion dated Jan. 27, 2011 for Int'l Appln. No. PCT/US10/050693 (7 pgs.).
Notification of Defects in Patent Application dated Sep. 16, 2010 for Israeli Patent Appln. No. 193391 (3 pgs.).
Supplementary European Search Report dated Oct. 8, 2009 for European Appln. No. EP 07750950 (5 pgs.).
Supplementary European Search Report dated Jun. 9, 2010 for European Appln. No. EP 08 78 0572 (5 pgs.).

* cited by examiner

Lanes:
1. LicKM control
2, 3. LicKM-NA
4, 5. PR-LicKM-NA
6, 7. PR-LicKM-NA-KDEL

INFLUENZA ANTIGENS, VACCINE COMPOSITIONS, AND RELATED METHODS

RELATED APPLICATIONS

The present application is related to and claims priority under 35 USC 119(e) to U.S. Ser. No. 60/773,378, filed Feb. 13, 2006 (the '378 application) and to U.S. Ser. No. 60/813,955, filed Jun. 15, 2006 (the '955 application); the entire contents of the '139 application and the '955 application are incorporated herein by reference.

BACKGROUND OF THE INVENTION

Influenza has a long history characterized by waves of pandemics, epidemics, resurgences and outbreaks. Influenza is a highly contagious disease that could be equally devastating both in developing and developed countries. The influenza virus presents one of the major threats to the human population. In spite of annual vaccination efforts, influenza infections result in substantial morbidity and mortality. Although flu epidemics occur nearly every year, fortunately pandemics do not occur very often. However, recent flu strains have emerged such that we are again faced with the potential of an influenza pandemic. Avian influenza virus of the type H5N1, currently causing an epidemic in poultry in Asia as well as regions of eastern Europe, has persistently spread throughout the globe. The rapid spread of infection, as well as cross species transmission from birds to human subjects, increases the potential for outbreaks in human populations and the risk of a pandemic. The virus is highly pathogenic, resulting in a mortality rate of over fifty percent in birds as well as the few human cases which have been identified. If the virus were to achieve human to human transmission, it would have the potential to result in rapid, widespread illness and mortality.

The major defense against influenza is vaccination. Influenza viruses are segmented, negative-strand RNA viruses belonging to the family Orthomyxoviridae. The viral antigens are highly effective immunogens, capable of eliciting both systemic and mucosal antibody responses. Influenza virus hemagglutinin glycoprotein (HA) is generally considered the most important viral antigen with regard to the stimulation of neutralizing antibodies and vaccine design. The presence of viral neuraminidase (NA) has been shown to be important for generating multi-arm protective immune responses against the virus. Antivirals which inhibit neuraminidase activity have been developed and may be an additional antiviral treatment upon infection. A third component considered useful in the development of influenza antivirals and vaccines is the ion channel protein M2.

Subtypes of the influenza virus are designated by different HA and NA resulting from antigenic shift. Furthermore, new strains of the same subtype result from antigenic drift, or mutations in the HA or NA molecules which generate new and different epitopes. Although 15 antigenic subtypes of HA have been documented, only three of these subtypes H1, H2, and H3, have circulated extensively in humans. Vaccination has become paramount in the quest for improved quality of life in both industrialized and underdeveloped nations. The majority of available vaccines still follow the basic principles of mimicking aspects of infection in order to induce an immune response that could protect against the relevant infection. However, generation of attenuated viruses of various subtypes and combinations can be time consuming and expensive. Emerging new technologies, in-depth understanding of a pathogen's molecular biology, pathogenesis, and its interactions with an individual's immune system have resulted in new approaches to vaccine development and vaccine delivery. Thus, while technological advances have improved the ability to produce improved influenza antigens vaccine compositions, there remains a need to provide additional sources of vaccines and new antigens for production of vaccines to address emerging subtypes and strains. Improved vaccine design and development for influenza virus subtypes, as well as methods of making and using such compositions of matter are needed which provide inexpensive and highly accessible sources of such therapeutic compositions.

SUMMARY OF THE INVENTION

The present invention provides influenza antigens and vaccine components produced in plants. The present invention provides one or more influenza antigens generated as a fusion with a thermostable protein. The invention further provides vaccine compositions containing influenza antigens. Furthermore, the invention provides influenza vaccines comprising at least two different influenza antigens. In some embodiments, inventive compositions include one or more plant components. Still further provided are methods for production and use of the antigen and vaccine compositions of the invention.

BRIEF DESCRIPTION OF THE DRAWING

FIG. 1. Schematic of hemagglutinin (HA) protein and protein domains. The numbers 1, 2, and 3 in the upper left correspond to domains 1, 2, and 3 described herein. Domains 1, 2, and 2, 1 fold together to form a stem domain (SD). Domain 3 is a globular domain (GD). The ranges presented in items 1-6 correspond to amino acid positions of HA.

FIG. 2. Map of the pET32 plasmid. The top left indicates the region between the T7 promoter and the T7 terminator lacking in modified plasmid used for cloning target antigen.

FIG. 3. Schematic of the pET-PR-LicKM-KDEL and pET-PR-LicKM-VAC constructs inserted into a modified pET32a vector.

FIG. 4. Schematic of the pBI121 vector organization.

FIG. 5. Schematic organization of the derivation of the pBID4 plasmid from a pBI vector after excision of the GUS gene and the addition of a TMV-derived plasmid.

FIG. 6. Schematic of the fusion of HA, domains of HA, and NA in lichenase sequence, with and without targeting sequences which were put into a vector.

FIGS. 7A,B. Lichenase assays of extracts of plants expressing LicKM and fusion proteins. (7A) Transient expression of lichenase in *Nicotiana benthamiana*. (7B) Zymogram of lichenase HA fusion proteins in plants (arrow).

FIG. 8. Western analysis of extracts of plants expressing Lic-HA fusion proteins using anti-HA and anti-LicB antibodies.

FIG. 9. Lichenase assays of extracts of plants expressing Lic-NA fusion proteins.

FIG. 10. Western analysis of extracts of plants expressing Lic-HA fusion proteins.

FIG. 11. Red blood cell hemagglutination assay with plant expressed HA lichenase fusion proteins.

FIG. 12. Antibody response of mice immunized with test H5N1 influenza vaccine, with and without adjuvant.

FIG. 13. Hemaggultination activity inhibition by serum dilutions obtained from mice immunized with H5N1 test vaccine, with and without adjuvant.

FIGS. 14A-D. Symptoms following H3N2 virus challenge in H3N2 influenza test vaccine and control treatment groups.

(14A) Overall mean maximum results of clinical symptom scores. (14B) Overall mean maximum results of cell counts in nasal washes after virus challenge. (14C) Overall mean maximum results of weight loss in animals. (14D) Overall mean maximum of temperature change in animals.

Figure 15:
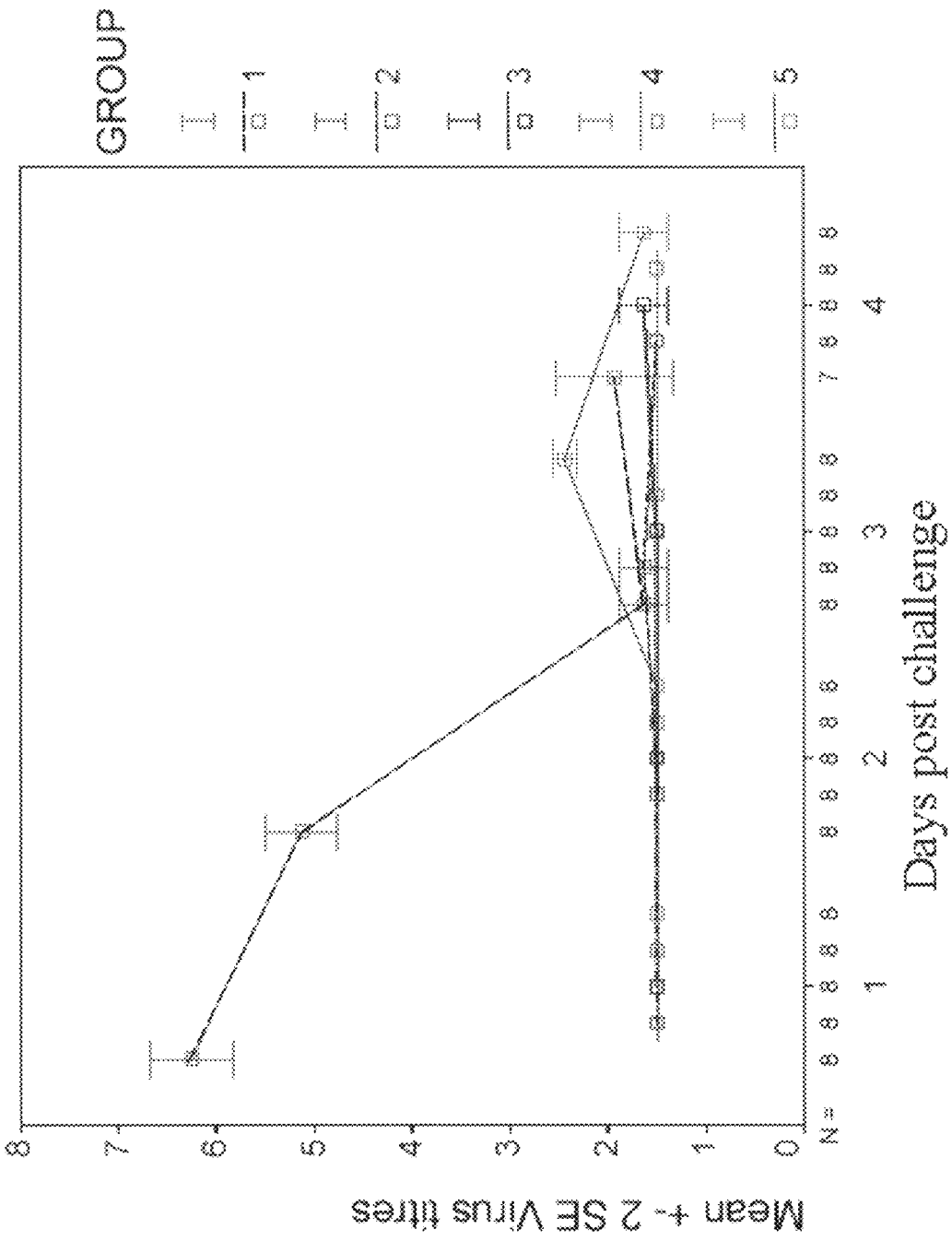

FIG. 15. Virus shedding following H3N2 virus challenge in H3N2 influenza test vaccine and control treatment groups. Group 1 depicts results from the negative control treatment group; Group 2 depicts results from animals treated with Test article 1 (CMB F1); Group 3 depicts results from animals treated with Test article 2 (CMB F2); Group 4 depicts results from animals treated with Test article 3 (CMB F3); and Group D depicts results from positive control treated animals. N refers to the number of animals assessed in each group (8 in each group).

Figure 16:
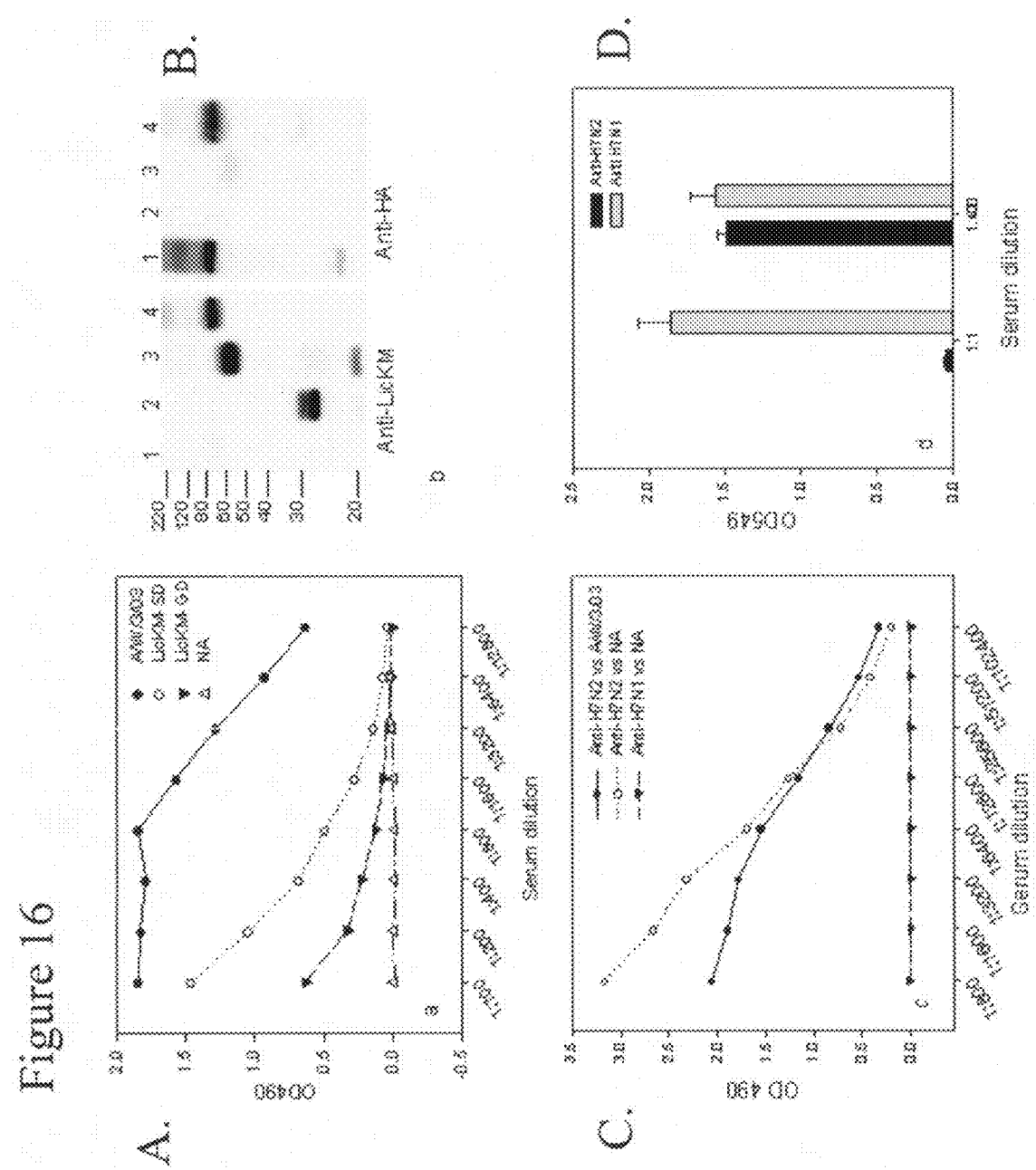

FIG. 16. Characterization of influenza A/Wyoming/3/03 virus antigens produced in plants. (16A) ELISA analysis of LicKM-(SD) and LicKM-(GD) using sheep serum raised against purified HA from influenza A/Wyoming/3/03 virus. Homologous virus (A/W/3/03) and plant-produced NA were used as positive and negative controls, respectively. (16B) Immunoblot analysis of LicKM-HA(SD) (lane 4) and LicKM-HA(GD) (lane 3) using rabbit serum raised against LicKM (anti-LicKM) and sheep serum raised against purified HA of influenza A/Wyoming/3/03 virus (anti-HA). LicKM (lane 2) and homologous virus (lane 1) were used as controls. (16C) ELISA analysis of NA using sheep sera raised against NIBRG-18 reassorted virus (anti-H7N2) and NIBRG-17 reassorted virus (anti-H7N1). Homologous virus (A/W/3/03) assessed using sheep serum to NIBRG-18 (anti-H7N2) was used as a positive control. (16D) Strain specific inhibition of neuraminidase activity following pre-incubation with sheep serum raised against NIBRG-18 (anti-H7N2) or NIBRG-17 (anti-H7N1). Mean enzymatic activity from three replicates are shown with standard deviations.

Figure 17:
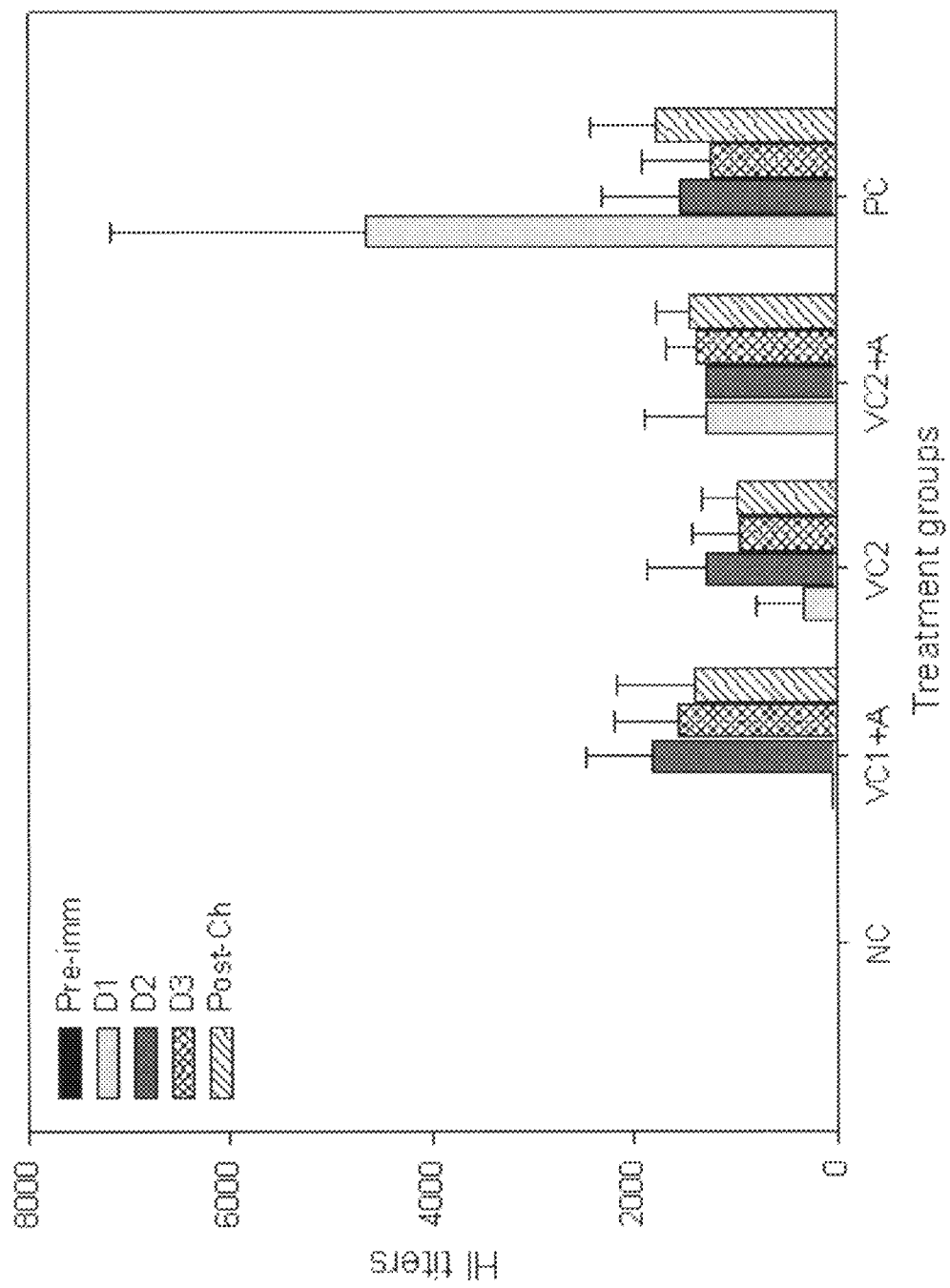

FIG. 17. Hemagglutination inhibition titers of sera from ferrets immunized with VC1 plus adjuvant, VC2 no adjuvant, or VC2 plus adjuvant. Serum samples were collected prior to the first dose (Pre-imm), 14 days after the first dose (D1), 14 days after the second dose (D2), 10 days after the third dose (D3), and 4 days post-challenge (Post-Ch). Geometric mean titers with standard deviations are shown.

Figure 18:
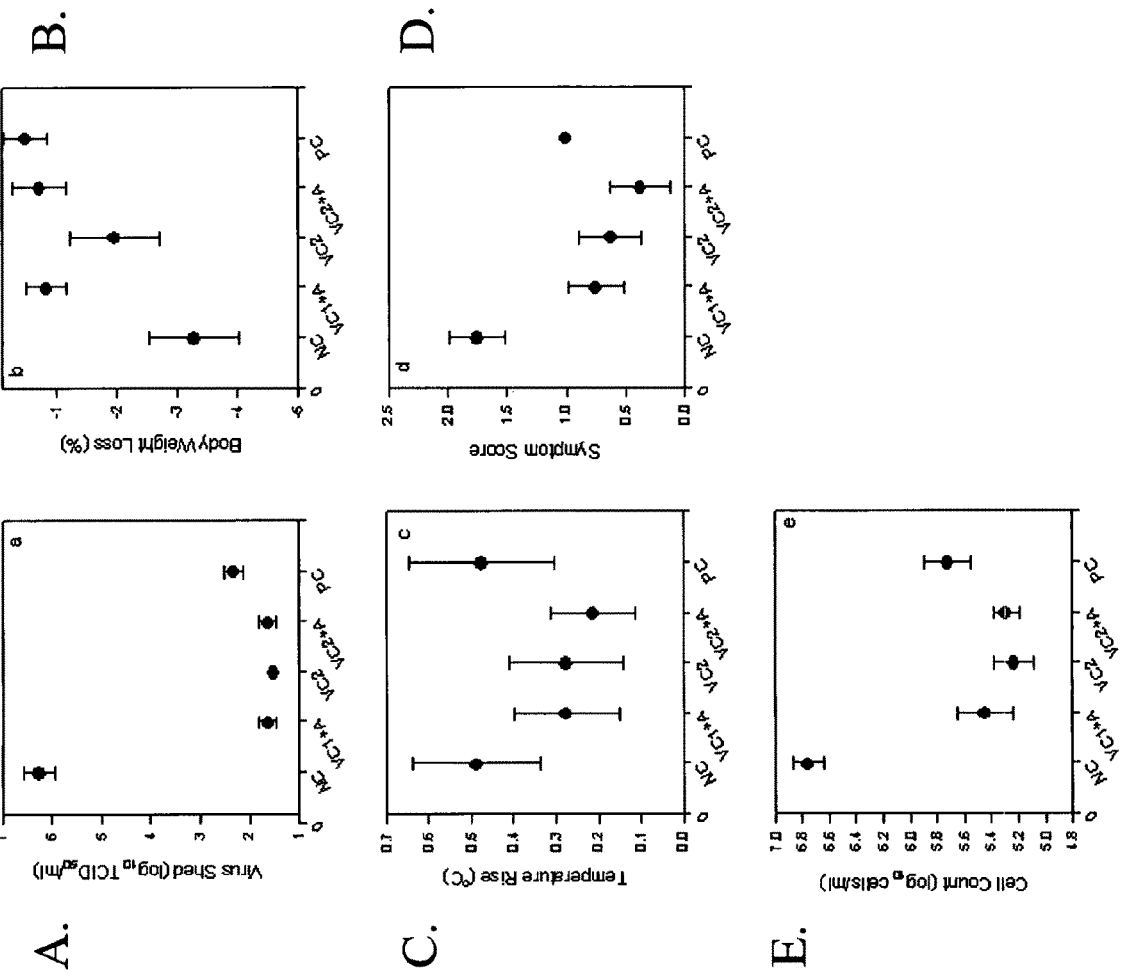

FIG. 18. Post-challenge monitoring of ferrets immunized with VC1 plus adjuvant, VC2 no adjuvant, or VC2 plus adjuvant. Mean values with standard deviations are shown, and statistical analysis of data was conducted using ANOVA with the Bonferroni correction for multiple testing. Statistical significance was defined as a $p \leq 0.05$. (18A) Peak of virus shed post-infection. (18B) Maximum weight loss post-infection. (18C) Peak temperature rise post-infection. (18D) Peak of symptom scores post-infection. (18E) Peak of total leukocyte counts per ml of nasal wash samples post-infection.

DETAILED DESCRIPTION OF THE INVENTION

The invention relates to influenza antigens useful in the preparation of vaccines against influenza infection, and fusion proteins comprising such influenza antigens operably linked to thermostable protein. The invention relates to methods of production of provided antigens, including but not limited to, production in plant systems. Further, the invention relates to vectors, fusion proteins, plant cells, plants and vaccine compositions comprising the antigens and fusion proteins of the invention. Still further provided are methods of inducing immune response against influenza infection in a subject comprising administering vaccine compositions of the invention to a subject.

Influenza Antigens

Influenza antigen proteins of the present invention include any immunogenic protein or peptide capable of eliciting an immune response against influenza virus. Generally, immunogenic proteins of interest include influenza antigens (e.g., influenza proteins, fusion proteins, etc.), immunogenic portions thereof, or immunogenic variants thereof and combinations of any of the foregoing.

Influenza antigens for use in accordance with the present invention may include full-length influenza proteins or fragments of influenza proteins, and/or fusion proteins comprising full-length influenza proteins or fragments of influenza proteins. Where fragments of influenza proteins are utilized, whether alone or in fusion proteins, such fragments retain immunological activity (e.g., cross-reactivity with anti-influenza antibodies). Based on their capacity to induce immunoprotective response against viral infection, hemagglutinin and neuraminidase are primary antigens of interest in generating vaccines. Additional antigens, such as the membrane ion channel M2 may be useful in production of vaccines (e.g., combination vaccines) in order to improve efficacy of immunoprotection.

Thus, the invention provides plant cells and plants expressing a heterologous protein (e.g., an influenza antigen (e.g., influenza protein or a fragment thereof, a fusion protein comprising an influenza protein or fragment thereof). A heterologous protein of the invention can comprise any influenza antigen of interest, including, but not limited to hemagglutinin (HA), neuraminidase (NA), membrane ion channel M2 (M2), a portion of hemagglutinin (HA), a portion of neuraminidase (NA) and a portion of membrane ion channel (M2), or fusion proteins, fragments, or combinations of hemagglutinin (HA), neuraminidase (NA), membrane ion channel M2 (M2), a portion of hemagglutinin (HA), a portion of neuraminidase (NA) and/or a portion of membrane ion channel (M2).

Amino acid sequences of a variety of different influenza HA, NA and M2 proteins (e.g., from different subtypes, or strains or isolates) are known in the art and are available in public databases such as GenBank. Exemplary full length protein sequences for HA and NA of two influenza subtypes of particular interest today, as well as sequence for M2 are provided below:

```
V: Vietnam H5N1
HA (HAV) SEQ ID NO.: 1
AKAGVQSVKMEKIVLLFAIVSLVKSDQICIGYHANNSTEQVDTIMEKNVT

VTHAQDILEKTHNGKLCDLDGVKPLILRDCSVAGWLLGNPMCDEFINVPE

WSYIVEKANPVNDLCYPGDFNDYEELKHLLSRINHFEKIQIIPKSSWSSH

EASLGVSSACPYQGKSSFFRNVVWLIKKNSTYPTIKRSYNNTNQEDLLVL

WGIHHPNDAAEQTKLYQNPTTYISVGTSTLNQRLVPRIATRSKVNGQSGR

MEFFWTILKPNDAINFESNGNFIAPEYAYKIVKKGDSTIMKSELEYGNCN

TKCQTPMGAINSSMPFHNIHPLTIGECPKYVKSNRLVLATGLRNSPQRER

RRKKRGLFGAIAGFIEGGWQGMVDGWYGYHHSNEQGSGYAADKESTQKAI

DGVTNKVNSIIDKMNTQFEAVGREFNNLERRIENLNKKMEDGFLDVWTYN

AELLVLMENERTLDFHDSNVKNLYDKVRLQLRDNAKELGNGCFEFYHKCD

NECMESVRNGTYDYPQYSEEARLKREEISGVKLESIGIYQILSIYSTVAS

SLALALMVAGLSLWMCSNGSLQCRICI
```

```
NA (NAV) SEQ ID NO.: 2:
MNPNQKIITIGSICMVTGIVSLMLQIGNMISIWVSHSIHTGNQHQSEPIS

NTNLLTEKAVASVKLAGNSSLCPINGWAVYSKDNSIRIGSKGDVFVIREP

FISCSHLECRTFFLTQGALLNDKHSNGTVKDRSPHRTLMSCPVGEAPSPY

NSRFESVAWSASACHDGTSWLTIGISGPDNGAVAVLKYNGIIITDTIKSWR

NNILRTQESECACVNGSCFTVMTDGPSNGQASHKIFKMEKGKVVKSVELD

APNYHYEECSCYPDAGEITCVCRDNWHGSNRPWVSFNQNLEYQIGYICSG

VFGDNPRPNDGTGSCGPVSSNGAGGVKGFSFKYGNGVWIGRTKSTNSRSG

FEMIWDPNGWTETDSSFSVKQDIVAITDWSGYSGSFVQHPELTGLDCIRP

CFWVELIRGRPKESTIWTSGSSISFCGVNSDTVGWSWPDGAELPFTIDK

W: Wyoming H3N2
HA (HAW) SEQ ID NO.: 3:
MKTIIALSYILCLVFSQKLPGNDNSTATLCLGHHAVPNGTIVKTITNDQI

EVTNATELVQSSSTGGICDSPHQILDGENCTLIDALLGDPQCDGFQNKKW

DLFVERSKAYSNCYPYDVPDYASLRSLVASSGTLEFNNESFNWAGVTQNG

TSSACKRRSNKSFFSRLNWLTHLKYKYPALNVTMPNNEKFDKLYIWGVHH

PVTDSDQISLYAQASGRITVSTKRSQQTVIPNIGYRPRVRDISSRISIYW

TIVKPGDILLINSTGNLIAPRGYFKIRSGKSSIMRSDAPIGKCNSECITP

NGSIPNDKPFQNVNRITYGACPRYVKQNTLKLATGMRNVPEKQTRGIFGA

IAGFIENGWEGMVDGWYGFRHQNSEGTGQAADLKSTQAAINQINGKLNRL

IGKTNEKFHQIEKEFSEVEGRIQDLEKYVEDTKIDLWSYNAELLVALENQ

HTIDLTDSEMNKLFERTKKQLRENAEDMGNGCFKIYHKCDNACIESIRNG

TYDHDVYRDEALNNRFQIKGVELKSGYKDWILWISFAISCFLLCVALLGF

IMWACQKGNIRCNICI

NA (NAW) SEQ ID NO.: 4:
MNPNQKIITIGSVSLTISTICFFMQIAILITTVTLHFKQYEFNSPPNNQV

MLCEPTIIERNITEIVYLTNTTIEKEICPKLAEYRNWSKPQCNITGFAPF

SKDNSIRLSAGGDIWVTREPYVSCDPDKCYQFALGQGTTLNNVHSNDTVH

DRTPYRTLLMNELGVPFHLGTKQVCIAWSSSSCHDGKAWLHVCVTGDDEN

ATASFIYNGRLVDSIVSWSKKILRTQESECVCINGTCTVVMTDGSASGKA

DTKILFIEEGKIVHTSTLSGSAQHVEECSCYPRYPGVRCVCRDNWKGSNR

PIVDINIKDYSIVSSYVCSGLVGDTPRKNDSSSSHCLDPNNEEGGHGVK

GWAFDDGNDVWMGRTISEKLRSGYETFKVIEGWSNPNSKLQJNRQVIVDR

GNRSGYSGIFSVEGKSCINRCFYVELIRGRKQETEVLWTSNSIVVFCGTS

GTYGTGSWPDGADINLMPI

Influenza Hong Kong M2 protein SEQ ID NO.: 5:
LTEVETPIRNEWGCRCNDSSDP
```

Influenza Proteins

Hemagglutinin

In certain embodiments, full length hemagglutinin (HA) is utilized in vaccine compositions of the invention. In some embodiments one or more domains of HA is used. In certain embodiments, two or three or more domains are utilized, as one or more separate polypeptides or linked together in one or more fusion polypeptides. Certain exemplary embodiments provide influenza antigen comprising full length, domain 1-2 and domain 2-1 (referred to herein as HA1_2), or domain 3 of HA.

```
HA Vietnam [H5N1]:
H5N1 HA signal peptide SEQ ID NO.: 6:
AKAGVQSVKMEKIVLLFAIVSLVKS H5N1 HA domain 1-2 SEQ ID NO.: 7:
DQICIGYHANNSTEQVDTIMEKNVTVTHAQDILEKTFINGKL H5N1 HA domain 3 SEQ ID NO.: 33:
CDLDGVKPLILRDCSVAGWLLGNPMCDEFINVPEWSYIVEKANPVNDLCY

PGDFNDYEELKHLLSRINHFEKIQIIPKSSWSSHEASLGVSSACPYQGKS

SFFRNVVWLIKKNSTYPTIKRSYNNTNQEDLLVLWGIHHPNDAAEQTKLY

QNPTTYISVGTSTLNQRLVPRIATRSKVNGQSGRMEFFWTILKPNDAINF

ESNGNFIAPEYAYKIVKKGDSTIMKSELEYGNC

H5N1 HA domain 2-1 SEQ ID NO.: 8:
NTKCQTPMGAINSSMPFHNIHPLTIGECPKYVKSNRLVLATGLRNSPQRE

RRRKKRGLFGAIAGFIEGGWQGMVDGWYGYHHSNEQGSGYAADKESTQKA

IDGVTNKVNSIIDKMNTQFEAVGREFNNLERRIENLNKKMEDGFLDVWTY

NAELLVLMENERTLDFHDSNVKNLYDKVRLQLRDNAKELGNGCFEFYHKC

DNECMESVRNGTYDYPQYSEEARLKREEISGVKLESIGIYQI

H5N1 HA transmembrane domain SEQ ID NO.: 9:
LSIYSTVASSLALALMVAGLSLWMCSNGSLQCRICI HA A/Wyoming (H3N2)
H3N2 HA signal peptide SEQ ID NO.: 10:
MKTIIALSYILCLVFS H3N2 HA domain 1-2 SEQ ID NO.: 11:
QKLPGNDNSTATLCLGHHAVPNGTIVKTITNDQIEVTNATELVQSSSTGG
I H3N2 HA domain 3 SEQ ID NO.: 12:
CDSPHQILDGENCTLIDALLGDPQCDGFQNKKWDLFVERSKAYSNCYPYD

VPDYASLRSLVASSGTLEFNNESFNWAGVTQNGTSSACKRRSNKSFFSRL

NWLTHLKYKYPALNVTMPNNEKFDKLYIWGVHHPVTDSDQISLYAQASGR

ITVSTKRSQQTVIPNIGYRPRVRDISSRISIYWTIVKPGDILLINSTGNL

IAPRGYFKIRSGKSSIMRSDAPIGKC

H3N2 HA domain 2-1 SEQ ID NO.: 13:
NSECITPNGSIPNDKPFQNVNRITYGACPRYVKQNTLKLATGMRNVPEKQ

TRGIFGAIAGFIENGWEGMVDGWYGFRHQNSEGTGQAADLKSTQAAINQT

NGKLNRLIGKTNEKFHQIEKEFSEVEGRIQDLEKYVEDTKIDLWSYNAEL

LVALENQHTIDLTDSEMNKLFERTKKQLRENAEDMGNGCFKIYHKCDNAC

IESIRNGTYDHDVYRDEALNNRFQIKGVELKSGYKDWIL

H3N2 HA transmembrane domain SEQ ID NO.: 14:
WISFAISCFLLCVALLGFIMWACQKGNIRCNICI
```

In certain embodiments, full length neuraminidase (NA) antigen is utilized in vaccine antigens of the invention. In some embodiments, a domain of NA is used. In certain embodiments two or three or more domains are provided in antigens of the invention. Certain exemplary embodiments provide influenza antigen comprising full length NA, lacking anchor peptide sequence.

Neuraminidase
NA Vietnam
H5N1 NA anchor peptide SEQ ID NO.: 15:
MNPNQKIITIGSICMVTGIVS

H5N1 NA SEQ ID NO.: 16:
LMLQIGNMISIWVSHSIHTGNQHQSEPISNTNLLTEKAVASVKLAGNSSL

CPINGWAVYSKDNSIRIGSKGDVFVIREPFISCSHLECRTFFLTQGALLN

DKHSNGTVKDRSPHRTLMSCPVGEAPSPYNSRFESVAWSASACHDGTSWL

TIGISGPDNGAVAVLKYNGIITDTIKSWRNNILRTQESECACVNGSCFTV

MTDGPSNGQASHKIFKMEKGKVVKSVELDAPNYHYEECSCYPDAGEITCV

CRDNWHGSNRPWVSFNQNLEYQIGYICSGVFGDNPRPNDGTGSCGPVSSN

GAGGVKGFSFKYGNGVWIGRTKSTNSRSGFEMIWDPNGWTETDSSFSVKQ

DIVAITDWSGYSGSFVQHPELTGLDCIRPCFWVELIRGRPKESTIWTSGS

SISFCGVNSDTVGWSWPDGAELPFTIDK

H3N2 NA anchor peptide SEQ ID NO.: 17:
MNPNQKIITIGSVSLTISTICFFMQIAILITTVTLHF

H3N2 NA SEQ ID NO.: 18:
KQYEFNSPPNNQVMLCEPTIIERNITEIVYLTNTTIEKEICPKLAEYRNW

SKPQCNITGFAPFSKDNSIRLSAGGDIWVTREPYVSCDPDKCYQFALGQG

TTLNNVHSNDTVHDRTPYRTLLMNELGVPFHLGTKQVCIAWSSSSCHDGK

AWLHVCVTGDDENATASFIYNGRLVDSIVSWSKKILRTQESECVCINGTC

TVVMTDGSASGKADTKILFIEEGKIVHTSTLSGSAQHVEECSCYPRYPGV

RCVCRDNWKGSNRPIVDINIKDYSIVSSYVCSGLVGDTPRKNDSSSSSHC

LDPNNEEGGHGVKGWAFDDGNDVWMGRTISEKLRSGYETFKVIEGWSNPN

SKLQINRQVIVDRGNRSGYSGIFSVEGKSCTNRCFYVELIRGRKQETEVL

WTSNSIVVFCGTSGTYGTGSWPDGADINLMPI

While sequences of exemplary influenza antigens are provided herein, and domains depicted for each of HA and NA and M2 have been provided for exemplary strains, it will be appreciated that any sequence having immunogenic characteristics of a domain of HA and/or NA and/or M2 may alternatively be employed. One skilled in the art will readily be capable of generating sequences having at least 75%, 80%, 85%, or 90% or more identity to provided antigens. In certain embodiments, influenza antigens comprise proteins including those having at least 95%, 96%, 97%, 98%, or more identity to a domain of HA and/or NA and/or M2, or a portion of a domain of HA and/or NA and/or M2, wherein the antigen protein retains immunogenic activity. For example sequences having sufficient identity to influenza antigen(s) which retain immunogenic characteristics are capable of binding with antibodies which react with domains (antigen(s)) provided herein. Immunogenic characteristics often include three dimensional presentation of relevant amino acids or side groups. One skilled in the art can readily identify sequences with modest differences in sequence (e.g., with difference in boundaries and/or some sequence alternatives, that, nonetheless preserve immunogenic characteristics). For instance, sequences whose boundaries are near to (e.g., within about 15 amino acids, 14 amino acids, 13 amino acids, 12 amino acids, 11 amino acids, 10 amino acids, 9 amino acids, 8 amino acids, 7 amino acids 6 amino acids, 5 amino acids 4 amino acids, 3 amino acids, 2 amino acids, or 1 amino acid) of domain boundaries designated herein at either end of designated amino acid sequence may be considered to comprise relevant domain in accordance with the present invention. Thus, the invention contemplates use of a sequence of influenza antigen to comprise residues approximating the domain designation. For example, domain(s) of HA have been engineered and expressed as an in-frame fusion protein as an antigen of the invention (see Exemplification herein). Further, one will appreciate that any domains, partial domains or regions of amino acid sequence of influenza antigen (e.g., HA, NA, M2) which are immunogenic can be generated using constructs and methods provided herein. Still further, domains or sub-domains can be combined, separately and/or consecutively for production of influenza antigens.

As exemplary antigens, we have utilized sequences from hemagglutinin, neuraminidase, and M2 of particular subtypes as described in detail herein. Various subtypes of influenza virus exist and continue to be identified as new subtypes emerge. It will be understood by one skilled in the art that the methods and compositions provided herein may be adapted to utilize sequences of additional subtypes. Such variation is contemplated and encompassed within the methods and compositions provided herein.

Influenza Polypeptide Fusions with Thermostable Proteins

In certain aspects of the invention, provided are influenza antigen(s) comprising fusion polypeptides which comprise an influenza protein (or a fragment or variant thereof) operably linked to a thermostable protein. Inventive fusion polypeptides can be produced in any available expression system known in the art. In certain embodiments, inventive fusion proteins are produced in a plant or portion thereof (e.g., plant, plant cell, root, sprout, etc.).

Enzymes or other proteins which are not found naturally in humans or animal cells are particularly appropriate for use in fusion polypeptides of the present invention. Thermostable proteins that, when fused, confer thermostability to a fusion product are useful. Thermostability allows produced protein to maintain conformation, and maintain produced protein at room temperature This feature facilitates easy, time efficient and cost effective recovery of a fusion polypeptide. A representative family of thermostable enzymes useful in accordance with the invention is the glucanohydrolase family. These enzymes specifically cleave 1,4-β glucosidic bonds that are adjacent to 1,3-β linkages in mixed linked polysaccharides (Hahn et al., 1994 *Proc. Natl. Acad. Sci., USA*, 91:10417). Such enzymes are found in cereals, such as oat and barley, and are also found in a number of fungal and bacterial species, including *C. thermocellum* (Goldenkova et al., 2002, *Mol. Biol.* 36:698). Thus, desirable thermostable proteins for use in fusion polypeptides of the present invention include glycosidase enzymes. Exemplary thermostable glycosidase proteins include those represented by GenBank accession numbers selected from those set forth in Table A, the contents of each of which are incorporated herein by reference by entire incorporation of the GenBank accession information for each referenced number. Exemplary thermostable enzymes of use in fusion proteins of the invention include *Clostridium thermocellum* P29716, *Brevibacillus brevis* P37073, and *Rhodthermus marinus* P45798, each of which are incorporated herein by reference to their GenBank accession numbers. Representative fusion proteins illustrated in the Examples utilize modified thermostable enzyme isolated from *Clostridium thermocellum*, however, any thermostable protein may be similarly utilized in accordance with the present invention.

TABLE A

Thermostable glycosidase proteins

| | |
|---|---|
| P29716 | (Beta-glucanase *Clostridium thermocellum*) |
| P37073 | (Beta-glucanase *Brevibacillus brevis*) |
| 1MVE_A | (Beta-glucanase *Fibrobacter succinogenes*) |
| P07883 | (Extracellular agarase *Streptomyces coelicolor*) |
| P23903 | (Glucan endo-13-beta-glucosidase A1 *Bacillus circulans*) |
| P27051 | (Beta-glucanase *Bacillus licheniformis*) |
| P45797 | (Beta-glucanase *Paenibacillus polymyxa* (*Bacillus polymyxa*)) |
| P37073 | (Beta-glucanase *Brevibacillus brevis*) |
| P45798 | (Beta-glucanase *Rhodothermus marinus*) |
| P38645 | (Beta-glucosidase *Thermobispora bispora*) |
| P40942 | (Celloxylanase *Clostridium stercorarium*) |
| P14002 | (Beta-glucosidase *Clostridium thermocellum*) |
| O33830 | (Alpha-glucosidase *Thermotoga maritima*) |
| O43097 | (Xylanase *Thermomyces lanuginosus*) |
| P54583 | (Endo-glucanase E1 *Acidothermus cellulolyticus*) |
| P14288 | (Beta-galactosidase *Sulfolobus acidocaldarius*) |
| O52629 | (Beta-galactosidase *Pyrococcus woesei*) |
| P29094 | (Oligo-1-6-glucosidase *Geobacillus thermoglucosidasius*) |
| P49067 | (Alpha-amylase *Pyrococcus furiosus*) |
| JC7532 | (Cellulase *Bacillus species*) |
| Q60037 | (Xylanase A *Thermotoga maritima*) |
| P33558 | (Xylanase A *Clostridium stercorarium*) |
| P05117 | (Polygalacturonase-2 precursor *Solanum lycopersicum*) |
| P04954 | (Cellulase D *Clostridium thermocellum*) |
| Q4J929 | (N-glycosylase *Sulfolobus acidocaldarius*) |
| O33833 | (Beta-fructosidase *Thermotoga maritima*) |
| P49425 | (Endo-14-beta-mannosidase *Rhodothermus marinus*) |
| P06279 | (Alpha-amylase *Geobacillus stearothermophilus*) |
| P45702 | (Xylanase *Geobacillus stearothermophilus*) |
| P45703 | |
| P40943 | |
| P09961 | (Alpha-amylase 1 *Dictyoglomus thermophilum*) |
| Q60042 | (Xylanase A *Thermotoga neapolitana*) |
| AAN05438 | (Beta-glycosidase *Thermus thermophilus*) |
| AAN05439 | |
| AAN05437 | (Sugar permease *Thermus thermophilus*) |
| AAN05440 | (Beta-glycosidase *Thermus filiformis*) |
| AAD43138 | (Beta-glycosidase *Thermosphaera aggregans*) |

When designing fusion proteins and polypeptides in accordance with the invention, it is desirable, of course, to preserve immunogenicity of the antigen. Still further, it is desirable in certain aspects of the invention to provide constructs which provide thermostability of a fusion protein. This feature facilitates easy, time efficient and cost effective recovery of a target antigen. In certain aspects, antigen fusion partners may be selected which provide additional advantages, including enhancement of immunogenicity, potential to incorporate multiple vaccine determinants, yet lack prior immunogenic exposure to vaccination subjects. Further beneficial qualities of fusion peptides of interest include proteins which provide ease of manipulation for incorporation of one or more antigens, as well as proteins which have potential to confer ease of production, purification, and/or formulation for vaccine preparations. One of ordinary skill in the art will appreciate that three dimensional presentation can affect each of these beneficial characteristics. Preservation of immunity or preferential qualities therefore may affect, for example, choice of fusion partner and/or choice of fusion location (e.g., N-terminus, C-terminus, internal, combinations thereof). Alternatively or additionally, preferences may affects length of segment selected for fusion, whether it be length of antigen, or length of fusion partner selected.

The present inventors have demonstrated successful fusion of a variety of antigens with a thermostable protein. For example, we have used the thermo-stable carrier molecule LicB, also referred to as lichenase, for production of fusion proteins. LicB is 1,3-1,4-β glucanase (LicB) from *Clostridium thermocellum* (GenBank accession: X63355 [gi: 40697]). LicB belongs to a family of globular proteins. Based on the three dimensional structure of LicB, its N- and C-termini are situated close to each other on the surface, in close proximity to the active domain. LicB also has a loop structure exposed on the surface that is located far from the active domain. We have generated constructs such that the loop structure and N- and C-termini of protein can be used as insertion sites for influenza antigen polypeptides. Influenza antigen polypeptides can be expressed as N- or C-terminal fusions or as inserts into the surface loop. Importantly, LicB maintains its enzymatic activity at low pH and at high temperature (up to 75° C.). Thus, use of LicB as a carrier molecule contributes advantages, including likely enhancement of target specific immunogenicity, potential to incorporate multiple vaccine determinants, and straightforward formulation of vaccines that may be delivered nasally, orally or parenterally. Furthermore, production of LicB fusions in plants should reduce the risk of contamination with animal or human pathogens. See examples provided herein.

Fusion proteins of the invention comprising influenza antigen may be produced in any of a variety of expression systems, including both in vitro and in vivo systems. One skilled in the art will readily appreciate that optimization of nucleic acid sequences for a particular expression system is often desirable. For example, in the exemplification provided herein, optimized sequence for expression of influenza antigen-LicB fusions in plants is provided. See Example 1. Thus, any relevant nucleic acid encoding influenza antigen(s) fusion protein(s) and fragments thereof in accordance with the invention is intended to be encompassed within nucleic acid constructs of the invention.

For production in plant systems, transgenic plants expressing influenza antigen(s) (e.g., influenza protein(s) or fragments or fusions thereof) may be utilized. Alternatively or additionally, transgenic plants may be produced using methods well known in the art to generate stable production crops. Additionally, plants utilizing transient expression systems may be utilized for production of influenza antigen(s). When utilizing plant expression systems, whether transgenic or transient expression in plants is utilized, any of nuclear expression, chloroplast expression, mitochondrial expression, or viral expression may be taken advantage of according to the applicability of the system to antigen desired. Furthermore, additional expression systems for production of antigens and fusion proteins in accordance with the present invention may be utilized. For example, mammalian expression systems (e.g., mammalian cell lines (e.g., CHO, etc.)), bacterial expression systems (e.g., *E. coli*), insect expression systems (e.g., baculovirus), yeast expression systems, and in vitro expression systems (e.g., reticulate lysates) may be used for expression of antigens and fusion proteins of the invention.

Production of Influenza Antigens

In accordance with the present invention, influenza antigens (including influenza protein(s), fragments, variants, and/or fusions thereof) may be produced in any desirable system; production is not limited to plant systems. Vector constructs and expression systems are well known in the art and may be adapted to incorporate use of influenza antigens provided herein. For example, influenza antigens (including fragments, variants, and/or fusions) can be produced in known expression systems, including mammalian cell systems, transgenic animals, microbial expression systems, insect cell systems, and plant systems, including transgenic and transient plant systems. Particularly where influenza antigens are produced as fusion proteins, it may be desirable to produce such fusion proteins in non-plant systems.

In some embodiments of the invention, influenza antigens are desirably produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Moreover, plants are not subject to contamination with animal pathogens. Like liposomes and microcapsules, plant cells are expected to provide protection for passage of antigen to the gastrointestinal tract.

Plants may be utilized for production of heterologous proteins via use of various production systems. One such system includes use of transgenic/genetically-modified plants where a gene encoding target product is permanently incorporated into the genome of the plant. Transgenic systems may generate crop production systems. A variety of foreign proteins, including many of mammalian origin and many vaccine candidate antigens, have been expressed in transgenic plants and shown to have functional activity. (Tacket et al., 2000, *J. Infect. Dis.*, 182:302; and Thanavala et al., 2005, *Proc. Natl. Acad. Sci., USA,* 102:3378). Additionally, administration of unprocessed transgenic plants expressing hepatitis B major surface antigen to non-immunized human volunteers resulted in production of immune response (Kapusta et al., 1999, *FASEB J,* 13:1796).

One system for expressing polypeptides in plants utilizes plant viral vectors engineered to express foreign sequences (e.g., transient expression). This approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of vaccine candidates, since the particulate nature of a vaccine candidate facilitates easy and cost-effective recovery from plant tissue. Additional advantages include enhanced target-specific immunogenicity, the potential to incorporate multiple vaccine determinants, and ease of formulation into vaccines that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA,* 95:2481; and Yusibov et al., 2002, *Vaccine,* 19/20:3155).

Plant Expression Systems

Any plant susceptible to incorporation and/or maintenance of heterologus nucleic acid and capable of producing heterologous protein may be utilized in accordance with the present invention. In general, it will often be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they may be grown outside without concern that expressed polynucleotide may be undesirably ingested. In some embodiments, however, it will be desirable to employ edible plants. In particular embodiments, it will be desirable to utilize plants that accumulate expressed polypeptides in edible portions of a plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish relevant modification (e.g., a particular glycosylation) may direct selection. For example, plants are capable of accomplishing certain post-translational modifications (e.g., glycosylation), however, plants will not generate sialation patterns which is found in mammalian post-translational modification. Thus, plant production of antigen may result in production of a different entity than the identical protein sequence produced in alternative systems.

In certain embodiments of the invention, crop plants, or crop-related plants are utilized. In certain specific embodiments, edible plants are utilized.

Plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. In certain aspects, plants of the invention may be plants of the *Brassica* or *Arabidopsis* genus. Some exemplary Brassicaceae family members include *Brassica campestris, B. carinata, B. juncea, B. napus, B. nigra, B. oleraceae, B. tournifortii, Sinapis alba*, and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Introducing Vectors into Plants In general, vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

A wide variety of viruses are known that infect various plant species, and can be employed for polynucleotide expression according to the present invention (see, for example, in *The Classification and Nomenclature of Viruses*, "Sixth Report of the International Committee on Taxonomy of Viruses" (Ed. Murphy et al.), Springer Verlag: New York, 1995, the entire contents of which are incorporated herein by reference; Grierson et al., *Plant Molecular Biology*, Blackie, London, pp. 126-146, 1984; Gluzman et al., *Communications in Molecular Biology: Viral Vectors*, Cold Spring Harbor Laboratory, Cold Spring Harbor, N.Y., pp. 172-189, 1988; and Mathew, *Plant Viruses Online* (http://image.fs.uidaho.edu/vide/). In certain embodiments of the invention rather than delivering a single viral vector to a plant cell, multiple different vectors are delivered which, together, allow for replication (and, optionally cell-to-cell and/or long distance movement) of viral vector(s). Some or all of the proteins may be encoded by the genome of transgenic plants. In certain aspects, described in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication 2005/0026291, both of which are incorporated herein by reference. As noted herein, in particular aspects of the present invention, viral vectors are applied to plants (e.g., plant, portion of plant, sprout, etc.), for example, through infiltration or mechanical inoculation, spray, etc. Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase.

In certain embodiments of the invention rather than introducing a single viral vector type into a plant, multiple different viral vectors are introduced. Such vectors may, for example, trans-complement each other with respect to functions such as replication, cell-to-cell movement, and/or long distance movement. Vectors may contain different polynucleotides encoding influenza antigen of the invention. Selection for plant(s) or portions thereof that express multiple polypeptides encoding one or more influenza antigen(s) may be performed as described above for single polynucleotides or polypeptides.

Plant Tissue Expression Systems

As discussed above, in accordance with the present invention, influenza antigens may be produced in any desirable system. Vector constructs and expression systems are well known in the art and may be adapted to incorporate use of influenza antigens provided herein. For example, transgenic plant production is known and generation of constructs and plant production may be adapted according to known techniques in the art. In some embodiments, transient expression systems in plants is desirable. Two of these systems include production of clonal roots and clonal plant systems, and derivatives thereof, as well as production of sprouted seedlings systems.

Clonal Plants

Clonal roots maintain RNA viral expression vectors and stably produce target protein uniformly in an entire root over extended periods of time and multiple subcultures. In contrast to plants, where a target gene is eliminated via recombination during cell-to-cell or long distance movement, in root cultures the integrity of a viral vector is maintained and levels of target protein produced over time are similar to those observed during initial screening. Clonal roots allow for ease of production of heterologous protein material for oral formulation of antigen and vaccine compositions. Methods and reagents for generating a variety of clonal entities derived from plants which are useful for production of antigen (e.g., antigen proteins of the invention) have been described previously and are known in the art (see, for example, PCT Publication WO 05/81905, which is incorporated herein by reference). Clonal entities include clonal root lines, clonal root cell lines, clonal plant cell lines, and clonal plants capable of production of antigen (e.g., antigen proteins of the invention). The invention further provides methods and reagents for expression of antigen polynucleotide and polypeptide products in clonal cell lines derived from various plant tissues (e.g., roots, leaves), and in whole plants derived from single cells (clonal plants). Such methods are typically based on use of plant viral vectors of various types.

For example, in one aspect, the invention provides methods of obtaining a clonal root line that expresses a polynucleotide encoding an influenza antigen of the invention comprising steps of: (i) introducing a viral vector that comprises a polynucleotide encoding an influenza antigen of the invention into a plant or portion thereof, and (ii) generating one or more clonal root lines from a plant. Clonal root lines may be generated, for example, by infecting a plant or plant portion (e.g., a harvested piece of leaf) with an *Agrobacterium* (e.g., *A. rhizogenes*) that causes formation of hairy roots. Clonal root lines can be screened in various ways to identify lines that maintain virus, lines that express a polynucleotide encoding an influenza antigen of the invention at high levels, etc. The invention further provides clonal root lines, e.g., clonal root lines produced according to inventive methods and further encompasses methods of expressing polynucleotides and producing polypeptide(s) encoding influenza antigen(s) of the invention using clonal root lines.

The invention further provides methods of generating a clonal root cell line that expresses a polynucleotide encoding an influenza antigen of the invention comprising steps of: (i) generating a clonal root line, cells of which contain a viral vector whose genome comprises a polynucleotide encoding an influenza antigen of the invention; (ii) releasing individual cells from a clonal root line; and (iii) maintaining cells under conditions suitable for root cell proliferation. The invention provides clonal root cell lines and methods of expressing polynucleotides and producing polypeptides using clonal root cell lines.

In one aspect, the invention provides methods of generating a clonal plant cell line that expresses a polynucleotide encoding an influenza antigen of the invention comprising steps of: (i) generating a clonal root line, cells of which contain a viral vector whose genome comprises a polynucleotide encoding an influenza antigen of the invention; (ii) releasing individual cells from a clonal root line; and (iii) maintaining cells in culture under conditions appropriate for plant cell proliferation. The invention further provides methods of generating a clonal plant cell line that expresses a polynucleotide encoding an influenza antigen of the invention comprising steps of: (i) introducing a viral vector that comprises a polynucleotide encoding an influenza antigen of the invention into cells of a plant cell line maintained in culture; and (ii) enriching for cells that contain viral vector. Enrichment may be performed, for example, by (i) removing a portion of cells from the culture; (ii) diluting removed cells so as to reduce cell concentration; (iii) allowing diluted cells to proliferate; and (iv) screening for cells that contain viral vector. Clonal plant cell lines may be used for production of an influenza antigen in accordance with the present invention.

The invention includes a number of methods for generating clonal plants, cells of which contain a viral vector that comprises a polynucleotide encoding influenza antigen of the invention. For example, the invention provides methods of generating a clonal plant that expresses a polynucleotide encoding influenza antigen of the invention comprising steps of: (i) generating a clonal root line, cells of which contain a viral vector whose genome comprises a polynucleotide encoding influenza antigen of the invention; (ii) releasing individual cells from a clonal root line; and (iii) maintaining released cells under conditions appropriate for formation of a plant. The invention further provides methods of generating a clonal plant that expresses a polynucleotide encoding influenza antigen of the invention comprising steps of: (i) generating a clonal plant cell line, cells of which contain a viral vector whose genome comprises a polynucleotide encoding an influenza antigen of the invention; and (ii) maintaining cells under conditions appropriate for formation of a plant. In general, clonal plants according to the invention can express any polynucleotide encoding an influenza antigen of the invention. Such clonal plants can be used for production of a antigen polypeptide.

As noted above, the present invention provides systems for expressing a polynucleotide or polynucleotide(s) encoding influenza antigen(s) of the invention in clonal root lines, clonal root cell lines, clonal plant cell lines (e.g., cell lines derived from leaf, stem, etc.), and in clonal plants. A polynucleotide encoding an influenza antigen of the invention is introduced into an ancestral plant cell using a plant viral vector whose genome includes polynucleotide encoding an influenza antigen of the invention operably linked to (i.e., under control of) a promoter. A clonal root line or clonal plant cell line is established from a cell containing virus according to any of several techniques further described below. The plant virus vector or portions thereof can be introduced into a plant cell by infection, by inoculation with a viral transcript or infectious cDNA clone, by electroporation, by T-DNA mediated gene transfer, etc.

The following sections describe methods for generating clonal root lines, clonal root cell lines, clonal plant cell lines, and clonal plants that express a polynucleotide encoding an influenza antigen of the invention are then described. A "root line" is distinguished from a "root cell line" in that a root line produces actual rootlike structures or roots while a root cell line consists of root cells that do not form rootlike structures. Use of the term "line" is intended to indicate that cells of the line can proliferate and pass genetic information on to progeny cells. Cells of a cell line typically proliferate in culture without being part of an organized structure such as those found in an intact plant. Use of the term "root line" is intended to indicate that cells in the root structure can proliferate without being part of a complete plant. It is noted that the term "plant cell" encompasses root cells. However, to distinguish the inventive methods for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. Plant cells can be, for example, leaf, stem, shoot, flower part, etc. It is noted that seeds can be derived from clonal plants generated as derived herein. Such seeds may contain viral vector as will plants obtained from such seeds. Methods for obtaining seed stocks are well known in the art (see, for example, U.S Patent Publication 2004/093643).

Clonal Root Lines

The present invention provides systems for generating a clonal root line in which a plant viral vector is used to direct expression of a polynucleotide encoding an influenza antigen of the invention. One or more viral expression vector(s) including a polynucleotide encoding an influenza antigen of the invention operably linked to a promoter is introduced into a plant or a portion thereof according to any of a variety of known methods. For example, plant leaves can be inoculated with viral transcripts. Vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

Where infection is to be accomplished by direct application of a viral genome to a plant, any available technique may be used to prepare viral genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily available, easy-to-use in vitro transcription systems (e.g., SP6, T7, reticulocyte lysate, etc.), and also the convenience of maintaining a DNA copy of an RNA vector, it is expected that inventive ssRNA vectors will often be prepared by in vitro transcription, particularly with T7 or SP6 polymerase. Infectious cDNA clones can be used. Agrobacterially mediated gene transfer can be used to transfer viral nucleic acids such as viral vectors (either entire viral genomes or portions thereof) to plant cells using, e.g., agroinfiltration, according to methods known in the art.

A plant or plant portion may then be then maintained (e.g., cultured or grown) under conditions suitable for replication of viral transcript. In certain embodiments of the invention virus spreads beyond the initially inoculated cell, e.g., locally from cell to cell and/or systemically from an initially inoculated leaf into additional leaves. However, in some embodiments of the invention virus does not spread. Thus viral vector may contain genes encoding functional MP and/or CP, but may be lacking one or both of such genes. In general, viral vector is introduced into (infects) multiple cells in the plant or portion thereof.

Following introduction of viral vector into a plant, leaves are harvested. In general, leaves may be harvested at any time following introduction of a viral vector. However, it may be desirable to maintain a plant for a period of time following introduction of a viral vector into the plant, e.g., a period of time sufficient for viral replication and, optionally, spread of virus from the cells into which it was initially introduced. A clonal root culture (or multiple cultures) is prepared, e.g., by known methods further described below.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, *Agrobacteria* can transfer DNA to a large and diverse set of plant types including numerous dicot and monocot angiosperm species and gymnosperms (see, for example, Gelvin, 2003, *Microbiol. Mol. Biol. Rev.,* 67:16, and references therein, all of which are incorporated herein by reference).

The molecular basis of genetic transformation of plant cells is transfer from bacterium and integration into plant nuclear genome of a region of a large tumor-inducing (Ti) or rhizogenic (Ri) plasmid that resides within various *Agrobacterial* species. This region is referred to as the T-region when present in the plasmid and as T-DNA when excised from plasmid. Generally, a single-stranded T-DNA molecule is transferred to a plant cell in naturally occurring *Agrobacterial* infection and is ultimately incorporated (in double-stranded form) into the genome. Systems based on Ti plasmids are widely used for introduction of foreign genetic material into plants and for production of transgenic plants.

Infection of plants with various *Agrobacterial* species and transfer of T-DNA has a number of effects. For example, *A. tumefaciens* causes crown gall disease while *A. rhizogenes* causes development of hairy roots at the site of infection, a condition known as "hairy root disease." Each root arises from a single genetically transformed cell. Thus root cells in roots are clonal, and each root represents a clonal population of cells. Roots produced by *A. rhizogenes* infection are characterized by a high growth rate and genetic stability (Giri et al., 2000, *Biotech. Adv.,* 18:1, and references therein, all of which are incorporated herein by reference). In addition, such roots are able to regenerate genetically stable plants (Giri 2000, supra).

In general, the present invention encompasses use of any strain of *Agrobacteria*, particularly *A. rhizogenes* strains, that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with *Agrobacteria* harboring the Ri plasmid, the invention encompasses use of alternative methods of introducing the relevant region into a plant cell. Such methods include any available method of introducing genetic material into plant cells including, but not limited to, biolistics, electroporation, PEG-mediated DNA uptake, Ti-based vectors, etc. The relevant portions of Ri T-DNA can be introduced into plant cells by use of a viral vector. Ri genes can be included in the same vector that contains a polynucleotide encoding an influenza antigen of the invention or in a different viral vector, which can be the same or a different type to that of the vector that contains a polynucleotide encoding an influenza antigen of the invention. It is noted that the entire Ri T-DNA may not be required for production of hairy roots, and the invention encompasses use of portions of Ri T-DNA, provided that such portions contain sufficient genetic material to induce root formation, as known in the art. Additional genetic material, e.g., genes present within the Ri plasmid but not within T-DNA, may be transferred to a plant cell in accordance with the invention, particularly genes whose expression products facilitate integration of T-DNA into the plant cell DNA.

In order to prepare a clonal root line in accordance with certain embodiments of the invention, harvested leaf portions are contacted with *A. rhizogenes* under conditions suitable for infection and transformation. Leaf portions are maintained in culture to allow development of hairy roots. Each root is clonal, i.e., cells in the root are derived from a single ancestral cell into which Ri T-DNA was transferred. In accordance with the invention, a portion of such ancestral cells will contain a viral vector. Thus cells in a root derived from such an ancestral cell may contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within the clonal root, movement of viral vector within the root is not necessary to maintain viral vector throughout the root. Individual clonal hairy roots may be removed from the leaf portion and further cultured. Such roots are also referred to herein as root lines. Isolated clonal roots continue to grow following isolation.

A variety of different clonal root lines have been generated using inventive methods. These root lines were generated using viral vectors containing polynucleotide(s) encoding an influenza antigen of the invention (e.g., encoding influenza polypeptide(s), or fragments or fusion proteins thereof). Root lines were tested by Western blot. Root lines displayed a variety of different expression levels of various polypeptides. Root lines displaying high expression were selected and further cultured. These root lines were subsequently tested again and shown to maintain high levels of expression over extended periods of time, indicating stability. Expression levels were comparable to or greater than expression in intact plants infected with the same viral vector used to generate clonal root lines. In addition, stability of expression of root lines was superior to that obtained in plants infected with the same viral vector. Up to 80% of such virus-infected plants reverted to wild type after 2-3 passages. (Such passages involved inoculating plants with transcripts, allowing infection (local or systemic) to become established, taking a leaf sample, and inoculating fresh plants that are subsequently tested for expression).

Root lines may be cultured on a large scale for production of antigen of the invention polypeptides as discussed further below. It is noted that clonal root lines (and cell lines derived from clonal root lines) can generally be maintained in medium that does not include various compounds, e.g., plant growth hormones such as auxins, cytokinins, etc., that are typically employed in culture of root and plant cells. This feature greatly reduces expense associated with tissue culture, and the inventors expect that it will contribute significantly to economic feasibility of protein production using plants.

Any of a variety of methods may be used to select clonal roots that express a polynucleotide encoding influenza antigen(s) of the invention. Western blots, ELISA assays, etc., can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., leaf material and/or roots derived therefrom can be cultured in the presence of an appropriate antibiotic or nutritional condition and surviving roots identified and isolated). Certain viral vectors contain two or more polynucleotide(s) encoding influenza antigen(s) of the invention, e.g., two or more polynucleotides encoding different polypeptides. If one of these is a selectable or detectable marker, clonal roots that are selected or detected by selecting for or detecting expression of the marker will have a high probability of also expressing a second polynucleotide. Screening for root lines that contain particular polynucleotides can also be performed using PCR and other nucleic acid detection methods.

Alternatively or additionally, clonal root lines can be screened for presence of virus by inoculating host plants that will form local lesions as a result of virus infection (e.g., hypersensitive host plants). For example, 5 mg of root tissue can be homogenized in 50 ul of phosphate buffer and used to inoculate a single leaf of a tobacco plant. If virus is present in root cultures, within two to three days characteristic lesions will appear on infected leaves. This means that root line contains recombinant virus that carries a polynucleotide encoding an influenza antigen of the invention (a target gene). If no local lesions are formed, there is no virus, and the root line is rejected as negative. This method is highly time and cost efficient. After initially screening for the presence of virus, roots that contain virus may be subjected to secondary screening, e.g., by Western blot or ELISA to select high expressers. Additional screens, e.g., screens for rapid growth, growth in particular media or under particular environmental conditions, etc., can be applied. These screening methods may, in general, be applied in the development of any of clonal root lines, clonal root cell lines, clonal plant cell lines, and/or clonal plants described herein.

As will be evident to one of ordinary skill in the art, a variety of modifications may be made to the description of the inventive methods for generating clonal root lines that contain a viral vector. Such modifications are within the scope of the invention. For example, while it is generally desirable to introduce viral vector into an intact plant or portion thereof prior to introduction of Ri T-DNA genes, in certain embodiments of the invention the Ri-DNA is introduced prior to introducing viral vector. In addition, it is possible to contact intact plants with *A. rhizogenes* rather than harvesting leaf portions and then exposing them to bacterium.

Other methods of generating clonal root lines from single cells of a plant or portion thereof that harbor a viral vector can be used (i.e., methods not using *A. rhizogenes* or genetic material from the Ri plasmid). For example, treatment with certain plant hormones or combinations of plant hormones is known to result in generation of roots from plant tissue.

Clonal Cell Lines Derived from Clonal Root Lines

As described above, the invention provides methods for generating clonal root lines, wherein cells in root lines contain a viral vector. As is well known in the art, a variety of different cell lines can be generated from roots. For example, root cell lines can be generated from individual root cells obtained from a root using a variety of known methods. Such root cell lines may be obtained from various different root cell types within the root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines containing viral vector. Such root cell lines therefore exhibit stable expression of a polynucleotide encoding an influenza antigen of the invention. Clonal plant cell lines can be obtained in a similar manner from clonal roots, e.g., by culturing dissociated root cells in the presence of appropriate plant hormones. Screens and successive rounds of enrichment can be used to identify cell lines that express a polynucleotide encoding an influenza antigen of the invention at high levels. However, if the clonal root line from which the cell line is derived already expresses at high levels, such additional screens may be unnecessary.

As in the case of the clonal root lines, cells of a clonal root cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal root cell line, movement of viral vector among cells is not necessary to maintain viral vector. Clonal root cell lines can be used for production of a polynucleotide encoding influenza antigen of the invention as described below.

Clonal Plant Cell Lines

The present invention provides methods for generating a clonal plant cell line in which a plant viral vector is used to direct expression of a polynucleotide encoding an influenza antigen of the invention. According to the inventive method, one or more viral expression vector(s) including a polynucleotide encoding an influenza antigen of the invention operably linked to a promoter is introduced into cells of a plant cell line that is maintained in cell culture. A number of plant cell lines from various plant types are known in the art, any of which can be used. Newly derived cell lines can be generated according to known methods for use in practicing the invention. A viral vector is introduced into cells of a plant cell line according to any of a number of methods. For example, protoplasts can be made and viral transcripts then electroporated into cells. Other methods of introducing a plant viral vector into cells of a plant cell line can be used.

A method for generating clonal plant cell lines in accordance with the invention and a viral vector suitable for introduction into plant cells (e.g., protoplasts) can be used as follows: Following introduction of viral vector, a plant cell line may be maintained in tissue culture. During this time viral vector may replicate, and polynucleotide(s) encoding an influenza antigen(s) of the invention may be expressed. Clonal plant cell lines are derived from culture, e.g., by a process of successive enrichment. For example, samples may be removed from culture, optionally with dilution so that the concentration of cells is low, and plated in Petri dishes in individual droplets. Droplets are then maintained to allow cell division.

It will be appreciated that droplets may contain a variable number of cells, depending on the initial density of the culture and the amount of dilution. Cells can be diluted such that most droplets contain either 0 or 1 cell if it is desired to obtain clonal cell lines expressing a polynucleotide encoding an influenza antigen of the invention after only a single round of enrichment. However, it can be more efficient to select a concentration such that multiple cells are present in each droplet and then screen droplets to identify those that contain expressing cells. In general, any appropriate screening procedure can be employed. For example, selection or detection of a detectable marker such as GFP can be used. Western blots or ELISA assays can be used. Individual droplets (100 ul) contain more than enough cells for performance of these assays. Multiple rounds of enrichment are performed to isolate successively higher expressing cell lines. Single clonal plant cell lines (i.e., populations derived from a single ancestral cell) can be generated by further limiting dilution using standard methods for single cell cloning. However, it is not necessary to isolate individual clonal lines. A population containing multiple clonal cell lines can be used for expression of a polynucleotide encoding one or more influenza antigen(s) of the invention.

In general, certain considerations described above for generation of clonal root lines apply to the generation of clonal plant cell lines. For example, a diversity of viral vectors containing one or more polynucleotide(s) encoding an influenza antigen(s) of the invention can be used as can combinations of multiple different vectors. Similar screening methods can be used. As in the case of clonal root lines and clonal root cell lines, cells of a clonal plant cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal plant cell line, movement of viral vector among cells is not necessary to maintain viral vector. The clonal plant cell line can be used for production of a polypeptide encoding an influenza antigen of the invention as described below.

Clonal Plants

Clonal plants can be generated from clonal roots, clonal root cell lines, and/or clonal plant cell lines produced according to various methods described above. Methods for the generation of plants from roots, root cell lines, and plant cell lines such as clonal root lines, clonal root cell lines, and clonal plant cell lines described herein are well known in the art (see, e.g., Peres et al., 2001, *Plant Cell, Tissue, Organ Culture,* 65:37; and standard reference works on plant molecular biology and biotechnology cited elsewhere herein). The invention therefore provides a method of generating a clonal plant comprising steps of (i) generating a clonal root line, clonal root cell line, or clonal plant cell line according to any of the inventive methods described above; and (ii) generating a whole plant from a clonal root line, clonal root cell line, or clonal plant. Clonal plants may be propagated and grown according to standard methods.

As in the case of clonal root lines, clonal root cell lines, and clonal plant cell lines, cells of a clonal plant are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within the clonal plant, movement of viral vector is not necessary to maintain viral vector.

Sprouts and Sprouted Seedling Plant Expression Systems

Systems and reagents for generating a variety of sprouts and sprouted seedlings which are useful for production of influenza antigen(s) according to the present invention have been described previously and are known in the art (see, for example, PCT Publication WO 04/43886, which is incorporated herein by reference). The present invention further provides sprouted seedlings, which may be edible, as a biomass containing an influenza antigen. In certain aspects, biomass is provided directly for consumption of antigen containing compositions. In some aspects, biomass is processed prior to consumption, for example, by homogenizing, crushing, drying, or extracting. In certain aspects, influenza antigen is purified from biomass and formulated into a pharmaceutical composition.

Additionally provided are methods for producing influenza antigen(s) in sprouted seedlings that can be consumed or harvested live (e.g., sprouts, sprouted seedlings of the *Brassica* genus). In certain aspects, the present invention involves growing a seed to an edible sprouted seedling in a contained, regulatable environment (e.g., indoors, in a container, etc.). A seed can be a genetically engineered seed that contains an expression cassette encoding an influenza antigen, which expression is driven by an exogenously inducible promoter. A variety of exogenously inducible promoters can be used that are inducible, for example, by light, heat, phytohormones, nutrients, etc.

In related embodiments, the present invention provides methods of producing influenza antigen(s) in sprouted seedlings by first generating a seed stock for a sprouted seedling by transforming plants with an expression cassette that encodes influenza antigen using an *Agrobacterium* transformation system, wherein expression of an influenza antigen is driven by an inducible promoter. Transgenic seeds can be obtained from a transformed plant, grown in a contained, regulatable environment, and induced to express an influenza antigen.

In some embodiments methods are provided that involves infecting sprouted seedlings with a viral expression cassette encoding an influenza antigen, expression of which may be driven by any of a viral promoter or an inducible promoter. Sprouted seedlings are grown for two to fourteen days in a contained, regulatable environment or at least until sufficient levels of influenza antigen have been obtained for consumption or harvesting.

The present invention further provides systems for producing influenza antigen(s) in sprouted seedlings that include a housing unit with climate control and a sprouted seedling containing an expression cassette that encodes one or more influenza antigens, wherein expression is driven by a constitutive or inducible promoter. Systems can provide unique advantages over the outdoor environment or greenhouse, which cannot be controlled. Thus, the present invention enables a grower to precisely time the induction of expression of influenza antigen. It can greatly reduce time and cost of producing influenza antigen(s).

In certain aspects, transiently transfected sprouts contain viral vector sequences encoding an inventive influenza antigen. Seedlings are grown for a time period so as to allow for production of viral nucleic acid in sprouts, followed by a period of growth wherein multiple copies of virus are produced, thereby resulting in production of influenza antigen(s).

In certain aspects, genetically engineered seeds or embryos that contain a nucleic acid encoding influenza antigen(s) are grown to sprouted seedling stage in a contained, regulatable environment. The contained, regulatable environment may be a housing unit or room in which seeds can be grown indoors. All environmental factors of a contained, regulatable environment may be controlled. Since sprouts do not require light to grow, and lighting can be expensive, genetically engineered seeds or embryos may be grown to sprouted seedling stage indoors in the absence of light.

Other environmental factors that can be regulated in a contained, regulatable environment of the present invention include temperature, humidity, water, nutrients, gas (e.g., $O_2$ or $CO_2$ content or air circulation), chemicals (small molecules such as sugars and sugar derivatives or hormones such as such as phytohormones gibberellic or absisic acid, etc.) and the like.

According to certain methods of the present invention, expression of a nucleic acid encoding an influenza antigen may be controlled by an exogenously inducible promoter. Exogenously inducible promoters are caused to increase or decrease expression of a nucleic acid in response to an external, rather than an internal stimulus. A number of environmental factors can act as inducers for expression of nucleic acids carried by expression cassettes of genetically engineered sprouts. A promoter may be a heat-inducible promoter, such as a heat-shock promoter. For example, using as heat-shock promoter, temperature of a contained environment may simply be raised to induce expression of a nucleic acid. Other promoters include light inducible promoters. Light-inducible promoters can be maintained as constitutive promoters if light in a contained regulatable environment is always on. Alternatively or additionally, expression of a nucleic acid can be turned on at a particular time during development by simply turning on the light. A promoter may be a chemically inducible promoter is used to induce expression of a nucleic acid. According to these embodiments, a chemical could simply be misted or sprayed onto seed, embryo, or seedling to induce expression of nucleic acid. Spraying and misting can be precisely controlled and directed onto target seed, embryo, or seedling to which it is intended. The contained environment is devoid of wind or air currents, which could disperse chemical away from intended target, so that the chemical stays on the target for which it was intended.

According to the present invention, time of expression is induced can be selected to maximize expression of an influenza antigen in sprouted seedling by the time of harvest. Inducing expression in an embryo at a particular stage of growth, for example, inducing expression in an embryo at a particular number of days after germination, may result in maximum synthesis of an influenza antigen at the time of harvest. For example, inducing expression from the promoter 4 days after germination may result in more protein synthesis than inducing expression from the promoter after 3 days or after 5 days. Those skilled in the art will appreciate that maximizing expression can be achieved by routine experimentation. In certain methods, sprouted seedlings are harvested at about 1, 2, 3, 4, 5, 6, 7, 8, 9, 10, 11, or 12 days after germination.

In cases where the expression vector has a constitutive promoter instead of an inducible promoter, sprouted seedling may be harvested at a certain time after transformation of sprouted seedling. For example, if a sprouted seedling were virally transformed at an early stage of development, for example, at embryo stage, sprouted seedlings may be harvested at a time when expression is at its maximum post-transformation, e.g., at about 1, 2, 3, 4, 5, 6, 7, 8, 9, 10, 11, 12, 13, or 14 days post-transformation. It could be that sprouts develop one, two, three or more months post-transformation, depending on germination of seed.

Generally, once expression of influenza antigen(s) begins, seeds, embryos, or sprouted seedlings are allowed to grow until sufficient levels of influenza antigen(s) are expressed. In certain aspects, sufficient levels are levels that would provide a therapeutic benefit to a patient if harvested biomass were eaten raw. Alternatively or additionally, sufficient levels are levels from which influenza antigen can be concentrated or purified from biomass and formulated into a pharmaceutical composition that provides a therapeutic benefit to a patient upon administration. Typically, influenza antigen is not a protein expressed in sprouted seedling in nature. At any rate, influenza antigen is typically expressed at concentrations above that which would be present in the sprouted seedling in nature.

Once expression of influenza antigen is induced, growth is allowed to continue until sprouted seedling stage, at which time sprouted seedlings are harvested. Sprouted seedlings can be harvested live. Harvesting live sprouted seedlings has several advantages including minimal effort and breakage. Sprouted seedlings of the present invention may be grown hydroponically, making harvesting a simple matter of lifting a sprouted seedling from its hydroponic solution. No soil is required for growth of sprouted seedlings of the invention, but may be provided if deemed necessary or desirable by the skilled artisan. Because sprouts can be grown without soil, no cleansing of sprouted seedling material is required at the time of harvest. Being able to harvest the sprouted seedling directly from its hydroponic environment without washing or scrubbing minimizes breakage of harvested material. Breakage and wilting of plants induces apoptosis. During apoptosis, certain proteolytic enzymes become active, which can degrade pharmaceutical protein expressed in the sprouted seedling, resulting in decreased therapeutic activity of the protein. Apoptosis-induced proteolysis can significantly decrease yield of protein from mature plants. Using methods of the present invention, apoptosis may be avoided when no harvesting takes place until the moment proteins are extracted from the plant.

For example, live sprouts may be ground, crushed, or blended to produce a slurry of sprouted seedling biomass, in a buffer containing protease inhibitors. Buffer may be maintained at about 4° C. In some aspects, sprouted seedling biomass is air-dried, spray dried, frozen, or freeze-dried. As in mature plants, some of these methods, such as air-drying, may result in a loss of activity of pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied to the present invention.

In some embodiments, sprouted seedlings are edible. In certain embodiments, sprouted seedlings expressing sufficient levels of influenza antigens are consumed upon harvesting (e.g., immediately after harvest, within minimal period following harvest) so that absolutely no processing occurs before sprouted seedlings are consumed. In this way, any harvest-induced proteolytic breakdown of influenza antigen before administration of influenza antigen to a patient in need of treatment is minimized. For example, sprouted seedlings that are ready to be consumed can be delivered directly to a patient. Alternatively or additionally, genetically engineered seeds or embryos are delivered to a patient in need of treatment and grown to sprouted seedling stage by a patient. In one aspect, a supply of genetically engineered sprouted seedlings are provided to a patient, or to a doctor who will be treating patients, so that a continual stock of sprouted seedlings expressing certain desirable influenza antigens may be cultivated. This may be particularly valuable for populations in developing countries, where expensive pharmaceuticals are not affordable or deliverable. The ease with which sprouted seedlings of the invention can be grown makes sprouted seedlings of the present invention particularly desirable for such developing populations.

The regulatable nature of the contained environment imparts advantages to the present invention over growing plants in the outdoor environment. In general, growing genetically engineered sprouted seedlings that express pharmaceutical proteins in plants provides a pharmaceutical product faster (because plants are harvested younger) and with less effort, risk, and regulatory considerations than growing genetically engineered plants. The contained, regulatable environment used in the present invention reduces or eliminates risk of cross-pollinating plants in nature.

For example, a heat inducible promoter likely would not be used outdoors because outdoor temperature cannot be controlled. The promoter would be turned on any time the outdoor temperature rose above a certain level. Similarly, the promoter would be turned off every time the outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that the maximum amount of expression can be achieved with every harvest.

In certain embodiments, sprouted seedlings of the present invention are grown in trays that can be watered, sprayed, or misted at any time during development of sprouted seedling. For example, a tray may be fitted with one or more watering, spraying, misting, and draining apparatus that can deliver and/or remove water, nutrients, chemicals etc. at specific time and at precise quantities during development of the sprouted seedling. For example, seeds require sufficient moisture to keep them damp. Excess moisture drains through holes in trays into drains in the floor of the room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings may be tightly stacked vertically on top of one another, providing a large quantity of biomass per unit floor space in a housing facility constructed specifically for these purposes. In addition, stacks of trays can be arranged in horizontal rows within the housing unit. Once seedlings have grown to a stage appropriate for harvest (about two to fourteen days) individual seedling trays are moved into a processing facility, either manually or by automatic means, such as a conveyor belt.

The system of the present invention is unique in that it provides a sprouted seedling biomass, which is a source of a influenza antigen(s). Whether consumed directly or processed into the form of a pharmaceutical composition, because sprouted seedlings are grown in a contained, regulatable environment, sprouted seedling biomass and/or pharmaceutical composition derived from biomass can be provided to a consumer at low cost. In addition, the fact that the conditions for growth of sprouted seedlings can be controlled makes the quality and purity of product consistent. The contained, regulatable environment of the invention obviates many safety regulations of the EPA that can prevent scientists from growing genetically engineered agricultural products out of doors.

Transformed Sprouts

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. Viral transformation is a more rapid and less costly method of transforming embryos and sprouted seedlings that can be harvested without an experimental or generational lag prior to obtaining desired product. For any of these techniques, the skilled artisan would appreciate how to adjust and optimize transformation protocols that have traditionally been used for plants, seeds, embryos, or spouted seedlings.

Agrobacterium Transformation Expression Cassettes

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by the *Agrobacterium* and catabolized by the plant. The bacterial genes responsible for expression of opines are a convenient source of control elements for chimeric expression cassettes. According to the present invention, *Agrobacterium* transformation system may be used to generate edible sprouted seedlings, which are merely harvested earlier than mature plants. *Agrobacterium* transformation methods can easily be applied to regenerate sprouted seedlings expressing influenza antigens.

In general, transforming plants involves transformation of plant cells grown in tissue culture by co-cultivation with an *Agrobacterium tumefaciens* carrying a plant/bacterial vector. The vector contains a gene encoding an influenza antigen. The *Agrobacterium* transfers vector to plant host cell and is then eliminated using antibiotic treatment. Transformed plant cells expressing influenza antigen are selected, differentiated, and finally regenerated into complete plantlets (Hellens et al., 2000, *Plant Mol. Biol.*, 42:819; Pilon-Smits et al., 1999, *Plant Physiolog.*, 119:123; Barfield et al., 1991, *Plant Cell Reports*, 10:308; and Riva et al., 1998, *J. Biotech.*, 1(3); each of which is incorporated by reference herein).

Expression vectors for use in the present invention include a gene (or expression cassette) encoding an influenza antigen designed for operation in plants, with companion sequences upstream and downstream of the expression cassette. Companion sequences are generally of plasmid or viral origin and provide necessary characteristics to the vector to transfer DNA from bacteria to the desired plant host.

The basic bacterial/plant vector construct may desirably provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may be present in the vector.

*Agrobacterium* T-DNA sequences are required for *Agrobacterium* mediated transfer of DNA to the plant chromosome. The tumor-inducing genes of T-DNA are typically removed and replaced with sequences encoding an influenza antigen. T-DNA border sequences are retained because they initiate integration of the T-DNA region into the plant genome. If expression of influenza antigen is not readily amenable to detection, the bacterial/plant vector construct may include a selectable marker gene suitable for determining if a plant cell has been transformed, e.g., nptII kanamycin resistance gene. On the same or different bacterial/plant vector (Ti plasmid) are Ti sequences. Ti sequences include virulence genes, which encode a set of proteins responsible for excision, transfer and integration of T-DNA into the plant genome (Schell, 1987, *Science*, 237:1176). Other sequences suitable for permitting integration of heterologous sequence into the plant genome may include transposon sequences, and the like, for homologous recombination.

Certain constructs will include an expression cassette encoding an antigen protein. One, two, or more expression cassettes may be used in a given transformation. The recombinant expression cassette contains, in addition to an influenza antigen encoding sequence, at least the following elements: a promoter region, plant 5' untranslated sequences, initiation codon (depending upon whether or not an expressed gene has its own), and transcription and translation termination sequences. In addition, transcription and translation terminators may be included in expression cassettes or chimeric genes of the present invention. Signal secretion sequences that allow processing and translocation of a protein, as appropriate, may be included in the expression cassette. A variety of promoters, signal sequences, and transcription and translation terminators are described, for example, in Lawton et al. (1987, *Plant Mol. Biol.*, 9:315) and in U.S. Pat. No. 5,888,789 (both of which are incorporated herein by reference). In addition, structural genes for antibiotic resistance are commonly utilized as a selection factor (Fraley et al. 1983, *Proc. Natl. Acad. Sci., USA*, 80:4803, incorporated herein by reference). Unique restriction enzyme sites at the 5' and 3' ends of a cassette allow for easy insertion into a pre-existing vector. Other binary vector systems for *Agrobacterium*-mediated transformation, carrying at least one T-DNA border sequence are described (PCT/EP99/07414, incorporated herein by reference).

Regeneration

Seeds of transformed plants may be harvested, dried, cleaned, and tested for viability and for the presence and expression of a desired gene product. Once this has been determined, seed stock is typically stored under appropriate conditions of temperature, humidity, sanitation, and security to be used when necessary. Whole plants may then be regenerated from cultured protoplasts, e.g., as described in Evans et al. (*Handbook of Plant Cell Cultures*, Vol. I; MacMillan Publishing Co., New York, N.Y., 1983, incorporated herein by reference); and in Vasil (ed., *Cell Culture and Somatic Cell Genetics of Plants*, Acad. Press, Orlando, Fla., Vol. I, 1984, and Vol. III, 1986, incorporated herein by reference). In certain aspects, plants are regenerated only to sprouted seedling stage. In some aspects, whole plants are regenerated to produce seed stocks and sprouted seedlings are generated from seeds of the seed stock.

All plants from which protoplasts can be isolated and cultured to give whole, regenerated plants can be transformed by the present invention so that whole plants are recovered that contain a transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Means for regeneration vary from one species of plants to the next. However, those skilled in the art will appreciate that generally a suspension of transformed protoplasts containing copies of a heterologous gene is first provided. Callus tissue is formed and shoots may be induced from callus and subsequently rooted. Alternatively or additionally, embryo formation can be induced from a protoplast suspension. These embryos germinate as natural embryos to form plants. Steeping seed in water or spraying seed with water to increase the moisture content of the seed to between 35-45% initiates germination. For germination to proceed, seeds are typically maintained in air saturated with water under controlled temperature and airflow conditions. The culture media will generally contain various amino acids and hormones, such as auxin and cytokinins. It is advantageous to add glutamic acid and proline to the medium, especially for such species as alfalfa. Shoots and roots normally develop simultaneously. Efficient regeneration will depend on the medium, the genotype, and the history of the culture. If these three variables are controlled, then regeneration is fully reproducible and repeatable.

The mature plants, grown from the transformed plant cells, are selfed and non-segregating, homozygous transgenic plants are identified. The inbred plant produces seeds containing inventive antigen-encoding sequences. Such seeds can be germinated and grown to sprouted seedling stage to produce influenza antigen(s) according to the present invention.

In related embodiments, seeds of the present invention may be formed into seed products and sold with instructions on how to grow seedlings to the appropriate sprouted seedling stage for administration or harvesting into a pharmaceutical composition. In some related embodiments, hybrids or novel varieties embodying desired traits may be developed from inbred plants of the invention.

Direct Integration

Direct integration of DNA fragments into the genome of plant cells by microprojectile bombardment or electroporation may be used in the present invention (see, e.g., Kikkert, et al., 1999, *Plant: J. Tiss. Cult. Assoc.,* 35:43; Bates, 1994, *Mol. Biotech.,* 2:135). More particularly, vectors that express influenza antigen(s) of the present invention can be introduced into plant cells by a variety of techniques. As described above, vectors may include selectable markers for use in plant cells. Vectors may include sequences that allow their selection and propagation in a secondary host, such as sequences containing an origin of replication and selectable marker. Typically, secondary hosts include bacteria and yeast. In one embodiment, a secondary host is bacteria (e.g., *Escherichia coli*, the origin of replication is a colE1-type origin of replication) and a selectable marker is a gene encoding ampicillin resistance. Such sequences are well known in the art and are commercially available (e.g., Clontech, Palo Alto, Calif. or Stratagene, La Jolla, Calif.).

Vectors of the present invention may be modified to intermediate plant transformation plasmids that contain a region of homology to an *Agrobacterium tumefaciens* vector, a T-DNA border region from *Agrobacterium tumefaciens*, and antigen encoding nucleic acids or expression cassettes described above. Further vectors may include a disarmed plant tumor inducing plasmid of *Agrobacterium tumefaciens.*

According to this embodiment, direct transformation of vectors invention may involve microinjecting vectors directly into plant cells by use of micropipettes to mechanically transfer recombinant DNA (see, e.g., Crossway, 1985, *Mol. Gen. Genet.,* 202:179, incorporated herein by reference). Genetic material may be transferred into a plant cell using polyethylene glycols (see, e.g., Krens et al., 1982, *Nature* 296:72). Another method of introducing nucleic acids into plants via high velocity ballistic penetration by small particles with a nucleic acid either within the matrix of small beads or particles, or on the surface (see, e.g., Klein et al., 1987, *Nature* 327:70; Knudsen et al., *Planta,* 185:330). Yet another method of introduction is fusion of protoplasts with other entities, either minicells, cells, lysosomes, or other fusible lipid-surfaced bodies (see, e.g., Fraley et al., 1982, *Proc. Natl. Acad. Sci., USA,* 79:1859). Vectors of the invention may be introduced into plant cells by electroporation (see, e.g., Fromm et al. 1985, *Proc. Natl. Acad. Sci., USA,* 82:5824). According to this technique, plant protoplasts are electroporated in the presence of plasmids containing a gene construct. Electrical impulses of high field strength reversibly permeabilize biomembranes allowing introduction of pasmids. Electroporated plant protoplasts reform the cell wall divide and form plant callus, which can be regenerated to form sprouted seedlings of the invention. Those skilled in the art will appreciate how to utilize these methods to transform plants cells that can be used to generate edible sprouted seedlings.

Viral Transformation

Similar to conventional expression systems, plant viral vectors can be used to produce full-length proteins, including full length antigen. According to the present invention, plant virus vectors may be used to infect and produce antigen(s) in seeds, embryos, sprouted seedlings, etc. Viral system that can be used to express everything from short peptides to large complex proteins. Specifically, using tobamoviral vectors is described, for example, by McCormick et al. (1999, *Proc. Natl. Acad. Sci., USA*, 96:703; Kumagai et al. 2000, *Gene*, 245:169; and Verch et al., 1998, *J. Immunol. Methods*, 220: 69; all of which are incorporated herein by reference). Thus, plant viral vectors have a demonstrated ability to express short peptides as well as large complex proteins.

In certain embodiments, transgenic sprouts, which express influenza antigen, are generated utilizing a host/virus system. Transgenic sprouts produced by viral infection provide a source of transgenic protein that has already been demonstrated to be safe. For example, sprouts are free of contamination with animal pathogens. Unlike, for example, tobacco, proteins from an edible sprout could at least in theory be used in oral applications without purification, thus significantly reducing costs. In addition, a virus/sprout system offers a much simpler, less expensive route for scale-up and manufacturing, since trangenes are introduced into virus, which can be grown up to a commercial scale within a few days. In contrast, transgenic plants can require up to 5-7 years before sufficient seeds or plant material are available for large-scale trials or commercialization.

According to the present invention, plant RNA viruses have certain advantages, which make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout the entire sprouted seedling (one to ten days post inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of the viral genes with desired sequence, by inserting foreign sequences into the virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

The genome of AlMV is a representative of the Bromoviridae family of viruses and consists of three genomic RNAs (RNAs 1-3) and subgenomic RNA (RNA4). Genomic RNAs 1 and 2 encode virus replicase proteins P1 and 2, respectively. Genomic RNA3 encodes cell-to-cell movement protein P3 and coat protein (CP). CP is translated from subgenomic RNA4, which is synthesized from genomic RNA3, and is required to start infection. Studies have demonstrated the involvement of CP in multiple functions, including genome activation, replication, RNA stability, symptom formation, and RNA encapsidation (see e.g., Bol et al., 1971, *Virology*, 46:73; Van Der Vossen et al., 1994, *Virology* 202:891; Yusibov et al., *Virology*, 208:405; Yusibov et al., 1998, *Virology*, 242:1; Bol et al., (Review, 100 refs.), 1999, *J. Gen. Virol.*, 80:1089; De Graaff, 1995, *Virology*, 208:583; Jaspars et al., 1974, *Adv. Virus Res.*, 19:37; Loesch-Fries, 1985, *Virology*, 146:177; Neeleman et al., 1991, *Virology*, 181:687; Neeleman et al., 1993, *Virology*, 196:883; Van Der Kuyl et al., 1991, *Virology*, 183:731; and Van Der Kuyl et al., 1991, *Virology*, 185:496).

Encapsidation of viral particles is typically required for long distance movement of virus from inoculated to un-inoculated parts of seed, embryo, or sprouted seedling and for systemic infection. According to the present invention, inoculation can occur at any stage of plant development. In embryos and sprouts, spread of inoculated virus should be very rapid. Virions of AlMV are encapsidated by a unique CP (24 kD), forming more than one type of particle. The size (30- to 60-nm in length and 18 nm in diameter) and shape (spherical, ellipsoidal, or bacilliform) of the particle depends on the size of the encapsidated RNA. Upon assembly, the N-terminus of AlMV CP is thought to be located on the surface of the virus particles and does not appear to interfere with virus assembly (Bol et al., 1971, *Virology*, 6:73). Additionally, ALMV CP with an additional 38-amino acid peptide at its N-terminus forms particles in vitro and retains biological activity (Yusibov et al., 1995, *J. Gen. Virol.*, 77:567).

AlMV has a wide host range, which includes a number of agriculturally valuable crop plants, including plant seeds, embryos, and sprouts. Together, these characteristics make ALMV CP an excellent candidate as a carrier molecule and AlMV an attractive candidate vector for expression of foreign sequences in a plant at the sprout stage of development. Moreover, upon expression from a heterologous vector such as TMV, AlMV CP encapsidates TMV genome without interfering with virus infectivity (Yusibov et al., 1997, *Proc. Natl. Acad. Sci., USA*, 94:5784, incorporated herein by reference). This allows use of TMV as a carrier virus for AlMV CP fused to foreign sequences.

TMV, the prototype of tobamoviruses, has a genome consisting of a single plus-sense RNA encapsidated with a 17.0 kD CP, which results in rod-shaped particles (300 nm in length). CP is the only structural protein of TMV and is required for encapsidation and long distance movement of virus in an infected host (Saito et al., 1990, *Virology* 176:329). 183 and 126 kD proteins are translated from genomic RNA and are required for virus replication (Ishikawa et al., 1986, *Nucleic Acids Res.*, 14:8291). 30 kD protein is the cell-to-cell movement protein of virus (Meshi et al., 1987, *EMBO J*, 6:2557). Movement and coat proteins are translated from subgenomic mRNAs (Hunter et al., 1976, *Nature*, 260:759; Bruening et al., 1976, *Virology*, 71:498; and Beachy et al., 1976, *Virology*, 73:498, each of which is incorporated herein by reference).

Other methods of transforming plant tissues include transforming the flower of a plant. Transformation of *Arabidopsis thaliana* can be achieved by dipping plant flowers into a solution of *Agrobacterium tumefaciens* (Curtis et al., 2001, *Transgenic Res.*, 10:363; and Qing et al., 2000, *Molecular Breeding New Strategies in Plant Improvement* 1:67). Transformed plants are formed in the population of seeds generated by "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al., 2000, *Plant Physiology*, 123:895). Transformed ovules follow the typical pathway of seed formation within the ovary.

Production and Isolation of Antigen

In general, standard methods known in the art may be used for culturing or growing plants, plant cells, and/or plant tissues of the invention (e.g., clonal plants, clonal plant cells, clonal roots, clonal root lines, sprouts, sprouted seedlings, plants, etc.) for production of antigen(s). A wide variety of culture media and bioreactors have been employed to culture hairy root cells, root cell lines, and plant cells (see, for example, Giri et al., 2000, *Biotechnol. Adv.*, 18:1; Rao et al., 2002, *Biotechnol. Adv.*, 20:101; and references in both of the foregoing, all of which are incorporated herein by reference). Clonal plants may be grown in any suitable manner.

In a certain embodiments, influenza antigens of the invention may be produced by any known method. In some embodiments, an influenza antigen is expressed in a plant or portion thereof. Proteins are isolated and purified in accordance with conventional conditions and techniques known in the art. These include methods such as extraction, precipitation, chromatography, affinity chromatography, electrophoresis, and the like. The present invention involves purification and affordable scaling up of production of influenza antigen(s) using any of a variety of plant expression systems known in the art and provided herein, including viral plant expression systems described herein.

In many embodiments of the present invention, it will be desirable to isolate influenza antigen(s) for vaccine products. Where a protein of the invention is produced from plant tissue(s) or a portion thereof, e.g., roots, root cells, plants, plant cells, that express them, methods described in further detail herein, or any applicable methods known in the art may be used for any of partial or complete isolation from plant material. Where it is desirable to isolate the expression product from some or all of plant cells or tissues that express it, any available purification techniques may be employed. Those of ordinary skill in the art are familiar with a wide range of fractionation and separation procedures (see, for example, Scopes et al., *Protein Purification: Principles and Practice,* 3$^{rd}$ Ed., Janson et al., 1993; *Protein Purification: Principles, High Resolution Methods, and Applications*, Wiley-VCH, 1998; Springer-Verlag, NY, 1993; and Roe, *Protein Purification Techniques*, Oxford University Press, 2001; each of which is incorporated herein by reference). Often, it will be desirable to render the product more than about 50%, 60%, 70%, 80%, 85%, 90%, 91%, 92%, 93%, 94%, 95%, 96%, 97%, 98%, or 99% pure. See, e.g., U.S. Pat. Nos. 6,740,740 and 6,841,659 for discussion of certain methods useful for purifying substances from plant tissues or fluids.

Those skilled in the art will appreciate that a method of obtaining desired influenza antigen(s) product(s) is by extraction. Plant material (e.g., roots, leaves, etc.) may be extracted to remove desired products from residual biomass, thereby increasing the concentration and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. The plant material can be disrupted by vigorous blending or grinding while suspended in buffer solution and extracted biomass removed by filtration or centrifugation. The product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

Vaccines

The present invention provides pharmaceutical antigen proteins for therapeutic use, such as influenza antigen(s) (e.g., influenza protein(s) or an immunogenic portion(s) thereof, or fusion proteins comprising influenza protein(s) or an immunogenic portion(s) thereof) active as a vaccine for therapeutic and/or prophylactic treatment of influenza infection. Further, the invention provides veterinary use, as such influenza antigen is active in veterinary applications. In certain embodiments, influenza antigen(s) may be produced by plant(s) or portion thereof (e.g., root, cell, sprout, cell line, plant, etc.) of the invention. In certain embodiments, provided influenza antigens are expressed in plants, plant cells, and/or plant tissues (e.g., sprouts, sprouted seedlings, roots, root culture, clonal cells, clonal cell lines, clonal plants, etc.), and can be used directly from plant or partially purified or purified in preparation for pharmaceutical administration to a subject.

The present invention provides plants, plant cells, and plant tissues expressing influenza antigen(s) that maintains pharmaceutical activity when administered to a subject in need thereof. Exemplary subjects include vertebrates (e.g., mammals such as humans). According to the present invention, subjects include veterinary subjects such as bovines, ovines, canines, felines, etc. In certain aspects, an edible plant or portion thereof (e.g., sprout, root) is administered orally to a subject in a therapeutically effective amount. In some aspects one or more influenza antigen(s) is provided in a pharmaceutical preparation, as described herein.

Vaccine compositions of the invention comprise one or more influenza antigens. In certain embodiments, at least two influenza antigens of the invention are included in an administered vaccine composition.

According to the present invention, treatment of a subject with an influenza antigen vaccine is intended to elicit a physiological effect. A vaccine protein may have healing curative or palliative properties against a disorder or disease and can be administered to ameliorate relieve, alleviate, delay onset of, reverse or lessen symptoms or severity of a disease or disorder. A vaccine comprising; an influenza antigen may have prophylactic properties and can be used to prevent or delay the onset of a disease or to lessen the severity of such disease, disorder, or pathological condition when it does emerge. A physiological effect elicited by treatment of a subject with antigen according to the present invention can include an effective immune response such that infection by an organism is thwarted.

In some embodiments, inventive vaccines are delivered by oral and/or mucosal routes. Oral and/or mucosal delivery has the potential to prevent infection of mucosal tissues, the primary gateway of infection for many pathogens. Oral and/or mucosal delivery can prime systemic immune response. There has been considerable progress in the development of heterologous expression systems for oral administration of antigens that stimulate the mucosal-immune system and can prime systemic immunity. Previous efforts at delivery of oral vaccine however, have demonstrated a requirement for considerable quantities of antigen in achieving efficacy. Thus, economical production of large quantities of target antigens is a prerequisite for creation of effective oral vaccines. The development of plants expressing antigens, including thermostable antigens, represents a more realistic approach to such difficulties.

The pharmaceutical preparations of the present invention can be administered in a wide variety of ways to a subject, such as, for example, orally, nasally, enterally, parenterally, intramuscularly or intravenously, rectally, vaginally, topically, ocularly, pulmonarily, or by contact application. In certain embodiments, an influenza antigen expressed in a plant or portion thereof is administered to a subject orally by direct administration of a plant to a subject. In some aspects a vaccine protein expressed in a plant or portion thereof is extracted and/or purified, and used for the preparation of a pharmaceutical composition. It may be desirable to formulate such isolated products for their intended use (e.g., as a pharmaceutical agent, vaccine composition, etc.). In some embodiments, it will be desirable to formulate products together with some or all of plant tissues that express them.

Where it is desirable to formulate product together with the plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments of the invention, it is desirable to have expressed influenza antigen in an edible plant (and, specifically in edible portions of the plant) so that the material can subsequently be eaten. For instance, where vaccine antigen is active after oral delivery (when properly formulated), it may be desirable to produce antigen protein in an edible plant portion, and to formulate expressed influenza antigen for oral delivery together with some or all of the plant material with which the protein was expressed.

Vaccine antigens (i.e., influenza antigens of the invention) provided may be formulated according to known techniques. For example, an effective amount of a vaccine product can be formulated together with one or more organic or inorganic, liquid or solid, pharmaceutically suitable carrier materials. A vaccine antigen produced according to the present invention may be employed in dosage forms such as tablets, capsules, troches, dispersions, suspensions, solutions, gelcaps, pills, caplets, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

In general, compositions may comprise any of a variety of different pharmaceutically acceptable carrier(s), adjuvant(s), or vehicle(s), or a combination of one or more such carrier(s), adjuvant(s), or vehicle(s). As used herein the language "pharmaceutically acceptable carrier, adjuvant, or vehicle" includes solvents, dispersion media, coatings, antibacterial and antifungal agents, isotonic and absorption delaying agents, and the like, compatible with pharmaceutical administration. Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can be present in the composition, according to the judgment of the formulator (see also *Remington's Pharmaceutical Sciences*, Fifteenth Edition, E. W. Martin, Mack Publishing Co., Easton, Pa., 1975). For example, vaccine antigen product may be provided as a pharmaceutical composition by means of conventional mixing granulating dragee-making, dissolving, lyophilizing, or similar processes.

Additional Vaccine Components

Inventive vaccines may include additionally any suitable adjuvant to enhance the immunogenicity of the vaccine when administered to a subject. For example, such adjuvant(s) may include, without limitation, extracts of *Quillaja saponaria* (QS), including purified subfractions of food grade QS such as Quil A and QS-21, alum, aluminum hydroxide, aluminum phosphate, MF59, Malp2, incomplete Freund's adjuvant; Complete freund's adjuvant; 3 De-O-acylated monophosphoryl lipid A (3D-MPL). Further adjuvants include immunomodulatory oligonucleotides, for example unmethylated CpG sequences as disclosed in WO 96/02555. Combinations of different adjuvants, such as those mentioned hereinabove, are contemplated as providing an adjuvant which is a preferential stimulator of TH1 cell response. For example, QS21 can be formulated together with 3D-MPL. The ratio of QS21:3 D-MPL will typically be in the order of 1:10 to 10:1; 1:5 to 5:1; and often substantially 1:1. The desired range for optimal synergy may be 2.5:1 to 1:1 3D-MPL: QS21. Doses of purified QS extracts suitable for use in a human vaccine formulation are from 0.01 mg to 10 mg per kilogram of bodyweight.

It should be noted that certain thermostable proteins (e.g., lichenase) may themselves demonstrate immunoresponse potentiating activity, such that use of such protein whether in a fusion with an influenza antigen or separately may be considered use of an adjuvant. Thus, inventive vaccine compositions may further comprise one or more adjuvants. Certain vaccine compositions may comprise two or more adjuvants. Furthermore, depending on formulation and routes of administration, certain adjuvants may be desired in particular formulations and/or combinations.

In certain situations, it may be desirable to prolong the effect of an inventive vaccine by slowing the absorption of one or more components of the vaccine product (e.g., protein) that is subcutaneously or intramuscularly injected. This may be accomplished by use of a liquid suspension of crystalline or amorphous material with poor water solubility. The rate of absorption of product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations may be prepared by entrapping product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid, etc., can be used. Antigen(s) or an immunogenic portions thereof may be formulated as microparticles, e.g., in combination with a polymeric delivery vehicle.

Enterally administered preparations of vaccine antigens may be introduced in solid, semi-solid, suspension or emulsion form and may be compounded with any pharmaceutically acceptable carriers, such as water, suspending agents, and emulsifying agents. Antigens may be administered by means of pumps or sustained-release forms, especially when administered as a preventive measure, so as to prevent the development of disease in a subject or to ameliorate or delay an already established disease. Supplementary active compounds, e.g., compounds independently active against the disease or clinical condition to be treated, or compounds that enhance activity of an inventive compound, can be incorporated into or administered with compositions. Flavorants and coloring agents can be used.

Inventive vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, extraction etc.), depending on the properties of the desired therapeutic product and its desired form. Such compositions as described above may be ingested orally alone or ingested together with food or feed or a beverage. Compositions for oral administration include plants; extractions of plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, plants may be air dried by placing them in a commercial air dryer at about 120 degrees Fahrenheit until biomass contains less than 5% moisture by weight. The dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. Dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

Inventive root lines, cell lines, plants, extractions, powders, dried preparations and purified protein or nucleic acid products, etc., can be in encapsulated form with or without one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms active agent may be mixed with at least one inert diluent such as sucrose, lactose or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally contain opacifying agents and can be of a composition that they release the active ingredient(s) only, or preferentially, in a certain part of the intestinal tract, and/or in a delayed manner. Examples of embedding compositions that can be used include polymeric substances and waxes.

In some methods, a plant or portion thereof expressing a influenza antigen according to the present invention, or biomass thereof, is administered orally as medicinal food. Such edible compositions are typically consumed by eating raw, if in a solid form, or by drinking, if in liquid form. The plant material can be directly ingested without a prior processing step or after minimal culinary preparation. For example, the vaccine protein may be expressed in a sprout which can be eaten directly. For instance, vaccine antigens expressed in an alfalfa sprout, mung bean sprout, or spinach or lettuce leaf sprout, etc. In one embodiment, plant biomass may be processed and the material recovered after the processing step is ingested.

Processing methods useful in accordance with the present invention are methods commonly used in the food or feed industry. The final products of such methods typically include a substantial amount of an expressed antigen and can be conveniently eaten or drunk. The final product may be mixed with other food or feed forms, such as salts, carriers, favor enhancers, antibiotics, and the like, and consumed in solid, semi-solid, suspension, emulsion, or liquid form. Such methods can include a conservation step, such as, e.g., pasteurization, cooking, or addition of conservation and preservation agents. Any plant may be used and processed in the present invention to produce edible or drinkable plant matter. The amount of influenza antigen in a plant-derived preparation may be tested by methods standard in the art, e.g., gel electrophoresis, ELISA, or Western blot analysis, using a probe or antibody specific for product. This determination may be used to standardize the amount of vaccine antigen protein ingested. For example, the amount of vaccine antigen may be determined and regulated, for example, by mixing batches of product having different levels of product so that the quantity of material to be drunk or eaten to ingest a single dose can be standardized. The contained, regulatable environment of the present invention, however, should minimize the need to carry out such standardization procedures.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, product may receive at least some protection from digestion in the upper digestive tract before reaching the gut or intestine and a higher proportion of active product would be available for uptake.

Pharmaceutical compositions of the present invention can be administered therapeutically or prophylactically. The compositions may be used to treat or prevent a disease. For example, any individual who suffers from a disease or who is at risk of developing a disease may be treated. It will be appreciated that an individual can be considered at risk for developing a disease without having been diagnosed with any symptoms of the disease. For example, if the individual is known to have been, or to be intended to be, in situations with relatively high risk of exposure to influenza infection, that individual will be considered at risk for developing the disease. Similarly, if members of an individual's family or friends have been diagnosed with influenza infection, the individual may be considered to be at risk for developing the disease.

Liquid dosage forms for oral administration include, but are not limited to, pharmaceutically acceptable emulsions, microemulsions, solutions, suspensions, syrups, and elixirs. In addition to active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents.

Compositions for rectal or vaginal administration may be suppositories or retention enemas, which can be prepared by mixing the compositions of this invention with suitable non-irritating excipients or carriers such as cocoa butter, polyethylene glycol or a suppository wax which are solid at ambient temperature but liquid at body temperature and therefore melt in the rectum or vaginal cavity and release the active protein.

Dosage forms for topical, transmucosal or transdermal administration of a vaccine composition of this invention include ointments, pastes, creams, lotions, gels, powders, solutions, sprays, inhalants or patches. The active agent, or preparation thereof, is admixed under sterile conditions with a pharmaceutically acceptable carrier and any needed preservatives or buffers as may be required. For transmucosal or transdermal administration, penetrants appropriate to the barrier to be permeated may be used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, antigen or a immunogenic portion thereof may be formulated into ointments, salves, gels, or creams as generally known in the art. Ophthalmic formulation, eardrops, and eye drops are contemplated as being within the scope of this invention. Additionally, the present invention contemplates the use of transdermal patches, which have the added advantage of providing controlled delivery of a vaccine protein to the body. Such dosage forms can be made by suspending or dispensing the vaccine product in the proper medium. Absorption enhancers can be used to increase the flux of the vaccine protein across the skin. The rate can be controlled by either providing a rate controlling membrane or by dispersing the vaccine protein in a polymer matrix or gel.

Inventive compositions are administered in such amounts and for such time as is necessary to achieve the desired result. In certain embodiments of the present invention a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., viral infection, influenza infection), etc.

The exact amount required may vary from subject to subject, depending on the species, age, and general condition of the subject, the stage of the disease, the particular pharmaceutical mixture, its mode of administration, and the like. Influenza antigens of the invention, including plants expressing antigen(s) and/or preparations thereof may be formulated in dosage unit form for ease of administration and uniformity of dosage. The expression "dosage unit form," as used herein, refers to a physically discrete unit of vaccine composition appropriate for the patient to be treated. It will be understood, however, that the total daily usage of the compositions of the present invention is typically decided by an attending physician within the scope of sound medical judgment. The specific therapeutically effective dose level for any particular patient or organism may depend upon a variety of factors including the severity or risk of infection; the activity of the specific compound employed; the specific composition employed; the age, body weight, general health, sex of the patient, diet of the patient, pharmacokinetic condition of the patient, the time of administration, route of administration, and rate of excretion of the specific antigen(s) employed; the duration of the treatment; drugs used in combination or coincidental with the vaccine composition employed; and like factors well known in the medical arts.

It will be appreciated that vaccine compositions of the present invention can be employed in combination therapies (e.g., combination vaccine therapies), that is, pharmaceutical compositions can be administered concurrently with, prior to, or subsequent to, one or more other desired pharmaceutical and/or vaccination procedures. The particular combination of therapies (e.g., vaccines, therapeutic treatment of influenza infection) to employ in a combination regimen will generally take into account compatibility of the desired therapeutics and/or procedures and the desired therapeutic effect to be achieved. It will be appreciated that the therapies and/or vaccines employed may achieve a desired effect for the same disorder (for example, an inventive antigen may be administered concurrently with another influenza vaccine), or they may achieve different effects.

In certain embodiments, vaccine compositions comprise at least two influenza antigens. For example, certain vaccine compositions can comprise at least two influenza antigens of the invention (e.g., a HA domain and an NA domain containing antigen of the invention). In some aspects such combination vaccines may include one thermostable fusion protein comprising influenza antigen; in some aspects, two or more thermostable fusion proteins comprising influenza antigen are provided.

Where combination vaccines are utilized, it will be understood that any combination of influenza antigens may be used for such combinations. Compositions may include multiple influenza antigens, including multiple antigens provided herein. Furthermore, compositions may include one or more antigens provided herein with one or more additional antigens. Combinations of influenza antigens include influenza antigens derived from one or more various subtypes or strains such that immunization confers immune response against more than one infection type. Combinations of influenza antigen may include at least one, at least two, at least three, at least four or more antigens derived from different subtypes or strains. In some combinations, at least two or at least three antigens from different subtypes are combined in one vaccine composition. Furthermore, combination vaccines may utilize influenza antigen and antigen from one or more unique infectious agents.

Kits

In one aspect, the present invention provides a pharmaceutical pack or kit including influenza antigens according to the present invention. In certain embodiments, pharmaceutical packs or kits include live sprouted seedlings, clonal entity or plant producing an influenza antigen according to the present invention, or preparations, extracts, or pharmaceutical compositions containing vaccine in one or more containers filled with optionally one or more additional ingredients of pharmaceutical compositions of the invention. In some embodiments, pharmaceutical packs or kits include pharmaceutical compositions comprising purified influenza antigen according to the present invention, in one or more containers optionally filled with one or more additional ingredients of pharmaceutical compositions of the invention. In certain embodiments, the pharmaceutical pack or kit includes an additional approved therapeutic agent (e.g., influenza antigen, influenza vaccine) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. As but one non-limiting example, influenza vaccine can be provided as oral formulations and administered as therapy. Alternatively or additionally, influenza vaccine can be provided in an injectable formulation for administration. In some embodiments, influenza vaccine can be provided in an inhalable formulation for administration. Pharmaceutical doses or instructions therefor may be provided in the kit for administration to an individual suffering from or at risk for influenza infection.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

EXEMPLIFICATION

Example 1

Generation of Vaccine Candidate Constructs

Generation of Antigen Sequences from Influenza Virus Hemagglutinin

Nucleotide sequence encoding HA stem domain (SD) 1-2 and HA globular domain (GD) 3 of each of influenza virus type Vietnam H5N1 and Wyoming H3N2 was synthesized and confirmed as being correct. Produced nucleic acid was digested with restriction endonucleases BglII/HindIII, sites for which had been engineered onto either end of sequence encoding domains. The resulting DNA fragments were fused in frame to sequence encoding an engineered thermostable carrier molecule.

```
HA Vietnam [H5N1]
(SD domain 1-2): HA1_2V: (SEQ ID NO.: 19):
AGATCTGATCAAATCTGCATTGGATACCACGCTAACAACTCTACTGAGCA

AGTGGATACAATTATGGAGAAGAACGTGACTGTTACTCACGCTCAGGATA

TTCTTGAAAAGACTCACAACGGAAAGTTGGGAGGAGGAAACACTAAGTGC

CAGACTCCAATGGGAGCTATTAACTCTTCTATGCCATTCCACAACATTCA

CCCACTTACTATTGGAGAGTGCCCAAAGTACGTGAAGTCTAACAGGCTTG

TGCTTGCTACTGGACTTAGGAATTCTCCACAAAGAGAGAGGAGAAGGAAG

AAGAGGGGACTTTTCGGAGCTATTGCTGGATTCATTGAGGGAGGATGGCA

AGGAATGGTTGATGGATGGTACGGATACCATCACTCTAATGAGCAGGGAT

CTGGATATGCTGCTGATAAGGAGTCTACTCAGAAGGCTATTGATGGAGTG

ACTAACAAGGTGAACTCTATTATTGATAAGATGAACACTCAGTTCGAAGC

TGTTGGAAGGGAGTTCAACAATCTTGAGAGGAGGATTGAGAACCTTAACA

AGAAAATGGAGGATGGATTCCTTGATGTGTGGACTTACAACGCTGAGCTT

CTTGTGCTTATGGAGAACGAGAGGACTCTTGATTTCCACGATTCTAACGT

GAAGAACCTTTACGACAAAGTGAGGCTTCAGCTTAGGGATAACGCTAAGG

AGCTTGGAAACGGTTGCTTCGAGTTCTACCACAAGTGCGATAATGAGTGC

ATGGAGTCTGTTAGGAACGGAACTTACGATTACCCACAGTACTCTGAGGA

AGCTAGACTTAAGAGGGAGGAGATTTCTGGAGTGAAGTTGGAGTCTATTG

GTATCTACCAGATTAAGCTT (SD domain 1-2): HA1_2V: (SEQ ID NO.: 20):
DQICIGYHANNSTEQVDTIMEKNVTVTHAQDILEKTHNGKLNTKCQTPMG

AINSSMPFHNIHPLTIGECPKYVKSNRLVLATGLRNSPQRERRRKKRGLF

GAIAGFIEGGWQGMVDGWYGYHHSNEQGSGYAADKESTQKAIDGVTNKVN

SIIDKMNTQFEAVGREFNNLERRIENLNKKMEDGFLDVWTYNAELLVLME

NERTLDFHDSNVKNLYDKVRLQLRDNAKELGNGCFEFYHKCDNECMESVR

NGTYDYPQYSEEARLKREEISGVKLESIGIYQI (GD domain 3): HA3V: (SEQ ID NO.: 21):
AGATCTTGCGATCTTGATGGAGTGAAGCCACTTATTCTTAGGGATTGCTC

TGTTGCTGGATGGCTTCTTGGAAACCCAATGTGCGATGAGTTCATTAACG

TGCCAGAGTGGTCTTATATTGTGGAGAAGGCTAAACCAGTGAACGATCTT

TGTTACCCAGGAGATTTCAACGATTACGAGGAGCTTAAGCACCTTCTTTC

TAGGATTAACCACTTCGAGAAGATTCAGATTATTCCAAAGTCATCTTGGT

CATCTCACGAGGCTTCTCTTGGAGTTTCTTCTGCTTGCCCATACCAGGGA

AAGTCATCTTTCTTCAGGAACGTTGTGTGGCTTATTAAGAAGAACTCTAC

TTACCCAACTATTAAGAGGTCTTACAACAACACTAACCAGGAGGATCTTC

TTGTGCTTTGGGGAATTCACCATCCAAATGATGCTGCTGAGCAGACTAAG

TTGTACCAGAACCCAACTACTTACATTTCTGTGGGAACTTCTACTCTTAA

CCAGAGGCTTGTGCCAAGAATTGCTACTAGGTCTAAGGTGAACGGACAAT

CTGGAAGGATGGAGTTCTTCTGGACTATTCTTAAGCCAAACGATGCTATT

AACTTCGAGTCTAACGGAAACTTCATTGCTCCAGAGTACGCTTACAAGAT

TGTGAAGAAGGGAGATTCTACTATTATGAAGTCTGAGCTTGAGTACGGAA

ACTGCAAGCTT
```

-continued (GD domain 3): HAV3: (SEQ ID NO.: 33):
CDLDGVKPLILRDCSVAGWLLGNPMCDEFINVPEWSYIVEKANPVNDLCY
PGDFNDYEELKHLLSRINHFEKIQIIPKSSWSSHEASLGVSSACPYQGKS
SFFRNVVWLIKKNSTYPTIKRSYNNTNQEDLLVLWGIHHPNDAAEQTKLY
QNPTTYISVGTSTLNQRLVPRIATRSKVNGQSGRMEFFWTILKPNDAINF
ESNGNFIAPEYAYKIVKKGDSTIMKSELEYGNC (full length): HA5V: (SEQ ID NO.: 22):
GGATCCATTAATTAAAATGGGATTCGTGCTTTTCTCTCAGCTTCCTTCTT
TCCTTCTTGTGTCTACTCTTCTTCTTTTCCTTGTGATTTCTCACTCTTGC
CGTGCTGATCAAATCTGCATTGGATACCACGCTAACAACTCTACTGAGCA
AGTGGATACAATTATGGAGAAGAACGTGACTGTTACTCACGCTCAGGATA
TTCTTGAAAAGACTCACAACGGAAAGTTGTGCGATCTTGATGGAGTGAAG
CCACTTATTCTTAGGGATTGCTCTGTTGCTGGATGGCTTCTTGGAAACCC
AATGTGCGATGAGTTCATTAACGTGCCAGAGTGGTCTTATATTGTGGAGA
AGGCTAACCCAGTTAATGATCTTTGCTACCCAGGAGATTTCAACGATTAC
GAGGAGCTTAAGCACCTTCTTTCTAGGATTAACCACTTCGAGAAGATTCA
GATTATTCCAAAGTCATCTTGGTCATCTCACGAGGCTTCTCTTGGAGTTT
CTTCTGCTTGCCCATACCAGGGAAAGTCATCTTTCTTCAGGAACGTTGTG
TGGCTTATTAAGAAGAACTCTACTTACCCAACTATTAAGAGGTCTTACAA
CAACACTAACCAGGAGGATCTTCTTGTGCTTTGGGGAATTCACCATCCAA
ATGATGCTGCTGAGCAGACTAAGTTGTACCAGAACCCAACTACTTACATT
TCTGTGGGAACTTCTACTCTTAACCAGAGGCTTGTGCCAAGAATTGCTAC
TAGGTCTAAGGTGAACGGACAATCTGGAAGGATGGAGTTCTTCTGGACTA
TTCTTAAGCCAAACGATGCTATTAACTTCGAGTCTAACGGAAACTTCATT
GCTCCAGAGTACGCTTACAAGATTGTGAAGAAGGGAGATTCTACTATTAT
GAAGTCTGAGCTTGAGTACGGAAACTGCAACACTAAGTGCCAAACTCCAA
TGGGAGCTATTAACTCTTCTATGCCATTCCACAACATTCACCCACTTACT
ATTGGAGAGTGCCCAAAGTACGTGAAGTCTAACAGGCTTGTGCTTGCTAC
TGGACTTAGGAATTCTCCACAAAGAGAGGAGGAGAAGGAAGAAGAGGGAC
TTTTCGGAGCTATTGCTGGATTCATTGAGGGAGGATGGCAAGGAATGGTT
GATGGATGGTACGGATACCATCACTCTAATGAGCAGGGATCTGGATATGC
TGCTGATAAGGAGTCTACTCAGAAGGCTATTGATGGAGTGACTAACAAGG
TGAACTCTATTATTGATAAGATGAACACTCAGTTCGAAGCTGTTGGAAGG
GAGTTCAACAATCTTGAGAGGAGGATTGAGAACCTTAACAAGAAAATGGA
GGATGGATTCCTTGATGTGTGGACTTACAACGCTGAGCTTCTTGTGTTGA
TGGAGAACGAGAGGACTCTTGATTTCCACGATTCTAACGTGAAGAACCTT
TACGACAAAGTGAGGCTTCAGCTTAGGGATAACGCTAAGGAGCTTGGAAA
CGGTTGCTTCGAGTTCTACCACAAGTGCGATAATGAGTGCATGGAGTCTG
TTAGGAACGGAACTTACGATTACCCACAGTACTCTGAGGAAGCTAGACTT
AAGAGGGAGGAGATTTCTGGAGTGAAGTTGGAGTCTATTGGTATCTACCA
GATTCACCATCACCATCACCACAAGGATGAGCTTTGATGACTCGAGCTC HA A/Wyoming (H3N2)
(SD domain 1-2): HA1_2W: (SEQ ID NO.: 23):
AGATCTCAAAAGTTGCCAGGAAACGATAACTCTACTGCTACTCTTTGCCT
TGGACATCACGCTGTTCCAAACGGAACTATTGTGAAAACTATTACTAACG
ATCAGATTGAGGTGACAAACGCTACTGAGCTTGTTCAGTCATCTTCTACT
GGAGGAATTGGAGGAGGAAACTCTGAGTGCATTACACCTAATGGATCTAT
TCCAAACGATAAGCCATTCCAGAACGTGAACAGGATTACTTATGGAGCTT
GCCCAAGATACGTGAAGCAGAACACTCTTAAGTTGGCTACTGGAATGAGG
AATGTGCCAGAGAAGCAGACTAGGGGAATTTTCGGAGCTATTGCTGGATT
CATTGAGAATGGATGGGAGGGAATGGTTGATGGATGGTACGGATTCAGGC
ATCAGAATTCTGAGGGAACTGGACAAGCTGCTGATCTTAAGTCTACTCAG
GCTGCTATTAACCAGATTAACGGAAAGTTGAACAGGCTTATTGGAAAGAC
TAACGAGAAGTTCCACCAGATTGAGAAGGAGTTCTCTGAGGTTGAGGGAA
GGATTCAGGATCTTGAGAAGTACGTGGAGGATACAAAGATTGATCTTTGG
TCTTACAACGCTGAGCTTCTTGTTGCTCTTGAGAACCAGCACACTATTGA
TCTTACTGATTCTGAGATGAACAAGTTGTTCGAGAGGACTAAGAAGCAGC
TTAGGGAGAACGCTGAGGATATGGGAAATGGATGCTTCAAAATCTACCAC
AAGTGCGATAACGCTTGCATTGAGTCTATTAGGAACGGAACTTACGATCA
CGATGTGTACCGTGATGAGGCTCTTAACAACAGGTTCCAGATTAAGGGAG
TGGAGCTTAAGTCTGGATACAAGGATTGGATTCTTAAGCTT (SD domain 1-2): HA1_2: (SEQ ID NO.: 24):
QKLPGNDNSTATLCLGHHAVPNGTIVKTITNDQIEVTNATELVQSSSTGG
TNSECITPNGSIPNDKPFQNVNRITYGAC*PRYVKQNTLKLA*TGMRNVPEK
QTRGIFGAIAGFIENGWEGMVDGWYGFRHQNSEGTGQAADLKSTQAAINQ
INGKLNRLIGKTNEKFHQIEKEFSEVEGRIQDLEKYVEDTKIDLWSYNAE
LLVALENQHTIDLTDSEMNKLFERTKKQLRENAEDMGNGCFKIYHKCDNA
CIESIRNGTYDHDVYRDEALNNRFQIKGVELKSGYKDWIL (GD domain 3): HA3W: (SEQ ID NO.: 25):
AGATCTTGCGATTCTCCACACCAGATTCTTGATGGAGAGAACTGCACTCT
TATTGATGCTCTTCTTGGAGATCCACAGTGCGATGGATTCCAGAACAAGA
AGTGGGATCTTTTCGTGGAAAGGTCTAAGGCTTACTCTAACTGCTACCCA
TACGATGTTCCAGATTACGCTTCTCTTAGGAGTCTTGTGGCTTCTTCTGG
AACTCTTGAGTTCAACAACGAGTCTTTCAACTGGGCTGGAGTTACTCAGA
ACGGAACTTCTTCTGCTTGTAAGAGGAGGTCTAACAAGTCTTTCTTCTCT
AGGCTTAACTGGCTTACTCACCTTAAGTACAAGTACCCAGCTCTTAACGT
GACTATGCCAAACAACGAGAAGTTCGATAAGTTGTACATTTGGGGAGTTC
ACCACCCAGTTACTGATTCTGATCAGATTTCTCTTTACGCTCAGGCTTCT
GGAAGGATTACTGTGTCTACTAAGAGGTCTCAGCAGACTGTGATTCCAAA
CATTGGATACCGTCCAAGAGTGAGGGATATTCTTAGGATTTCTATCT
ACTGGACTATTGTGAAGCCAGGAGATATTCTTCTTATTAACTCTACTGGA
AACCTTATTGCTCCAAGGGGATACTTCAAGATTAGGAGTGGAAAGTCATC
TATTATGAGGAGTGATGCTCCAATTGGAAAGTGCAAGCTT -continued (GDdomain 3): HA3W: (SEQ ID NO.: 12):
CDSPHQILDGENCTLIDALLGDPQCDGFQNKKWDLFVERSKAYSNC*PYD*
*VPDYA*SLRSLVASSGTLEFNNESFNWAGVTQNGTSSACKRRSNKSFFSRL
NWLTHLKYKYPALNVTMPNNEKFDKLYIWGVHHPVTDSDQISLYAQASGR
ITVSTKRSQQTVIPNIGYRPRVRDISSRISIYWTIVKPGDILLINSTGNL
IAPRGYFKIRSGKSSIMRSDAPIGKC (full length): HASW: (SEQ ID NO.: 26):
GGATCCATTAATTAAAATGGGATTCGTGCTTTTCTCTCAGCTTCCTTCTT
TCCTTCTTGTGTCTACTCTTCTTCTTTTCCTTGTGATTTCTCACTCTTGC
CGTGCTCAAAAGTTGCCAGGAAACGATAACTCTACTGCTACTCTTTGCCT
TGGACATCACGCTGTTCCAAACGGAACTATTGTGAAAACTATTACTAACG
ATCAGATTGAGGTGACAAACGCTACTGAGCTTGTTCAGTCATCTTCTACT
GGAGGAATTTGCGATTCTCCACACCAGATTCTTGATGGAGAGAACTGCAC
TCTTATTGATGCTCTTCTTGGAGATCCACAGTGCGATGGATTCCAGAACA
AGAAGTGGGATCTTTTCGTGGAAAGGTCTAAGGCTTACTCTAACTGCTAC
CCATACGATGTTCCAGATTACGCTTCTCTTAGGAGTCTTGTGGCTTCTTC
TGGAACTCTTGAGTTCAACAACGAGTCTTTCAACTGGGCTGGAGTTACTC
AGAACGGAACTTCTTCTGCTTGTAAGAGGAGGTCTAACAAGTCTTTCTTC
TCTAGGCTTAACTGGCTTACTCACCTTAAGTACAAGTACCCAGCTCTTAA
CGTGACTATGCCAAACAACGAGAAGTTCGATAAGTTGTACATTTGGGGAG
TTCACCACCCAGTTACTGATTCTGATCAGATTTCTCTTTACGCTCAGGCT
TCTGGAAGGATTACTGTGTCTACTAAGAGGTCTCAGCAGACTGTGATTCC
AAACATTGGATACCGTCCAAGAGTGAGGGATATTTCTTCTAGGATTTCTA
TCTACTGGACTATTGTGAAGCCAGGAGATATTCTTCTTATTAACTCTACT
GGAAACCTTATTGCTCCAAGGGGATACTTCAAGATTAGGAGTGGAAAGTC
ATCTATTATGAGGAGTGATGCTCCAATTGGAAAGTGCAACTCTGAGTGCA
TTACTCCAAACGGATCTATTCCAAACGATAAGCCATTCCAGAACGTGAAC
AGGATTACTTATGGAGCTTGCCCAAGATACGTGAAGCAGAACACTCTTAA
GTTGGCTACTGGAATGAGGAATGTGCCAGAGAAGCAGACTAGGGGAATTT
TCGGAGCTATTGCTGGATTCATTGAGAATGGATGGGAGGGAATGGTTGAT
GGATGGTACGGATTCAGGCACCAGAATTCAGAGGGAACTGGACAAGCTGC
TGATCTTAAGTCTACTCAGGCTGCTATTAACCAGATTAACGGAAAGTTGA
ACAGGCTTATTGGAAAGACTAACGAGAAGTTCCACCAGATTGAGAAGGAG
TTCTCTGAGGTTGAGGGAAGGATTCAGGATCTTGAGAAGTACGTGGAGGA
TACAAAGATTGATCTTTGGTCTTACAACGCTGAGCTTCTTGTTGCTCTTG
AGAACCAGCACACTATTGATTTGACTGATTCTGAGATGAACAAGTTGTTC
GAGAGGACTAAQAAGCAGCTTAGGGAGAACGCTGAGGATATGGGAAATGG
ATGCTTCAAAATCTACCACAAGTGCGATAACGCTTGCATTGAGTCTATTA
GGAACGGAACTTACGATCACGATGTGTACCGTGATGAGGCTCTTAACAAC
AGGTTCCAGATTAAGGGAGTGGAGCTTAAGTCTGGATACAAGGATTGGAT
TCTTCATCATCACCACCACCACAAGGATGAGCTTTGATGACTCGAGCTC

Generation of Antigen Sequences from Influenza Virus Neuraminidase

Nucleotide sequence encoding neuraminidase of each of influenza virus type Vietnam H5N1(NAV) and Wyoming H3N2(NAW) was synthesized and confirmed as being correct. Produced nucleic acid was digested with restriction endonuclease SalI, sites for which had been engineered onto either end of sequence encoding domains. The resulting DNA fragments were fused in frame into the C-terminus to sequence encoding an engineered thermostable carrier molecule.

NAV(N1): (SEQ ID NO.: 27):
GGATCCTTAATTAAAATGGGATTCGTGCTTTTCTCTCAGCTTCCTTCTTT
CCTTCTTGTGTCTACTCTTCTTCTTTTCCTTGTGATTTCTCACTCTTGCC
GTGCTCAAAATGTCGACCTTATGCTTCAGATTGGAAACATGATTTCTATT
TGGGTGTCACACTCTATTCACACTGGAAACCAGCATCAGTCTGAGCCAAT
TTCTAACACTAACCTTTTGACTGAGAAGGCTGTGGCTTCTGTTAAGTTGG
CTGGAAACTCTTCTCTTTGCCCTATTAACGGATGGGCTGTGTACTCTAAG
GATAACTCTATTAGGATTGGATCTAAGGGAGATGTGTTCGTGATTAGGGA
GCCATTCATTTCTTGCTCTCACCTTGAGTGCCGTACTTTCTTCCTTACTC
AGGGTGCTCTTCTTAACGATAAGCACTCTAACGGAACTGTGAAGGATAGG
TCTCCACACAGGACTCTTATGTCTTGTCCAGTTGGAGAAGCTCCATCTCC
ATACAACTCTAGATTCGAGTCTGTTGCTTGGAGTGCTTCTGCTTGCCATG
ATGGAACTTCATGGCTTACTATTGGAATTTCTGGACCAGATAACGGAGCT
GTTGCTGTGCTTAAGTACAACGGAATTATTACTGATACCATCAAGTCTTG
GAGGAACAACATTCTTAGGACTCAGGAGTCTGAGTGTGCTTGCGTTAACG
GATCTTGCTTCACTGTGATGACTGATGGACCATCTAATGGACAGGCTTCT
CACAAGATTTTCAAGATGGAGAAGGGAAAGGTTGTGAAGTCTGTGGAACT
TGATGCTCCAAACTACCATTACGAGGAGTGTTCTTGCTATCCAGATGCTG
GAGAGATTACTTGTGTGTGCCGTGATAATTGGCATGGATCTAACAGGCCA
TGGGTGTCATTCAATCAGAACCTTGAGTACCAGATTGGTTACATTTGCTC
TGGAGTGTTCGGAGATAATCCAAGGCCAAACGATGGAACTGGATCTTGTG
GACCAGTGTCATCTAATGGAGCTGGAGGAGTGAAGGGATTCTCTTTCAAG
TACGGAAACGGAGTTTGGATTGGAAGGACTAAGTCTACTAACTCTAGGAG
TGGATTCGAGATGATTTGGGACCCAAACGGATGGACTGAGACTGATTCTT
CTTTCTCTGTGAAGCAGGATATTGTGGCTATTACTGATTGGAGTGGATAC
TCTGGATCTTTCGTTCAGCACCCAGAGCTTACTGGACTTGATTGCATTAG
GCCATGCTTCTGGGTTGAACTTATTAGGGGAAGGCCAAAGGAGTCTACTA
TTTGGACTTCTGGATCTTCTATTTCTTTCTGCGGAGTGAATTCTGATACT
GTGGGATGGTCTTGGCCAGATGGAGCTGAGCTTCCATTCACTATTGATAA
GGTCGACCATCATCATCATCACCACAAGGATGAGCTTTGACTCGAG

NAV: (SEQ ID NO.: 16):
LMLQIGNMISIWVSHSIHTGNQHQSEPISNTNLLTEKAVASVKLAGNSSL
CPINGWAVYSKDNSIRIGSKGDVFVIREPFISCSHLECRTFFLTQGALLN
DKHSNGTVKDRSPHRTLMSCPVGEAPSPYNSRFESVAWSASACHDGTSWL

TIGISGPDNGAVAVLKYNGIITDTIKSWRNNILRTQESECACVNGSCFTV

MTDGPSNGQASHKIFKMEKGKVVKSVELDAPNYHYEECSCYPDAGEITCV

CRDNWHGSNRPWVSFNQNLEYQIGYICSGVFGDNPRPNDGTGSCGPVSSN

GAGGVKGFSFKYGNGVWIGRTKSTNSRSGFEMIWDPNGWTETDSSFSVKQ

DIVAITDWSGYSGSFVQHPELTGLDCIRPCFWVELIRGRPKESTIWTSGS

SISFCGVNSDTVGWSWPDGAELPFTIDK

NAW(N2): (SEQ ID NO.: 28):
GGATCCTTAATTAAAATGGGATTCGTGCTTTTCTCTCAGCTTCCTTCTTT

CCTTCTTGTGTCTACTCTTCTTCTTTTCCTTGTGATTTCTCACTCTTGCC

GTGCTCAAAATGTCGACAAGCAGTACGAGTTCAACTCTCCACCAAACAAC

CAGGTTATGCTTTGCGAGCCAACTATTATTGAGAGGAACATTACTGAGAT

TGTGTACCTTACTAACACTACTATTGAGAAGGAGATTTGCCCAAAGTTGG

CTGAGTACCGTAATTGGTCTAAGCCACAGTGCAACATTACTGGATTCGCT

CCATTCTCTAAGGATAACTCAATTAGGCTTTCTGCTGGAGGAGATATTTG

GGTTACAAGGGAGCCATACGTTTCTTGCGATCCAGATAAGTGCTACCAGT

TCGCTCTTGGACAAGGAACTACTCTTAACAACGTGCACTCTAACGATACT

GTGCACGATAGGACTCCATACCGTACTCTTTTGATGAACGAGCTTGGAGT

TCCATTCCACCTTGGAACTAAGCAAGTGTGCATTGCTTGGTCATCTTCAT

CTTGCCACGATGGAAAGGCTTGGCTTCATGTTTGCGTGACTGGAGATGAT

GAGAACGCTACTGCTTCTTTCATCTACAACGGAAGGCTTGTGGATTCTAT

TGTTTCTTGGTCTAAGAAGATTCTTAGGACTCAGGAGTCTGAGTGTGTGT

GCATTAACGGAACTTGCACTGTGGTTATGACTGATGGATCTGCTTCTGGA

AAGGCTGATACAAAGATTCTTTTCATTGAGGAGGGAAAGATTGTGCACAC

TTCTACTCTTTCTGGATCTGCTCAGCATGTTGAGGAGTGTTCTTGCTACC

CAAGGTATCCAGGAGTTAGATGTGTGTGCCGTGATAACTGGAAGGGATCT

AACAGGCCAATTGTGGATATTAACATTAAGGATTACTCTATTGTGTCATC

TTATGTGTGCTCTGGACTTGTTGGAGATACTCCAAGGAAGAACGATTCTT

CTTCATCTTCACACTGCCTTGATCCAAATAACGAGGAGGGAGGACATGGA

GTTAAGGGATGGGCTTTCGATGATGGAAACGATGTTTGGATGGGAAGGAC

TATTTCTGAGAAGTTGAGGAGCGGATACGAGACTTTCAAAGTGATTGAGG

GATGGTCTAACCCAAATTCTAAGCTGCAGATTAACAGGCAAGTGATTGTG

GATAGGGGAAACAGGAGTGGATACTCTGGAATTTTCTCTGTGGAGGGAAA

GTCTTGCATTAACAGATGCTTCTACGTGGAGCTTATTAGGGGAAGGAAGC

AGGAGACTGAGGTTTTGTGGACTTCTAACTCTATTGTGGTGTTCTGCGGA

ACTTCTGGAACTTACGGAACTGGATCTTGGCCAGATGGAGCTGATATTAA

CCTTATGCCAATTGTCGACCATCATCACCATCACCACAAGGATGAGCTTT

GACTCGAG

NAW: (SEQ ID NO.: 18):
KQYEFNSPPNNQVMLCEPTIIERNITEIVYLTNTTIEKEICPKLAEYRNW

SKPQCNITGFAPFSKDNSIRLSAGGDIWVTREPYVSCDPDKCYQFALGQG

TTLNNVHSNDTVHDRTPYRTLLMNELGVPFHLGTKQVCIAWSSSSCHDGK

AWLHVCVTGDDENATASFIYNGRLVDSIVSWSKKILRTQESECVCINGTC

TVVMTDGSASGKADTKILFIEEGKIVHTSTLSGSAQHVEECSCYPRYPGV

RCVCRDNWKGSNRPIVDINIKDYSIVSSYVCSGLVGDTPRKNDSSSSSHC

LDPMNEEGGHGVKGWAFDDGNDVWMGRTISEKLRSGYETFKVIEGWSNPN

SKLQINRQVIVDRGNRSGYSGIFSVEGKSCINRCFYVELIRGRKQETEVL

WTSNSIVVFCGTSGTYGTGSWPDGADTNLMPI

Generation of Thermostable Carrier Construct

Full length native *C. thermocellum* lichenase, LicB, consists sequentially of a leader peptide (Lp), an N-terminal portion (A), a surface loop (1), a C-terminal portion (C), a Pro-Thr box, and a cellulosome-binding domain (C-BD). We removed the Lp, Pro-Thr box and C-BD encoding sequences from the LicB encoding gene, circularly permutated the molecule to invert the N- and C-termini (Musiychuk et al., 2007, *Influenza and Other Respiratory Viruses*, 1:1), and incorporated unique restriction endonuclease sites for cloning target sequences at the N- and C-termini as well as into the surface loop (l). The resulting engineered carrier molecule sequence was verified, and is designated LicKM.

SEQ ID NO.: 29:
GGATCCTTAATTAAAATGGGAGGTTCTTATCCATATAAGTCTGGTGAGTA

TAGAACTAAGTCTTTCTTTGGATATGGTTATTATGAAGTTAGGATGAAGG

CTGCAAAGAACGTTGGAATTGTTTCTTCTTTCTTTACTTATACTGGACCA

TCTGATAACAACCCATGGGATGAGATTGATATTGAGTTTCTTGGAAAGGA

TACTACTAAGGTTCAATTCAACTGGTATAAGAATGGTGTTGGTGGAAACG

AGTATCTTCATAACCTTGGATTTGATGCTTCTCAAGATTTTCATACTTAT

GGTTTTGAGTGGAGACCAGATTATATTGATTTTTATGTTGATGGAAAGAA

GGTTTATAGAGGTACTAGAAACATTCCAGTTACTCCTGGAAAGATTATGA

TGAATCTTTGGCCAGGAATTGGTGTTGATGAATGGCTTGGTAGATATGAT

GGAAGAACTCCACTTCAAGCTGAGTATGAGTATGTTAAGTATTATCCAAA

CGGTAGATCTGAATTCAAGCTTGTTGTTAATACTCCATTTGTTGCTGTTT

TCTCTAACTTTGATTCTTCTCAATGGGAAAAGGCTGATTGGGCTAACGGT

TCTGTTTTTAACTGTGTTTGGAAGCCATCTCAAGTTACTTTTTCTAACGG

AAAGATGATTCTTACTTTGGATAGAGAGTATGTCGACCATCATCATCATC

ATCATTGACTCGAGCTC

SEQ ID NO.: 30:
MGGSYPYKSGEYRTKSFFGYGYYEVRMKAAKNVGIVSSFFTYTGPSDNNP

WDEIDIEFLGKDTTKVQFNWYKNGVGGNEYLHNLGFDASQDFHTYGFEWR

PDYIDFYVDGKKVYRGTRNIPVTPGKIMMNLWPGIGVDEWLGRYDGRTPL

QAEYEYVKYYPNGRSEFKLVVNTPFVAVFSNFDSSQWEKADWANGSVFNC

VWKPSQVTFSNGKMILTLDREYVDHHHHHH

For certain constructs, we engineered a PR1a signal peptide and KDEL sequence at the N- and C-termini of LicKM. The nucleic acid and amino acid sequences of these constructs are shown in SEQ ID NO.: 31 and SEQ ID NO.: 32.

SEQ ID NO.: 31:
GGATCCTTAATTAAAATGGGATTTGTTCTCTTTTCACAATTGCCTTCATT

TCTTCTTGTCTCTACACTTCTCTTATTCCTAGTAATATCCCACTCTTGCC

GTGCCCAAAATGGAGGTTCTTATCCATATAAGTCTGGTGAGTATAGAACT

AAGTCTTTCTTTGGATATGGTTATTATGAAGTTAGGATGAAGGCTGCAAA

GAACGTTGGAATTGTTTCTTCTTTCTTTACTTATACTGGACCATCTGATA

ACAACCCATGGGATGAGATTGATATTGAGTTTCTTGGAAAGGATACTACT

AAGGTTCAATTCAACTGGTATAAGAATGGTGTTGGTGGAAACGAGTATCT

TCATAACCTTGGATTTGATGCTTCTCAAGATTTTCATACTTATGGTTTTG

AGTGGAGACCAGATTATATTGATTTTTATGTTGATGGAAAGAAGGTTTAT

AGAGGTACTAGAAACATTCCAGTTACTCCTGGAAAGATTATGATGAATCT

TTGGCCAGGAATTGGTGTTGATGAATGGCTTGGTAGATATGATGGAAGAA

CTCCACTTCAAGCTGAGTATGAGTATGTTAAGTATTATCCAAACGGTAGA

TCTGAATTCAAGCTTGTTGTTAATACTCCATTTGTTGCTGTTTTCTCTAA

CTTTGATTCTTCTCAATGGGAAAAGGCTGATTGGGCTAACGGTTCTGTTT

TTAACTGTGTTTGGAAGCCATCTCAAGTTACTTTTTCTAACGGAAAGATG

ATTCTTACTTTGGATAGAGAGTATGTCGACCATCATCATCATCATCATAA

GGATGAACTTTGACTCGAGCTC

SEQ ID NO.: 32:
MGFVLFSQLPSFLLVSTLLLFLVISHSCRAQNGGSYPYKSGEYRTKSFFG

YGYYEVRMKAAKNVGIVSSFFTYTGPSDNNPWDEIDIEFLGKDTTKVQFN

WYKNGVGGNEYLHNLGFDASQDFHTYGFEWRPDYIDFYVDGKKVYRGTRN

IPVTPGKIMMNLWPGIGVDEWLGRYDGRTPLQAEYEYVKYYPNGRSEFKL

VVNTPFVAVFSNFDSSQWEKADWANGSVFNCVWKPSQVTFSNGKMILTLD

REYVDHHHHHHKDEL

Generation of Recombinant Antigen Constructs

Figure 2:
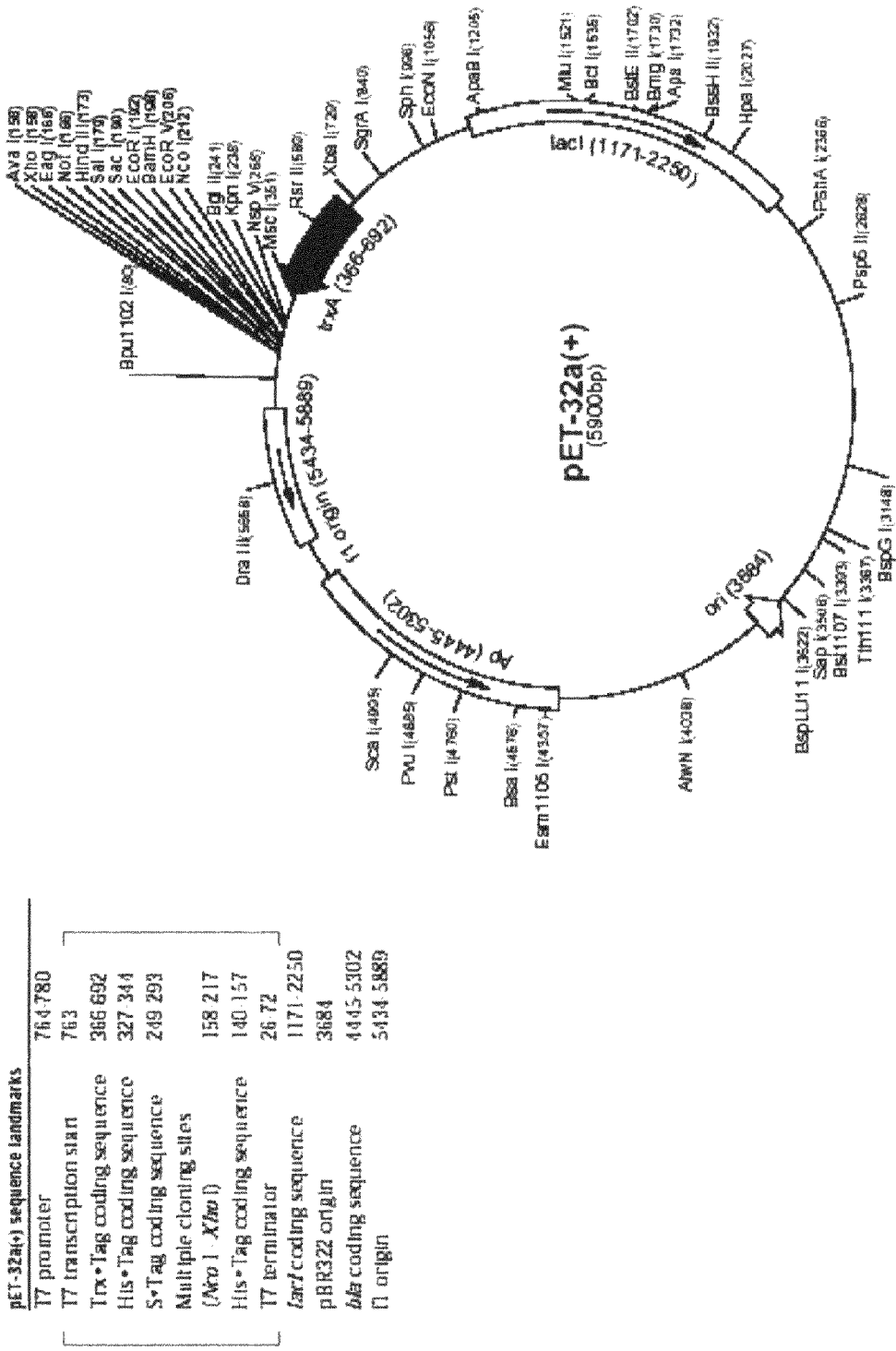
Figure 3:
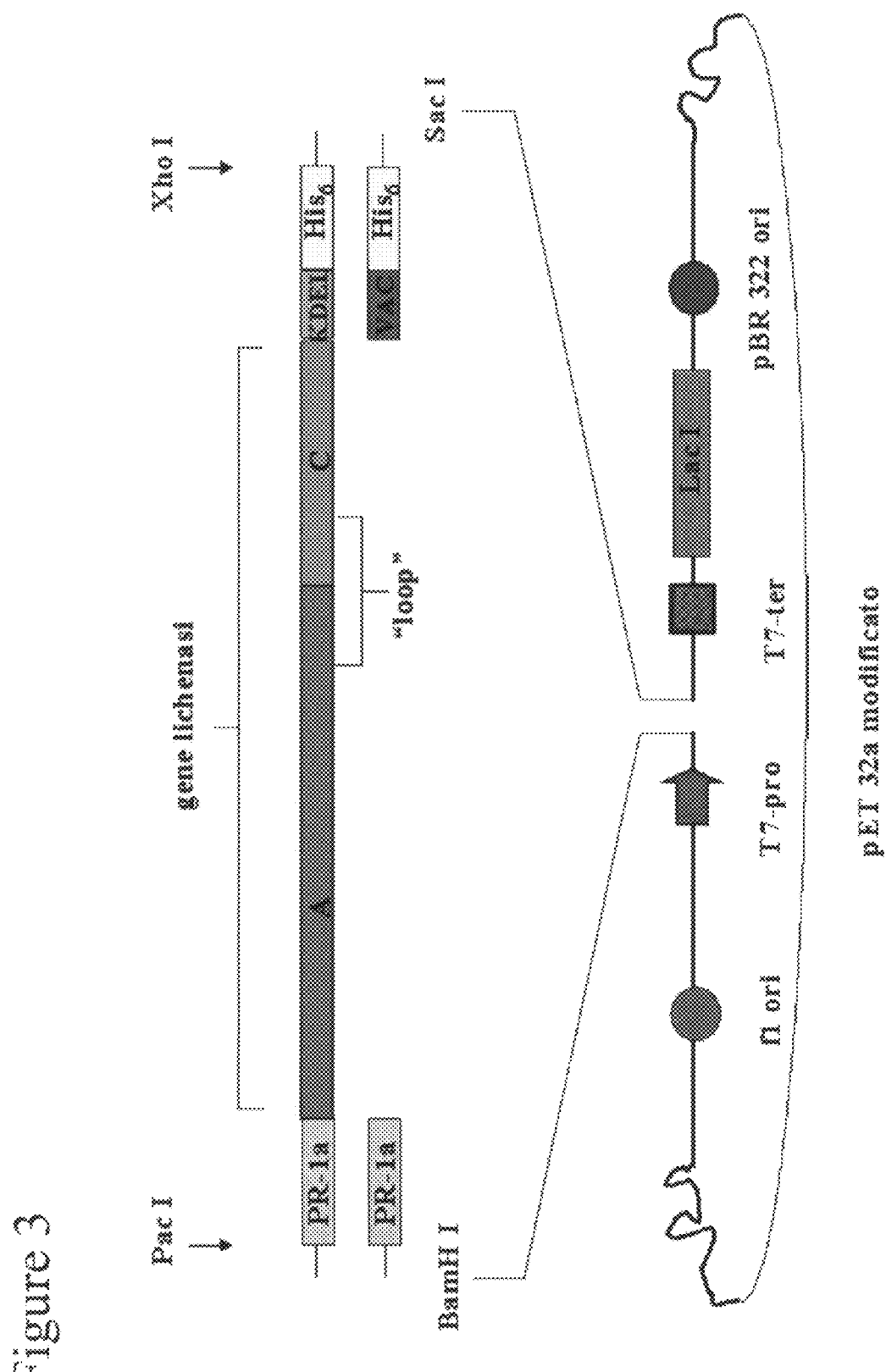

We used pET expression vectors, derived from pBR322 plasmid, engineered to take advantage of the features of the T7 bacteriophage gene 10 that promote high-level transcription and translation. The bacteriophage encoded RNA polymerase is highly specific for the T7 promoter sequences, which are rarely encountered in genomes other than T7 phage genome (FIG. 2). pET-32 has been used for fusing the HA and NA constructs into the loop region of a modified lichenase sequence that had been cloned in this vector. The catalytic domain of the lichenase gene with the upstream sequence PR-1A ("Pathogen-Related protein 1A"), with a endoplasmic reticulum (KDEL) or a vacuolar retaining sequence (VAC) and a downstream $His_6$ tag were cloned between the Pac I and XhoI sites in a modified pET-32 vector (in which the region between the T7 promoter and the T7 terminator had been excised). In this way the pET-PR-LicKM-KDEL and pET-PR-LicKM-VAC were obtained (FIG. 3).

The DNA fragment HA domain or NA was subcloned into the loop (1) portion of LicKM to give a fusion in the correct reading frame for translation. LicKM-NA fusions were constructed. The DNA fragment of NAW or NAV was subcloned into the C-terminus of LicKM using a SalI site to give a fusion in the correct reading frame for translation.

Example 2

Generation of Vaccine Candidate Antigen Vectors

Figure 4:
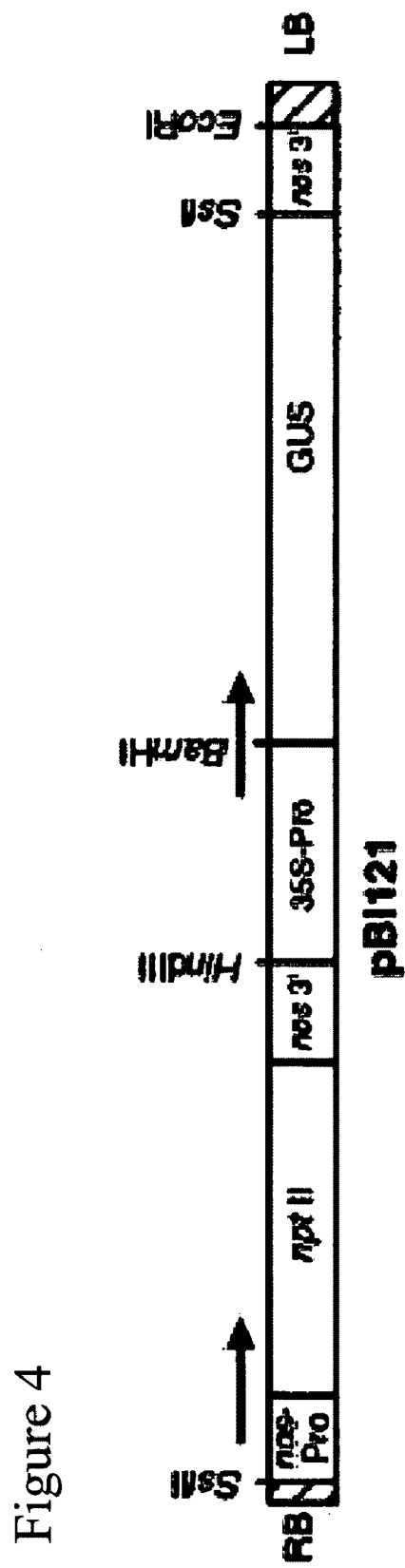
Figure 5:
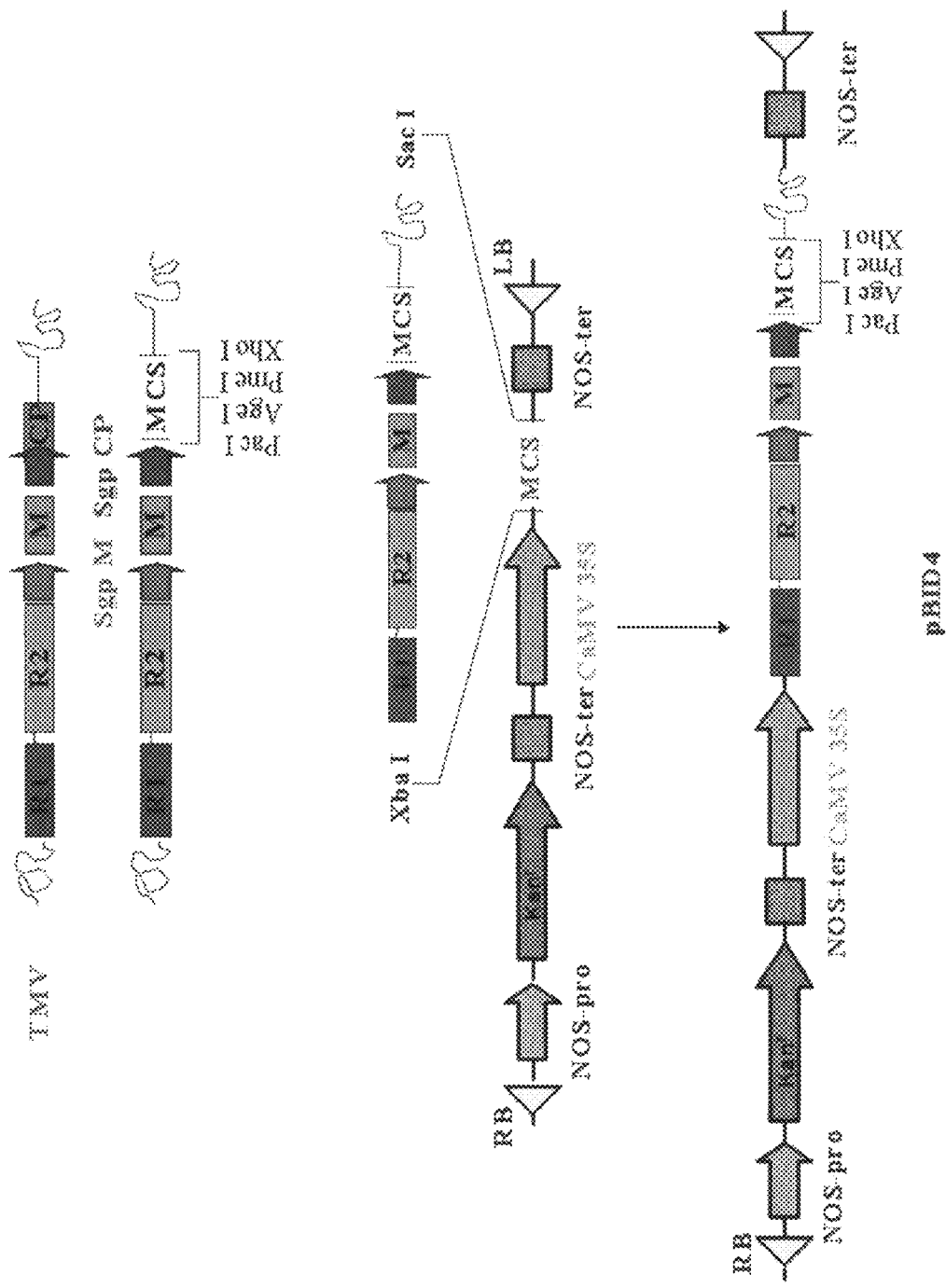
Figure 6:
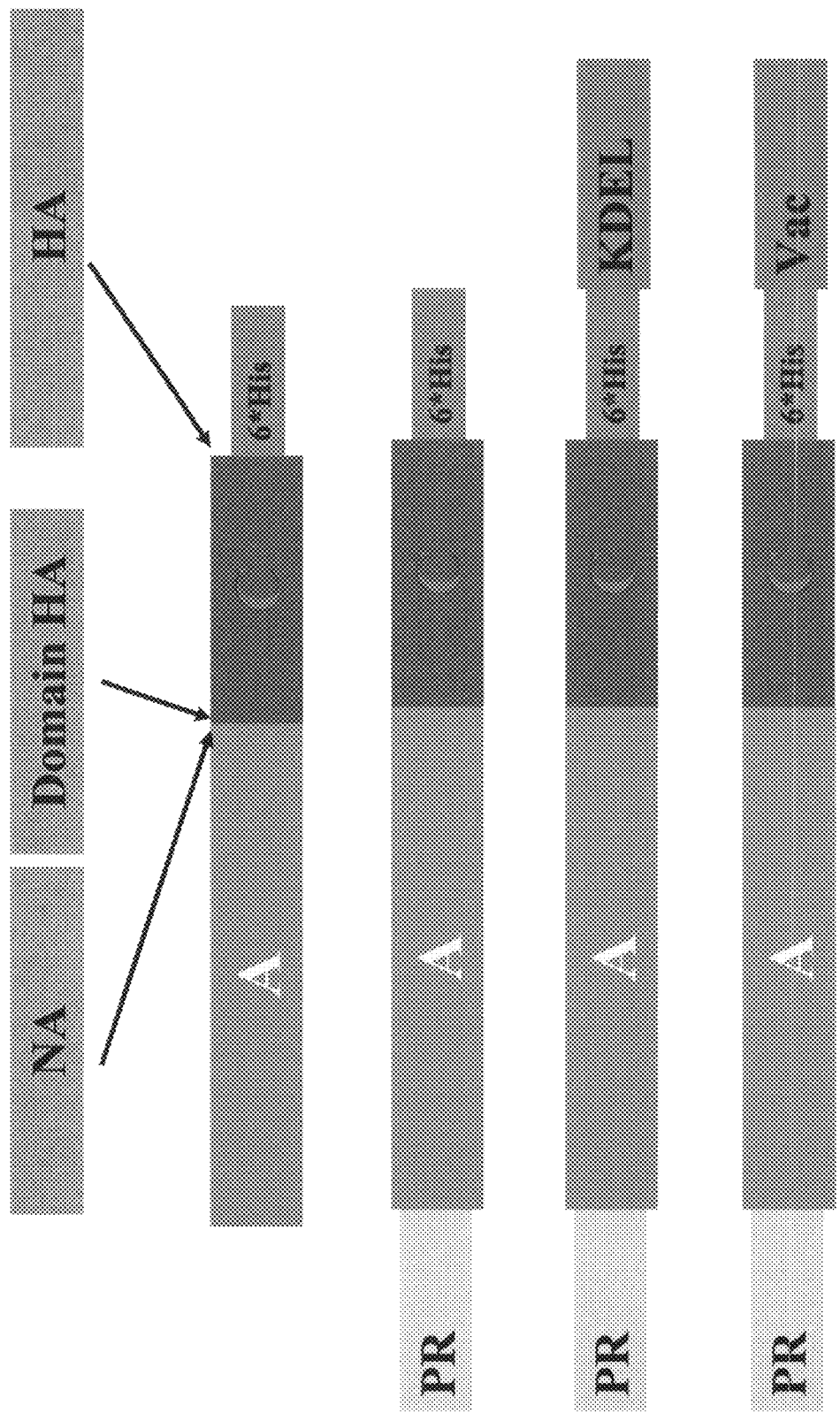

Target antigen constructs LicKM-HA(SD), LicKM-HA(GD), or LicKM-NA were individually subcloned into the chosen viral vector (pBI-D4). pBI-D4 is a pBI121-derived binary vector in which the reporter gene coding for the *Escherichia coli* β-D-glucuronidase (GUS) has been replaced by a "polylinker" where, between the Xba I and Sac I sites, a TMV-derived vector has been cloned (FIG. 4). pBI-D4 is a TMV-based construct in which a foreign gene to be expressed (e.g., target antigen, such as LicKM-HA(SD), LicKM-HA(GD), LicKM-NA) replaces the coat protein (CP) gene of TMV. The virus retains the TMV 126/183 kDa gene, the movement protein (MP) gene, and the CP subgenomic mRNA promoter (sgp), which extends into the CP open reading frame (ORF). The start codon for CP has been mutated. The virus lacks CP and therefore cannot move throughout the host plant via phloem. However, cell-to-cell movement of viral infection remains functional, and the virus can move slowly to the upper leaves in this manner. A multiple cloning site (PacI-PmeI-AgeI-XhoI) has been engineered at the end of sgp for expression of foreign genes, and is followed by the TMV 3' non-translated region (NTR). The 35S promoter is fused at the 5' end of the viral sequence. The vector sequence is positioned between the BamHI and SacI sites of pBI121. The hammerhead ribozyme is placed 3' of the viral sequence (Chen et al., 2003, *Mol. Breed.*, 11:287). These constructs include fusions of sequences encoding LicKM-HA-SD, LicKM-HA(GD), or NA to sequences encoding the signal peptide from tobacco PR-1a protein, a 6×His tag and the ER-retention anchor sequence KDEL or vacuolar sequence (FIG. 5). For constructs that contain sequence encoding, PR-LicKM-HA(SD)-KDEL, PR-LicKM-HA(GD)-KDEL, and PR-LicKM-NA-KDEL the coding DNA was introduced as PacI-XhoI fragments into pBI-D4. Furthermore, HAW (HA Wyoming), HAV (HA Vietnam), NAW (NA Wyoming), and NAV (NA Vietnam) were introduced directly as PacI-XhoI fragments into pBI-D4. Nucleotide sequence was subsequently verified spanning the subcloning junctions of the final expression constructs (FIG. 6).

Example 3

Generation of Plants and Antigen Production

*Agrobacterium* Infiltration of Plants

*Agrobacterium*-mediated transient expression system achieved by *Agrobacterium* infiltration can be utilized (Turpen et al., 1993, *J. Virol. Methods*, 42:227). Healthy leaves of *N. benthamiana* were infiltrated with *A. rhizogenes* or *A. tumefaciens* (GV3101) containing viral vectors engineered to express LicKM-HA or LicKM-NA.

The *A. rhizogenes* strain A4 (ATCC 43057) was transformed with the constructs pBI-D4-PR-LicKM-HA(SD)-KDEL, PR-LicKM-HA(GD)-KDEL, and pBI-D4-PR-LicKM-NA-KDEL. *Agrobacterium* cultures were grown and induced as described by Kapila et al. (1997, *Plant Sci.*, 122: 101). A 2 ml starter-culture (picked from a fresh colony) was grown overnight in YEB (5 g/l beef extract, 1 g/l yeast extract, 5 g/l peptone, 5 g/l sucrose, 2 mM $MgSO_4$) with 25 µg/ml kanamycin at 28° C. The starter culture was diluted 1:500 into 500 ml of YEB with 25 µg/ml kanamycin, 10 mM 2-4(-morpholino)ethanesulfonic acid (MES) pH 5.6, 2 mM additional $MgSO_4$ and 20 µM acetosyringone. The diluted culture was then grown overnight to an $O.D._{600}$ of ~1.7 at 28° C. The cells were centrifuged at 3,000×g for 15 minutes and resuspended in MMA medium (MS salts, 10 mM MES pH 5.6, 20 g/l sucrose, 200 μM acetosyringone) to an O.D.$_{600}$ of 2.4, kept for 1-3 hour at room temperature, and used for *Agrobacterium*-infiltration. *N. benthamiana* leaves were injected with the *Agrobacterium*-suspension using a disposable syringe without a needle. Infiltrated leaves were harvested 4-7 days (e.g., 6 days) post-infiltration.

Figure 7:
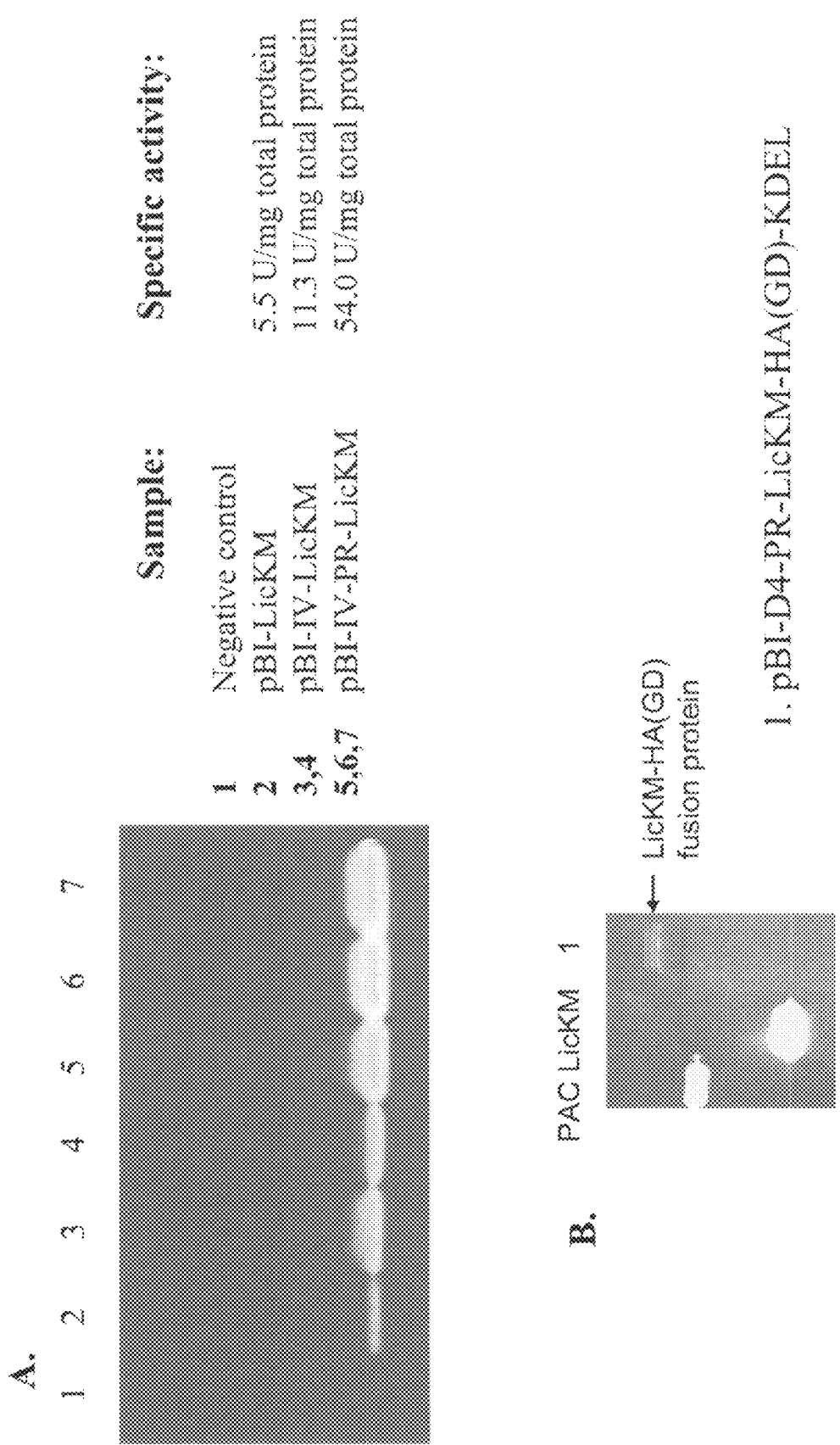
Figure 8:
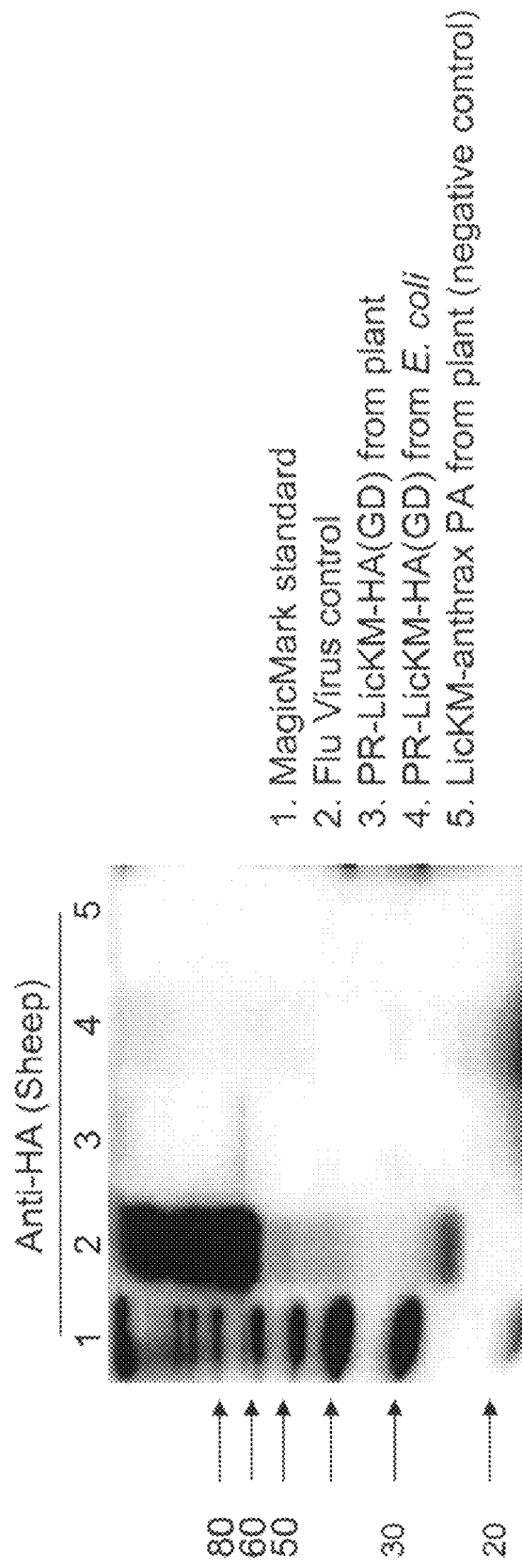
Figure 9:
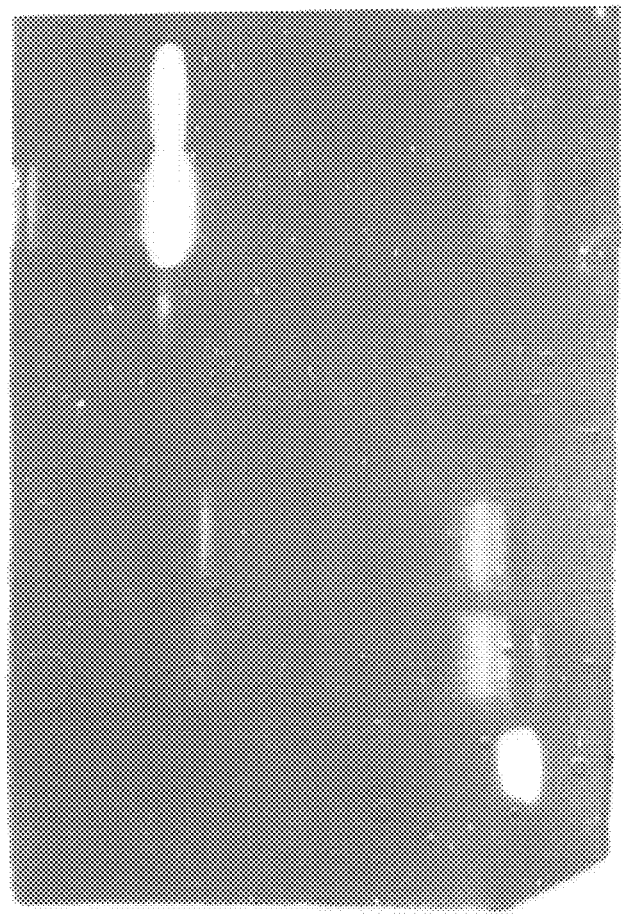
Figure 10:
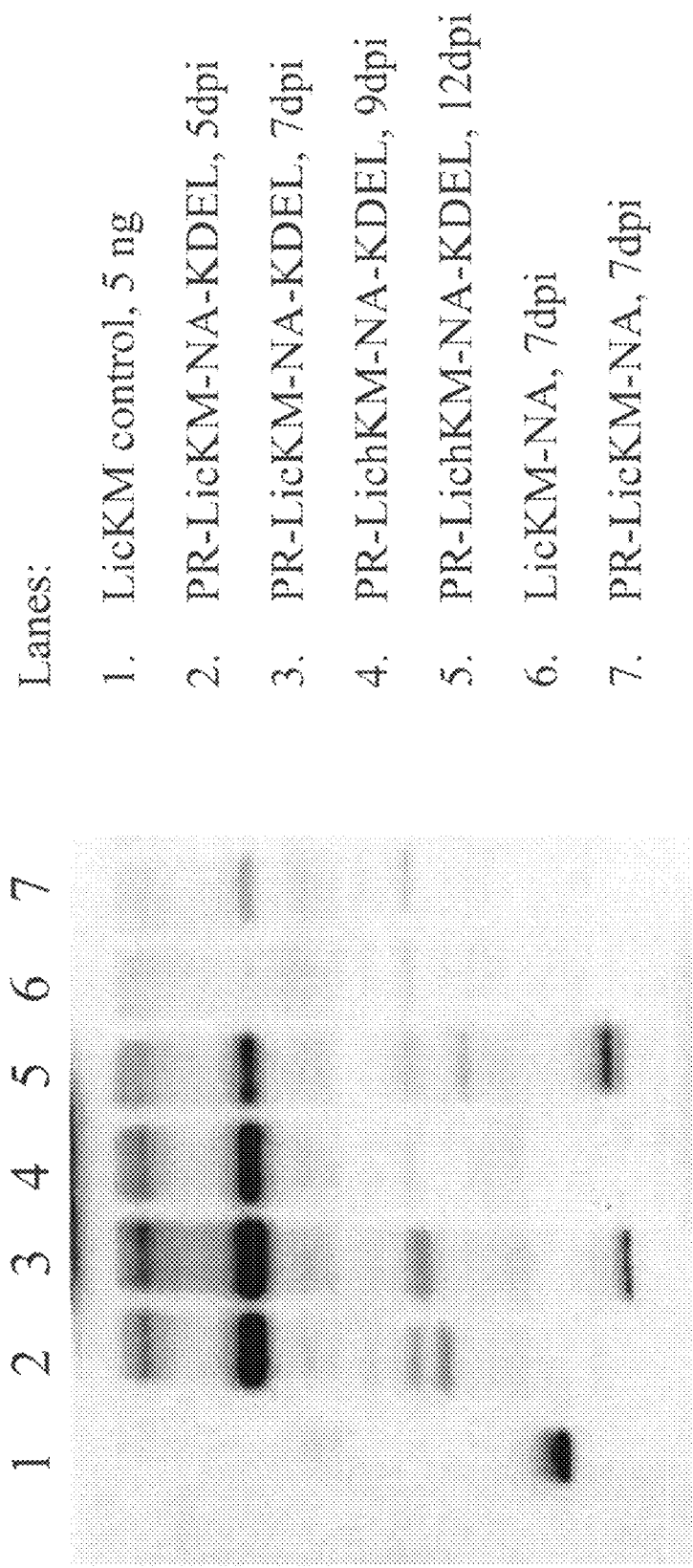

Plants were screened for the presence of target antigen expression by assessment of lichenase activity assay and immunoblot analysis (FIGS. 7, 8, 9, and 10). Zymogram analysis revealed the expression of both HA and NA chimeric proteins in the *Nicotiana benthamiana* infiltrated leaves tested. The expression is associated with lichenase activity (FIGS. 7 and 9). The activity band related to the fusion proteins show a higher molecular weight than the lichenase control and the same molecular weight of the product expressed by plants after agro-infection, confirming the presence of whole fusion product.

Clonal Root and Clonal Root Line Generation

*Nicotiana benthamiana* leaf explants 1 cm×1 cm wide are obtained from leaves after sterilization in 0.1% $NH_4Cl$ and six washing in sterile $dH_2O$. The explants are slightly damaged with a knife on the abacsial side and co-cultured with the *Agrobacterium rhizogenes*, strain A4, containing either the pBID4-Lic-HA-KDEL or the pBID4-Lic-NA-KDEL. The explants are incubated for 2' with an *Agrobacterium* overnight culture (O.D.$_{600nm}$=0.8-1) centrifuged for 10 minutes at 3,000 rpm a 4° C. and resuspended in MMA medium to a final O.D.$_{600nm}$=0.5 in presence of 20 mM acetosyringone. At the end of the incubation, the explant is dried on sterile paper and transferred onto 0.8% agar MS plates in presence of 1% glucose and 20 mM acetosyringone. Plates are parafilmed and kept at R.T. for two days. The explants are then transferred onto MS plates in presence of 500 mg/l Cefotaxim (Cif), 100 mg/l Timentin (Tim) and 25 mg/l kanamycin. After approximately 5 weeks the generation of transgenic roots is obtained from *Nicotiana benthamiana* leaf explants transformed with *Agrobacterium rhizogenes* containing the pBID4-Lic-HA-KDEL and pBID4-Lic-NA-KDEL constructs.

After transformation, hairy roots can be cut off and placed in a line on solid, hormone free $K_3$ medium. Four to six days later the most actively growing roots are isolated and transferred to liquid $K_3$ medium. Selected roots are cultured on a rotary shaker at 24° C. in the dark and clonal lines are isolated and subcultured weekly. Roots and/or clonal lines can be screened for the presence of target antigen expression by assessment of lichenase activity assay and immunoblot analysis.

Example 4

Production of Vaccine Candidate 100 mg samples of *N. benthamiana* infiltrated leaf material were harvested at 4, 5, 6 and 7 days post-infection. The fresh tissue was analysed for protein expression right after being harvested or collected at −80° C. for the preparation of subsequent crude plants extracts or for fusion protein purification.

Fresh samples were resuspended in cold PBS1× plus Protease inhibitors (Roche) in a 1/3 w/v ratio (1 ml/0.3 g of tissue) and ground with a pestel. The homogenates were boiled for 5 minutes in SDS gel loading buffer and then clarified by centrifugation for 5 minutes at 12.000 rpm at 4° C. The supernatants were transferred in a fresh tube and 20 μl, 1 μl or their dilutions were separated on a 12% SDS-PAGE and analyzed by Western analysis using anti-His$_6$-HA mouse or rabbit anti-lichenase polyclonal antibodies and/or by zymogram analysis to assess enzymatic activity indicating functional lichenase activity. Zymography is an electrophoretic method for measuring enzymatic activity. The method is based on a sodium dodecyl sulfate gel impregnated with a substrate which is degraded by the enzymes resolved during the incubation period. The staining of the gel reveals sites of enzymatic activity as white bands on a dark red background. Within a certain range the band intensity can be related linearly to the amount of enzyme loaded.

HA expression in *Nicotiana benthamiana* plants infiltrated either with *Agrobacterium tumefaciens* or *Agrobacterium rhizogenes* containing the plasmid pBID4-LicKM-HA(SD)-KDEL or pBID4-LicKM-HA(GD)-KDEL leads to a specific band corresponding to the molecular weight of the chimeric protein LicKM-HA(SD)-KDEL or LicKM-HA(GD)-KDEL if the HA protein electrophoretic mobility in the fusion protein corresponds to the theoretic MW (the lichenase enzyme MW is about 28 kD).

Quantification of the chimeric proteins Lic-HA-KDEL and Lic-NA-KDEL expressed in the crude extract can be made by immunoblotting both on the manually infiltrated tissues and on the vacuum-infiltrated tissues.

Purification of Antigens

Leaves from plants infiltrated with recombinant *Agrobacterium tumefaciens* containing the pBID4-LicKM-HA(SD)-KDEL, pBID4-LicKM-HA(GD)-KDEL, and pBID4-full-length-NA-KDEL constructs were ground by homogenization. Extraction buffer with "EDTA-free" protease inhibitors (Roche) and Triton X-100 1% was used at a ratio of 3 volumes w/v and rocked for 30 min at 4° C. Extracts were clarified by centrifugation at 9000×g per 10' at 4° C. The supernatant was sequentially filtered through miracloth, centrifugated at 20.000×g for 30' at 4° C. and filtered through 0.45-μm filter, before chromatographic purification.

Resulting extract was cut using ammonium sulfate precipitation. Briefly, $(NH_4)_2SO_4$ was added to extract to 20% saturation, incubated on ice for 1 h and spun down at 18,000×g for 15 min. Pellet was discarded and $(NH_4)_2SO_4$ added slowly to 60% saturation, incubated on ice for 1 h, and spun down at 18,000×g for 15 min. Supernatant was discarded and resulting pellet resuspended in buffer, then maintained on ice for 20 min, followed by centrifuge at 18,000×g for 30 min and supernatant dialyzed overnight against 10000 volumes of washing buffer:

His-tagged LicKM-HA(SD)-KDEL, LicKM-HA(GD)-KDEL, and full-length-NA-KDEL chimeric proteins were purified by using IMAC ("Immobilized Metal Affinity Chromatography," GE Healthcare) at room temperature under gravity. The purification was performed under non-denaturing conditions. Proteins were collected as 0.5 ml fractions, which are unified, added with 20 mM EDTA, dialyzed against PBS1× overnight at 4° C. and analyzed by SDS-PAGE.

Alternatively, fractions were then collected together added with 20 mM EDTA, dialyzed against $NaH_2PO_4$ 10 mM, overnight, at 4° C. and purified by Anion Exchange Chromatography. For LicKM-HA(SD)-KDEL, LicKM-HA(GD)-KDEL, and full-length-NA-KDEL purification, anion exchange column Q Sepharose Fast Flow (Amersham Pharmacia Biosciences) was used. Samples of the LicKM-HA (SD)-KDEL, LicKM-HA(GD)-KDEL, and full-length-NA-KDEL affinity or ion-exchange purified chimeric proteins were separated on 12% polyacrylamide gels followed by Coomassie staining. Separated proteins were also electrophoretically transferred onto PDVF membranes for Western blot analysis using polyclonal anti-lichenase antibody and successively with anti-rabbit IgG horseradish peroxidase-conjugated antibody.

Collected fractions after dialysis were analyzed by immunoblotting using both the pAb α-lichenase and the pAb α-His$_6$. The His-tag was maintained by the expressed chimeric proteins and the final concentration of the purified protein was evaluated by software.

Hemagglutination Assay

Three species of red blood cells (RBC's) from two different sources were used to demonstrate hemagglutinating activity in plant-produced preparations of Influenza vaccines. The vaccine material assayed was referred to as "domain 3" (globular domain) from either Influenza A/Wyoming/03/03 (an H3N2 virus) or Influenza A/Vietnam/1194/2004 (an H5N1 virus).

RBC's from chicken, turkey and horse were washed individually in phosphate buffered saline (PBS) three times and adjusted to 0.5% v/v with PBS. Round bottomed, 96 well microtiter plates were tested with PBS alone for quality assurance demonstrating that only Falcon plates consistently provided clear delineation between positive and negative results. Vaccine material was assayed in duplicate starting at 0.5 mg/ml and diluted 2 fold up the plate by pipetting 25 μl of material into 25 μl of PBS stepwise. 25 μl of a 0.5% suspension of one species of RBC/plate was then dispensed into all wells of that plate. Plates were shaken to distribute RBC's and incubated at 4 C for 4 hours before determining positive from negative results.

Figure 11:
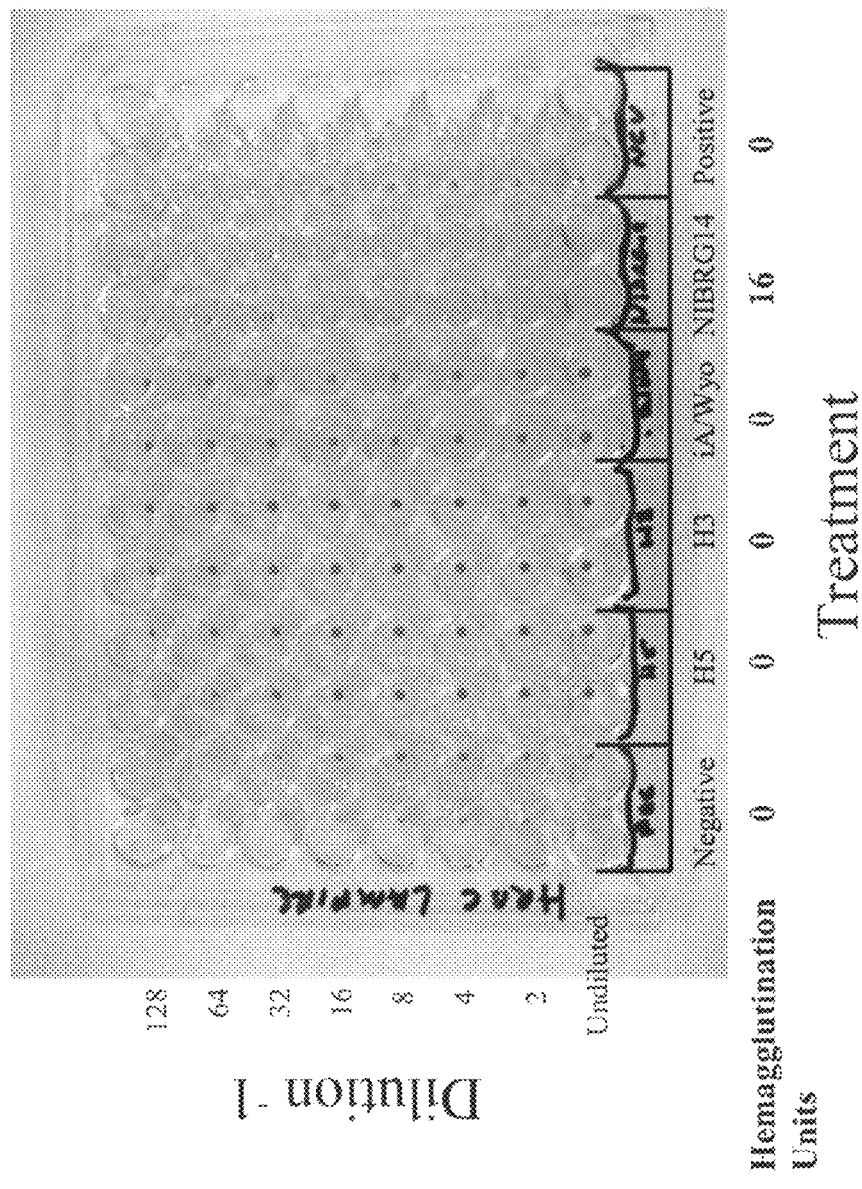

Domain 3 from Influenza A/Vietnam/1194/2004 (an H5N1 virus) consistently and reproducibly gave a positive result on avian RBC's but not horse RBC's. The endpoint dilution was consistently 8 in replicates and experiment repeats, indicating the H5 domain 3 could hemagglutinate avian RBC's at a concentration of 62.5 μg (FIG. 11).

Example 5

Immunogenicity Studies

Initial Immunogenicity Study

An initial immunogenicity study was conducted to determine whether plant-produced LicKM-antigen fusions could induce specific serum IgG in mice immunized intraperitoneally, and whether the induced antibodies could neutralize influenza virus in vitro. The study used LicKM, LicKM-HA (SD), LicKM-HA(SD), and recombinant NA enriched from *Agrobacterium* infiltrated leaves of *N. benthamiana* to 75% purity, as described above.

Figure 12:
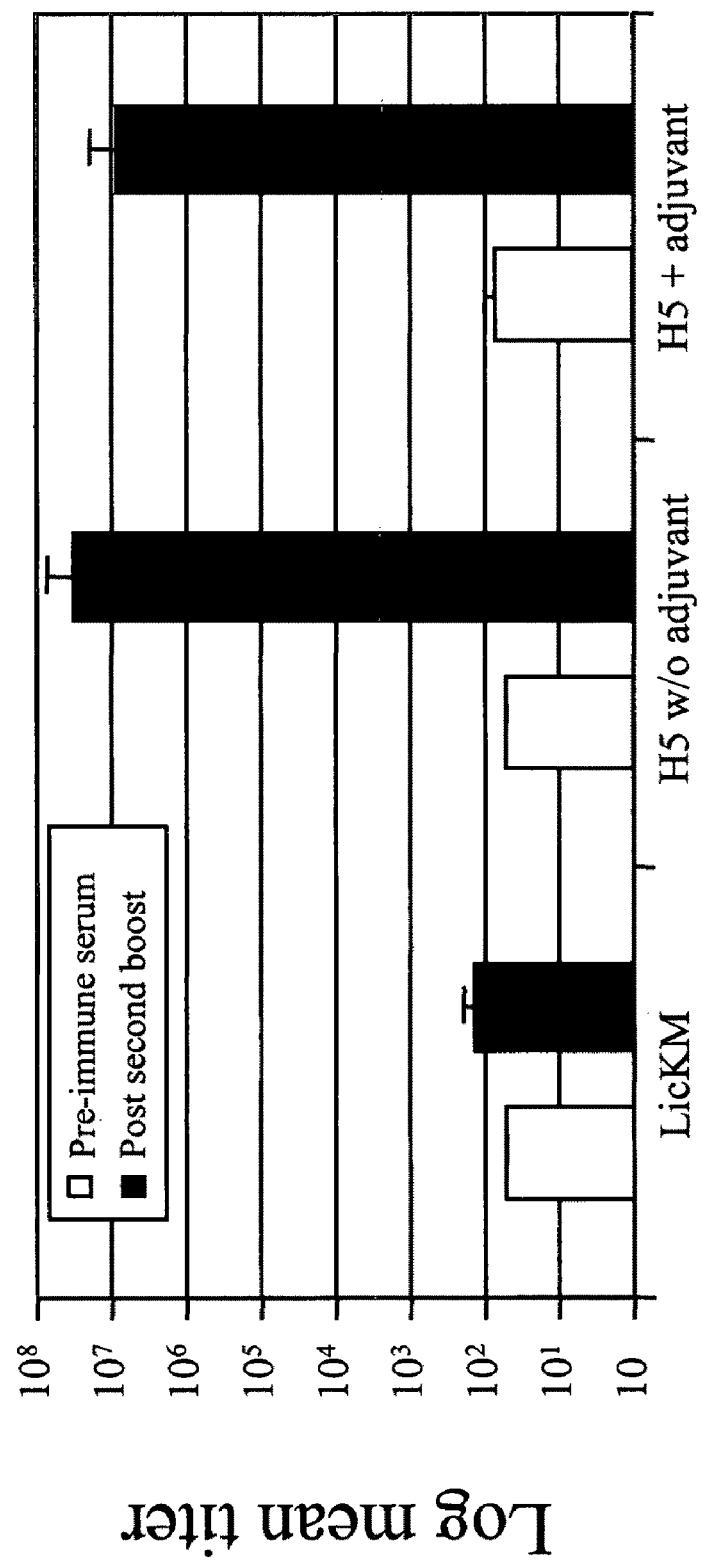

Eight-week old female BALB/c mice were immunized with 100 μg per dose of recombinant LicKM-HA(SD), LicK-MHA(GD), and 50 μg per dose of recombinant NA. Three immunizations of immunogen were administered intraperitoneally at day 1, the first boost 14 days later, followed by a second boost 10 days later. The first dose included complete Freund's adjuvant at a 1:1 volume ratio, the second dose did not include any adjuvant. A negative control group received 250 μg per dose of recombinant LicKM. Three mice were in each group. Pre-immune sera were collected one day before the first dosing, and sera were subsequently collected at day 28, after the second boost. Influenza specific IgG antibody titers were determined using an ELISA assay (FIG. 12).

Figure 13:
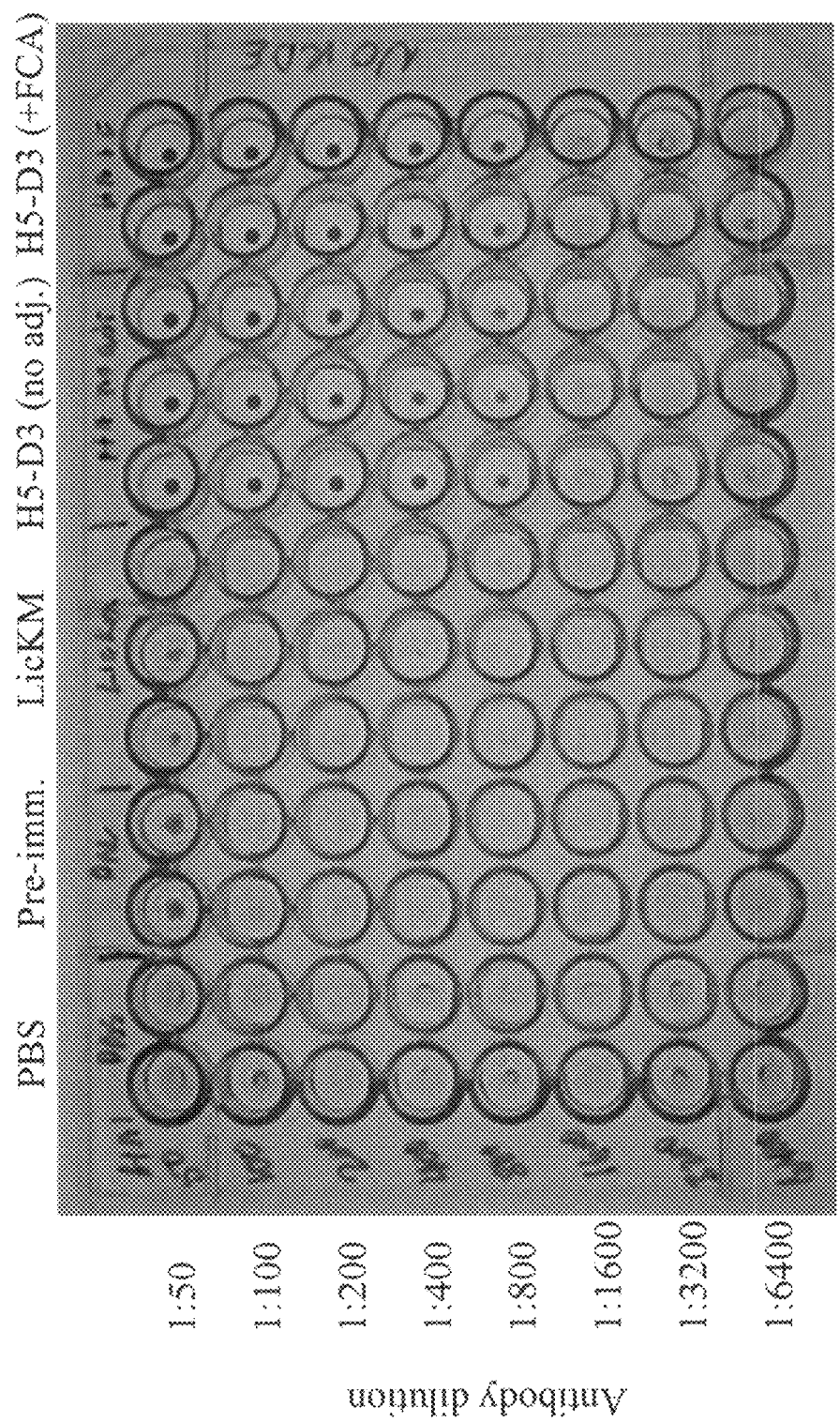

Inhibition of Hemagglutination Activity of Virus by Immune Sera Raised Against Influenza Vaccine Preimmune serum and post-second boost serum from mice immunized as described above were assessed for the ability of antibody titers to inhibit hemagglutination activity of inactivated influenza virus. 4 HA units of inactivated influenza A/Vietnam/1194/2004 virus (an H5N1 virus) was combined with 25 μl of dilutions of pre-immune serum or serum collected after the second boost of vaccine. Inhibition of hemagglutination activity in avian RBCs was assessed as described in Example 4. Resultant antibody titers were effective at inhibition of hemagglutination of virus. Exemplary results depicted in FIG. 13, and summarized in Table 1, demonstrate that antibodies raised can protect against hemagglutination activity of virus.

TABLE 1

Hemagglutination inhibition by immune sera raised against experimental influenza vaccine

| Vaccination Group | Hemagglutinin inhibition titers (serum dilution −1) |
|---|---|
| PBS control | <10 |
| PreImmune Serum | 160 |
| Vaccine w/o adjuvant | 2560 |
| Vaccine w/ adjuvant | 2560 |

Example 6

Model System of Influenza Vaccination

A. Intramuscular Vaccination

The ferret, an established animal model for the study of influenza infection, has been used to determine the efficacy of influenza vaccines (e.g. Boyd et al., 1975; Chen et al., 1995; Scheiblauer et al., 1995; Sweet et al., 1980, *Microbiol. Rev.*, 44:303; Maassab et al., 1982, *J. Infect. Dis.*, 146:780; Toms et al., 1977; Webster et al., 1994; Fenton et al., 1981; and Webster et al., 1994). Transmission studies utilizing a ferret animal model have not only demonstrated donor to recipient spread of influenza virus, but also the effects of mutations on virulence of virus (Herlocher et al., 2001; and Herlocher et al., 2002). The heterologous prime-vaccine-challenge model used in the studies described herein has been successfully tested with inactivated non adjuvanted influenza vaccines.

Production of Test Articles

We assessed the immunogenicity and protective efficacy of plant-produced antigens in ferrets. Test articles consisted of purified target antigen produced in plants. HA domains from a strain of influenza type A (A/Wyoming/3/03 [H3N2]) were engineered as fusions with thermostable carrier molecule and produced in a plant-based expression system as described above. NA from a the same strain was produced in a plant-based expression system as described above. Test articles did not contain any nucleic acids, toxic substance, or infectious agent.

Specifically, nucleotide sequences encoding amino acids 17 to 67 plus 294 to 532 of HA, which together comprise the stem domain (Wilson et al., 1981, *Nature* 289:366), were inserted into LicKM (GenBank accession number DQ776900) to give LicKM-HA(SD). Nucleotide sequences encoding amino acids 68 to 293 of HA, comprising the globular domain (Wilson et al., supra), were similarly inserted to give LicKM-HA (GD). Sequence encoding the signal peptide of the *Nicotiana tabacum* pathogenesis-related protein PR1a (Pfitzner et al., 1987, *Nucleic Acids Res.*, 15:4449) was included at the N-terminus of the fusions. Sequences encoding the poly-histidine affinity purification tag (6xHis) and the endoplasmic reticulum retention signal (KDEL) were included at the C-terminus. The LicKM fusions were introduced into the hybrid vector pBID4 (Wilson et al., supra), which allows for viral genome transcription from the cauliflower mosaic virus 35S promotor, followed by viral replication and target sequence expression from tobacco mosaic virus (TMV) coat protein subgenomic mRNA (Shivprasad et al., 1999, *Virology*, 255:

312) and which is derived from the Agrobacterial binary plasmid pBI121 (Chen et aL, 2003, *Mol, Breed.*, 11:287), for the transient expression of targets in leaves. In addition, sequence encoding amino acids 38 to 469 of NA from the same influenza strain was introduced into pBID4, without prior fusion to LicKM. As above, the signal peptide of PR1a was included at the N-terminus and 6xHis plus KDEL were included at the C-terminus.

The engineered vectors containing influenza antigens were introduced into *Agrobacterium tumefaciens* strain GV3101 by electroporation. Suspensions of recombinant *A. tumefaciens* were introduced into *Nicotiana benthamiana* plants by innoculating leaves approximately six weeks after sowing in order to introduce target sequences into leaf tissues. Plants were grown in potting soil under 12 hour light/12 hour dark conditions at 21° C. Leaves were harvested four to seven days after inoculation, depending on the expression construct. Protein extracts were prepared by grinding leaves in a buffer comprising 50 mM sodium phosphate, pH 7.0; 100 mM sodium chloride; 10 mM sodium diethyldithiocarbamate; and 10 mM β-mercaptoethanol. Recombinant antigens were enriched by ammonium sulfate precipitation followed by immobilized metal affinity chromatography (e.g., by using 6xHis tag) and anion exchange chromatography, with dialysis after each step, to at least 80% purity.

The reactions of plant-produced antigens with reference antisera were assessed by ELISA analysis (FIG. 16A) and under denaturing conditions by immunoblotting (FIG. 16B). For ELISA, 96-well plates were coated with LicKM-HA (SD), LicKM-HA(GD), or NA purified from plants or coated with inactivated influenza A/Wyoming/3/03 virus. Coated plates were incubated with sheep antiserum raised against purified HA of A/Wyoming/3/03 virus, sheep antiserum raised against NIBRG-18 (H7N2) reasserted virus, or sheep antiserum raised against NIBRG-17 (H7N1) reasserted virus. For immunoblot analysis, 100 ng of LicKM-HA(SD), 100 ng of LicKM-HA(GD), and an amount of inactivated influenza A/Wyoming/3/03 corresponding to 100 ng of HA were separated by SDS-PAGE, transferred to polyvinylidene fluoride membrane and incubated with rabbit antiserum raised against LicKM or sheep antiserum raised against purified HA from A/Wyoming/3/03 virus. NA activity was assayed according to the standard WHO protocol WHO/CDS/CSR/NCS 2002.5 Rev.1. The inhibition of NA activity was assessed by pre-incubating plant-produced NA with sheep antiserum raised against homologous (NIBRG-18 [H7N2]) or heterologous (NIBRG-17 [H7N1]) reasserted virus prior to conducting the neuraminidase assay.

In both ELISA and immunoblot assays, LicKM-HA(SD) was more strongly recognized by the reference serum than LicKM-HA(GD), although polyclonal rabbit serum raised against LicKM recognized each fusion to a similar extent (FIG. 16B). In addition, plant-produced NA was recognized by reference polyclonal sheep serum raised against reassortant H7N2 virus (FIG. 16C), and showed enzymatic activity that was inhibited by reference serum in a strain specific manner (FIG. 16C).

Vaccination

Ferret studies were carried out under UK Home Office license as required by the UK Animal (Scientific Procedures) Act, 1986. Male fitch or albino ferrets (Highgate Farm, Highgate, England), 4.5 months old, weighing from 441 to 629 g at the initiation of the study, and maintained on high-density ferret LabDiet 5L15 (IPS Product Supplies, London, UK), were assigned to treatment groups as shown in Table 2.

TABLE 2

| Treatment Groups | | | | | |
|---|---|---|---|---|---|
| Group No. | Route of Admin-istration | Number of animals in each group | Dose | Volume | Treatment |
| 1 | SC | 8 | — | 300 μl | Negative control |
| 2 | SC | 8 | 100 μg | 300 μl | Test article 1 VC1 plus adjuvant |
| 3 | SC | 8 | 100 μg | 300 μl | Test article 2 VC2 NO adjuvant |
| 4 | SC | 8 | 100 μg | 300 μl | Test article 3 VC2 plus adjuvant |
| 5 | SC | 8 | $TCID_{50}$ recorded | 300 μl | Positive control |

* $TCID_{50}$ ("Tissue Culture Infecting Dose") = the level of dilution of a virus at which half of a series of laboratory wells contain active, growing virus.

Three groups of eight ferrets were immunized subcutaneously by priming and boosting twice (on days 0, 14, and 28) with candidate vaccine formulations (VC1 plus adjuvant, VC2, and VC2 plus adjuvant) containing combinations of plant-produced influenza antigens (Table 1). VC1 animals received 100 μg of LicKM-HA(SD) and 100 μg LicKM-GD plus 1.3 mg alum. VC2 animals received 100 μg LicKM-(SD), 100 μg LicKM-(GD), and 50 μg NA, plus 1.3 mg alum ("plus adjuvant") or plus no alum ("NO adjuvant"). 100 μg of LicKM-(SD) and 100 g of LicKM-(GD) delivered together correspond to approximately 100 μg of HA. Negative control animals received alum adjuvant alone, and positive control animals were given a single intranasal dose of influenza A/Wyoming/3/03 virus (0.5 ml at a concentration of $10^{5.5}$ $TCID_{50}$ per ml on day 0). Following immunization, animals were monitored daily for lesions or irritation, mobility, erythema and general activity.

Animals were challenged intranasally while under anaesthetic with 0.5 ml of influenza A/Wyoming/3/03 virus at a concentration of $10^{5.5}$ $TCID_{50}$ per ml ten days after the final dose. Blood samples were collected from superficial tail veins on days of vaccination, challenge, and four days post-challenge, and nasal washes were collected for four days post-challenge. Serum HI titers were determined for homologous influenza A/Wyoming/3/03 virus and heterologous influenza A/Sydney/5/97 (H3N2), A/California/7/04 (H3N2) and A/New Calcdonia/20/99 (H1N1) viruses.

Influenza vaccinations, procedures, and virus challenges were carried out according to the schedule set forth in Table 3. No adverse effects were noted in any animals receiving plant-produced vaccine candidates. Animals were implanted with transponders for individual identification and monitoring body temperature. Dosing was carried out on three separate occasions at time points detailed in the study schedule (Table 3). Test material prepared in advance was aliquoted for each dose. Test material was mixed with adjuvant immediately prior to administration.

TABLE 3

| Study Schedule. | | | | | | | | |
|---|---|---|---|---|---|---|---|---|
| | Day of study | | | | | | | |
| | −38 | −24 | −10 | 0 | 1 | 2 | 3 | 4 |
| Transponder Implantation | X | | | | | | | |
| Vaccination | X | X | X | | | | | |
| Challenge | | | | X | | | | |
| Anaesthesia | X | X | X | X | X | X | X | X |

TABLE 3-continued

Study Schedule.

| | Day of study | | | | | | | |
|---|---|---|---|---|---|---|---|---|
| | −38 | −24 | −10 | 0 | 1 | 2 | 3 | 4 |
| Body Weight | X | X | X | X | X | X | X | X |
| Temperature Daily | X | X | X | X | X | X | X | X |
| Health Score | X | X | X | X | X | X | X | X |
| Nasal Wash | | | | | X | X | X | X |
| Serum for Antibody | X | X | X | X | | | | X |
| Culling | | | | | | | | X |

Analysis

Figure 14:
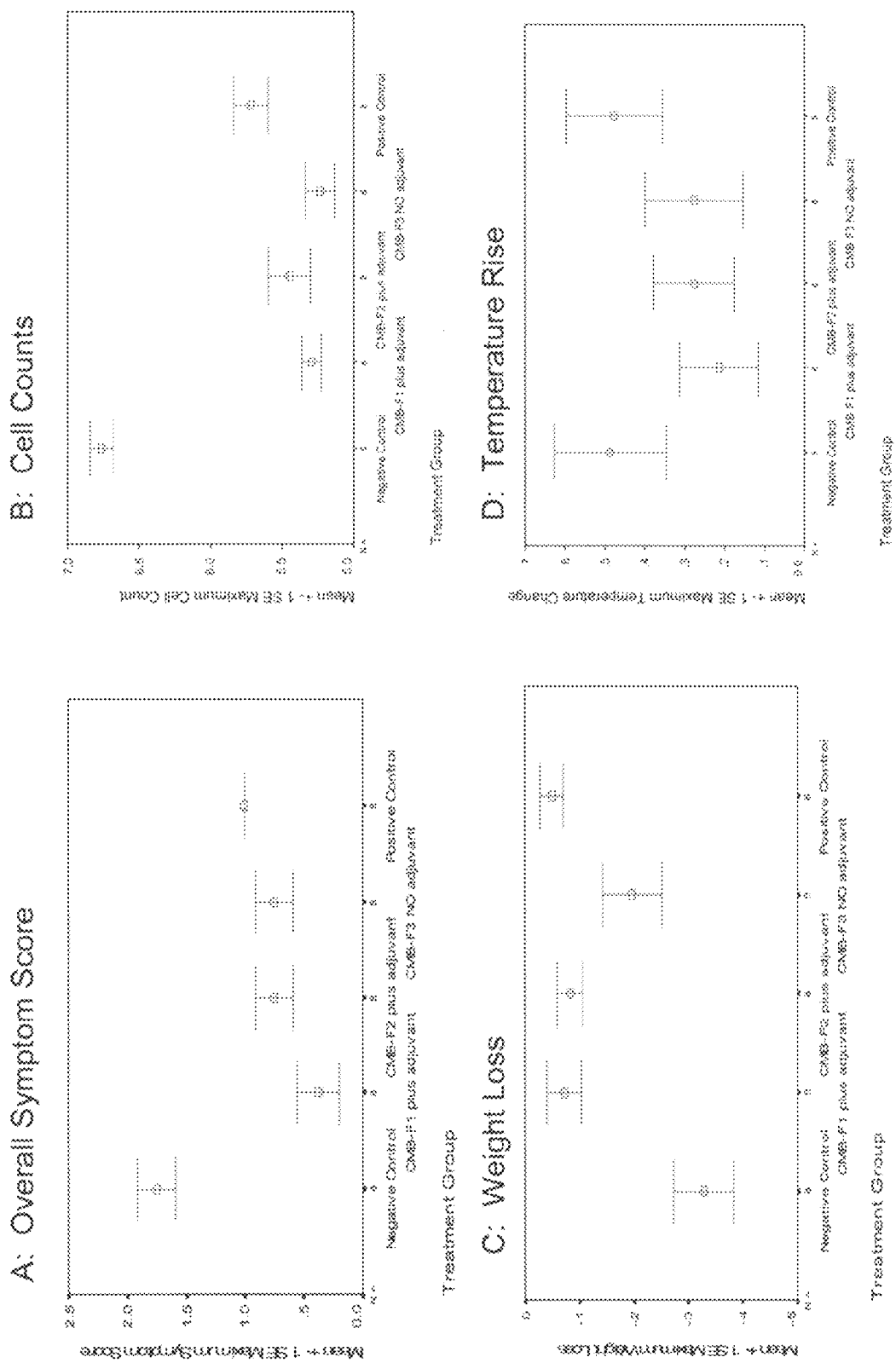

Clinical signs (health scores), body weight, and temperature changes were recorded. Once daily, post-infection, each animal examined for lesions or irritation, mobility, erythema, and general activity, and observations were recorded for determination of health scores. Each animal was scored as follows: sneezing or nasal rattling (1 point); purulent discharge from the external nares (1 point); decreased spontaneous activity or play (1 point); no spontaneous activity or decreased alertness (2 points). "Decreased spontaneous activity or play" and "no spontaneous activity or decreased alertness" were mutually exclusive scoring points. Maximum loss in weight from day of infection was calculated for each animal. Maximum increase in body temperature from day of infection was also calculated for each animal. Mean and standard deviation of maximum health score, weight loss, and temperature change for each animal on any day was calculated by treatment group and compared by ANOVA. An AUC-like measure comprising the sum health, weight loss, and temperature change scores on each day post-infection was calculated for each animal; treatment group means, medians and standard deviations were calculated and compared by ANOVA or Kruskal-Wallis test, as appropriate. Following challenge of live virus, each of the treatment groups demonstrated recovery from challenge as indicated by clinical signs, and changes in temperature and body weight. Groups of animals that received the test vaccine were protected and showed little or no symptoms of disease following challenge with homologous influenza virus. Both test vaccine candidates provided full protection to animals (FIG. 14).

Nasal washes were collected after virus challenge. The volume of nasal wash recovery was measured, and the weight of the nasal wash was monitored. The inflammatory cell response was assessed in post-challenge nasal washes by staining with Trypan blue (used to determine total cell counts) and counting leukocytes. Cell counts in nasal wash were summarized by mean, median, and Standard deviation of log-transformed data on each sampling day post-infection; treatment groups were compared by ANOVA or Kruskal-Wallis test, as appropriate. Similar to clinical signs discussed above, monitoring of nasal washes indicated treatment groups receiving each of the test treatment vaccines demonstrated protection from infection equal to, or greater than positive control groups (FIG. 14).

Viral shedding was determined using a Madin-Darby canine kidney (MDCK) cell titration on the nasal wash samples. The endpoint of the MDCK cell titration assay was determined by performing a hemagglutination assay with turkey red blood cells. The Karber calculation was used to determine $\log_{10}$ $TCID_{50}$/ml for each sample. Virus shedding from the nasal wash samples was determined on post-infection nasal wash samples. Maximum titer shed for each animal was log-transformed; treatment group means, medians, and standard deviations were calculated and compared by Kruskal-Wallis test. The proportion of animals in each treatment group with any virus shedding at any time was tabulated and the groups were contrasted using a $\chi^2$ test for independence. Results from virus shed are depicted in FIG. 15. Only the negative control treatment group resulted in significant shedding of virus (FIG. 15).

Hemagglutinin inhibition assays (HAI) were performed as described in Example 5 using pre and post-vaccination serum samples against homologous virus (Influenza A/Wyoming/3/2003 (H3N2) virus) to confirm sero-negativity of the animals at baseline and whether or not animals sero-convert following immunization and infection. HAI titres were tabulated and animals with a ≧4-fold rise between day 0 and the terminal day were identified.

Hemagglutination-inhibition (HI) activity of sera from immunized animals is regarded as a correlate of protection (Brown et al., 2004, *Dev. Biol.* (*Basel*), 115:1; and Hobson et al., 1972, *J. Hyg.*, 70:767). Results from one such experiment are presented in Table 4. All animals in groups immunized with test vaccines against H3N2 or positive control mounted strong target-specific immune responses with high serum hemagglutination inhibiting activity. Following a first dose of vaccine, VC2 plus adjuvant generated high HAI titers. VC2 without adjuvant generated a protective response, though titers not as high as with adjuvant after a first dose. However, following a second dose, titers reached similar levels to CMB1 with adjuvant. VC1 plus adjuvant also resulted in generation of protective levels of antibody which were significantly higher following a second dose of vaccine (Table 4).

TABLE 4

Ferret HAI Data Summary

| | Hemagglutinin inhibition titers (serum dilution −1) | | |
|---|---|---|---|
| Vaccination Group | pre-Imm | Dose 1 (D1) | Dose2 (D2) |
| N/controle | 5 | 5 | 5 |
| VC2 + A | 5 | 1280 | 1280 |
| VC1 + A | 5 | 50 | 1826 |
| VC2 no A | 5 | 322 | 1440 |
| P/controle | 5 | 3000 | 1367 |

Results from a second HA assay experiment are presented in FIG. 17. No HI activity was observed in pre-immune sera from any animal, or in sera from NC animals (FIG. 17). However, sera from all ferrets vaccinated with VC2 plus adjuvant exhibited high HI titers in the range of 1:320 to 1:2560 (mean titer 1273) following the first dose (FIG. 17). Fewer responders and lower HI titers following the first dose were observed among animals that received VC1 plus adjuvant (FIG. 17), suggesting that NA might have modulated the immune response. Five of the eight animals that received VC2 gave HI titers in the range of 1:160 to 1:1280, whereas commercial inactivated influenza vaccines in the absence of adjuvant typically induce very low, if any, HI titers (Potter et al., 1972, *Br. J. Exp. Pathol.,* 53:168; Potter et al., 1973, *J. Hyg. (Lond.),* 71:97; and Potter et al., 1973, *Arch. Gesamte Virusforsch.,* 42:285). Following the second dose of VC1 plus adjuvant, VC2, or VC2 plus adjuvant, sera from all ferrets had HI titers in the range of 1:640 to 1:2560, and these remained similarly high after the third dose (FIG. 17). Sera from all of these animals had titers in excess of 1:40, regarded by some as the minimum HI titer consistent with protection in humans (Brown et al., 2004, *Dev. Biol. (Basel),* 115:1; and Hobson et al., 1972, *J. Hyg.,* 70:767).

HI titers in sera from ferrets receiving two or three doses of any of the plant-produced vaccine candidates were equivalent to or greater than those in sera from intranasally infected positive control animals (FIG. 17), and were in excess of those observed in other ferret studies. For example, ferrets immunized intramuscularly with a commercial, inactivated H3N2 influenza vaccine were reported to develop HI titers of 1:20 after receiving two doses (Lambkin et al., 2004, *Vaccine,* 22:4390). Sera from ferrets immunized with VC1 plus adjuvant, VC2, or VC2 plus adjuvant had HI titers four to twenty-fold lower against the heterologous H3N2 virus strains A/Sydney/5/97 and A/California/7/04 than against A/Wyoming/3/03, but these titers were all in excess of the 1:40 threshold consistent with protection, suggesting the potential for these vaccine candidates to protect against heterologous H3N2 strains. HI titers below 1:10 were observed against influenza A/New Calcdonia/20/99 (H1N1), indicating the H3 subtype specificity of the HI antibody response.

A follow-up immunogenicity and protective efficacy study was conducted to assess the protective efficacy of plant-produced HA and NA antigens in immunized ferrets by intranasal challenge with live egg-grown influenza A/Wyoming/3/03 virus.

The extent of viral infection following challenge was determined for each animal by monitoring the titer of virus shed in nasal washes for four days post-challenge. Only one animal that received any of the three candidate vaccine formulations showed detectable virus shedding, and even then at less than $10^2$ $TCID_{50}$, whereas animals in the NC group showed virus shedding in the range of $10^6$ to $10^7$ $TCID_{50}$ (FIG. 18A). The level of virus shedding in the PC group was in the range of $10^2$ to $10^3$ $TCID_{50}$, greater than that for any animal in the candidate vaccine groups (FIG. 18A).

Evidence of protection was observed for animals receiving any of the candidate vaccine formulations. Weight loss post-infection was greatly reduced in ferrets that received VC1 plus adjuvant, VC2 plus adjuvant, or the homologous virus, compared to those in the NC group (FIG. 18B). The reduction in weight loss for animals that received VC2 was less striking (FIG. 18B). In addition, the rise in body temperature in ferrets immunized with any of the candidate vaccine formulations was reduced compared to that observed for animals in either the NC or PC groups (FIG. 18C). Furthermore, the mean peak of symptom scores, an index indicating the frequency of several influenza related symptoms following challenge, was reduced in animals that received the candidate vaccine formulations compared to those in the NC group (FIG. 18D). Similarly, counts of leukocytes in nasal washes of ferrets, taken as an indicator of upper respiratory tract infection, were reduced in candidate vaccine recipients compared to animals in the NC group (FIG. 18E).

The challenge study indicates that the plant-produced HA and NA antigens confer a high degree of protective immunity in ferrets, showing promise for vaccine development. In future studies we will elucidate the protective role of LicKM-SD and LicKM-GD when administered individually, and the role of NA in further facilitating immune responses.

B. Intranasal Vaccination

Immunogenicity of candidate vaccines is evaluated following intranasal immunization in Balb/c mice or ferret model animals. The study design is similar to that of intramuscular immunization discussed in the Examples above. In brief, groups of mice or ferrets (approximately 8-10 animals/group) are immunized intranasally with three doses (100 µg/dose) of target antigen on about days 0, 14 and 28, in the presence or absence of adjuvant (e.g., aluminum hydroxide, MALP-2, etc.). Serum samples and nasal washes are collected on each vaccination day before administering the antigen and ten days after the third dose. Immunized animals are challenged after the last dose by the nasal route with the homologous strain of influenza virus known to infect the animals and to produce symptoms of respiratory infection with fever. The nature of the immune response is examined by determining level of virus shedding, weight loss post-infection, rise in body temperature, mean peak of symptom scores, and counts of leukocytes in nasal washes, as measured after virus challenge. The presence of antibodies to NA and/or HA, as well as HI and virus neutralization activity, is examined.

C. Dose Escalation Studies

Optimum composition and doses of antigens and adjuvant, route of administration, as well as immunization regimens may be further assessed using dose escalation studies. We anticipate testing three of six test vaccine compositions in this study. The study is performed using both the intramuscular route (Table 3) and intranasal route. Similar to that of intramuscular and intranasal immunization discussed in the Examples above, groups of animals (approximately 8-10 animals/group) are immunized intranasally with various doses of test vaccine, in the presence or absence of adjuvant (e.g., aluminum hydroxide, MALP-2, etc.). See Table 5 for an exemplary dosing schedule.

As in other studies, serum samples and nasal washes are collected on each vaccination day before administering the antigen and ten days after the third dose. Immunized animals are challenged after the last dose by the nasal route with the homologous strain of influenza virus known to infect animals and to produce symptoms of respiratory infection with fever. The nature of the immune response can be determined by examining level of virus shedding; weight loss post-infection; rise in body temperature; mean peak of symptom scores; counts of leukocytes in nasal washes; presence of antibodies to NA, HA, and/or M2; hemagglutination inhibition; and/or virus neutralization activity.

TABLE 5

Exemplary Design for Dose Escalation Study in Animals.

| Group | Vaccine Candidate Composition # | Route of Vaccination | Number of Animals | Number of Doses | µg VC per Dose |
|---|---|---|---|---|---|
| 1 | Standard | i.m.* | 8 | | |
| 2 | 1 | i.m. | 8 | 3 | 10 |
| 3 | 1 | i.m. | 8 | 2 | 50 |
| 4 | 1 | i.m. | 8 | 1 | 100 |
| 5 | LicKM | i.m. | 8 | 2 | 100 |
| 6 | 2 | i.m. | 8 | 3 | 10 |
| 7 | 2 | i.m. | 8 | 2 | 50 |
| 8 | 2 | i.m. | 8 | 1 | 100 |
| 9 | 3 | i.m. | 8 | 3 | 10 |
| 10 | 3 | i.m. | 8 | 2 | 50 |
| 11 | 3 | i.m. | 8 | 1 | 100 |

*i.m. = intramuscular injection

What is claimed is:

1. An isolated antigen comprising a component of an influenza A integral membrane protein fused to a lichenase protein;
    wherein the integral membrane protein component comprises at least one immunogenic portion selected from the group consisting of an immunogenic portion of hemagglutinin (HA), an immunogenic portion of neuraminidase (NA) and an immunogenic portion of M2; and wherein the lichenase protein is a LicKM protein having the amino acid sequence of SEQ ID NO:30 or SEQ ID NO:32.

2. An immunogenic composition comprising an antigen comprising a component of an influenza A integral membrane protein fused to a lichenase protein and a pharmaceutically acceptable carrier;

wherein the integral membrane protein component comprises at least one immunogenic portion selected from the group consisting of an immunogenic portion of hemagglutinin (HA), an immunogenic portion of neuraminidase (NA) and an immunogenic portion of M2;

wherein the lichenase protein is a LicKM protein having the amino acid sequence of SEQ ID NO:30 or SEQ ID NO:32; and wherein the composition is capable of eliciting an immune response upon administration to a subject.

3. An immunogenic composition comprising at least two antigens and a pharmaceutically acceptable carrier, wherein each of the antigens comprises a component of an influenza A integral membrane protein fused to a lichenase protein, wherein the integral membrane protein component comprises at least one immunogenic portion selected from the group consisting of an immunogenic portion of hemagglutinin (HA), an immunogenic portion of neuraminidase (NA) and an immunogenic portion of M2;

wherein the lichenase protein is a LicKM protein having the amino acid sequence of SEQ ID NO:30 or SEQ ID NO:32; and wherein the composition is capable of eliciting an immune response upon administration to a subject.

4. The immunogenic composition of claim 3, wherein at least one of the integral membrane protein components comprises at least one immunogenic portion of hemagglutinin (HA), wherein the immunogenic portion is selected from the group consisting of SEQ ID NO:1, SEQ ID NO:3, SEQ ID NO:7, SEQ ID NO:8, SEQ ID NO:33, SEQ ID NO:11, SEQ ID NO:12, SEQ ID NO:13, SEQ ID NO:20 and SEQ ID NO:24.

5. The immunogenic composition of claim 3, wherein at least one of the integral membrane protein components comprises at least one immunogenic portion of neuraminidase (NA), wherein the immunogenic portion is selected from the group consisting of SEQ ID NO:2, SEQ ID NO:4, SEQ ID NO:16, and SEQ ID NO:18.

6. The immunogenic composition of claim 3, wherein at least one of the integral membrane protein components consists of full length hemagglutinin (HA) selected from SEQ ID NO:1 and SEQ ID NO:3.

7. The immunogenic composition of claim 3, wherein at least one of the integral membrane protein components consists of full length neuraminidase (NA) selected from SEQ ID NO:2 and SEQ ID NO:4.

8. The immunogenic composition of claim 3, wherein the LicKM protein comprises the amino acid sequence set forth in SEQ ID NO:30.

9. The immunogenic composition of claim 3, wherein the LicKM protein comprises the amino acid sequence set forth in SEQ ID NO:32.

10. The immunogenic composition of claim 2, wherein the integral membrane protein component is fused to LicKM at the LicKM N-terminus or at the LicKM C-terminus or is fused to a surface loop of LicKM.

11. The immunogenic composition of claim 3, wherein the integral membrane protein component comprises at least two immunogenic portions selected from the group consisting of SEQ ID NO:1, SEQ ID NO:3, SEQ ID NO:7, SEQ ID NO:8, SEQ ID NO:33, SEQ ID NO:11, SEQ ID NO:12, SEQ ID NO:13, SEQ ID NO:20, SEQ ID NO:24, SEQ ID NO:2, SEQ ID NO:4, SEQ ID NO:16, and SEQ ID NO:18, and wherein the composition is capable of eliciting an immune response upon administration to a subject.

12. The immunogenic composition of claim 11, wherein the integral membrane protein component comprises an immunogenic portion of hemagglutinin (HA) and an immunogenic portion of neuraminidase (NA).

13. The immunogenic composition of claim 11, wherein the integral membrane protein component comprises full length hemagglutinin (HA) and full length neuraminidase (NA).

14. The immunogenic composition of claim 3, further comprising a third antigen, wherein the composition is capable of eliciting an immune response upon administration to an animal.

15. The immunogenic composition of claim 14, wherein the third antigen comprises a component of influenza A integral membrane protein fused to a lichenase protein;
wherein the integral membrane protein component of the first antigen comprises at least one immunogenic portion selected from the group consisting of an immunogenic portion of hemagglutinin (HA), an immunogenic portion of neuraminidase (NA) and an immunogenic portion of M2, and the integral membrane protein component of the second antigen comprises at least one immunogenic portion distinct from the first antigen selected from the group consisting of an immunogenic portion of hemagglutinin (HA), an immunogenic portion of neuraminidase (NA) and an immunogenic portion of M2; and
wherein the composition is capable of eliciting an immune response upon administration to a subject.

16. The immunogenic composition of claim 3 wherein the antigen is produced in a plant selected from a transgenic plant and a plant transiently expressing the antigen.

17. The immunogenic composition of claim 3 wherein the composition comprises antigen which is purified, partially purified, or unpurified from plant cells, a plant, seeds, fruit, or an extract thereof.

18. The immunogenic composition of claim 3, further comprising at least one adjuvant.

19. The immunogenic composition of claim 18 wherein the adjuvant is selected from the group consisting of alum, MF59, saponin, and MALP2.

20. A method for inducing an immune response against influenza A infection in a subject comprising administering to a subject an effective amount of an anti-influenza A immunogenic composition, wherein the administration is sufficient to stimulate production of antigen specific antibodies or stimulate a cellular immune response by the subject; thereby inducing an immune response;
wherein the immunogenic composition comprises an antigen comprising a component of an influenza A integral membrane protein fused to a lichenase protein, wherein the lichenase protein is a LicKM protein having the amino acid sequence of SEQ ID NO:30 or SEQ ID NO:32; and
wherein the integral membrane protein component comprises at least one immunogenic portion selected from the group consisting of an immunogenic portion of hemagglutinin (HA), an immunogenic portion of neuraminidase (NA) and an immunogenic portion of M2.

21. A method for producing an antigen protein comprising a component of an influenza A integral membrane protein fused to a lichenase protein, comprising:
(a) preparing a nucleic acid construct encoding an antigen comprising a component of an influenza A integral membrane protein fused to a lichenase protein;
(b) introducing the nucleic acid of step (a) into a cell; and
(c) incubating the cell under conditions favorable for expression of the antigen protein; thereby producing the antigen protein;
wherein the integral membrane protein component comprises at least one immunogenic portion selected from the group consisting of an immunogenic portion of hemagglutinin (HA) and an immunogenic portion of neuraminidase (NA), and wherein the lichenase protein is a LicKM protein having the amino acid sequence of SEQ ID NO:30 or SEQ ID NO:32.

22. An isolated nucleic acid construct comprising nucleic acid sequence encoding a component of an influenza A integral membrane protein fused to a lichenase protein; wherein the lichenase protein is a LicKM protein having the amino acid sequence of SEQ ID NO:30 or SEQ ID NO:32; and wherein the integral membrane protein component comprises at least one immunogenic portion selected from the group consisting of an immunogenic portion of hemagglutinin (HA) and an immunogenic portion of neuraminidase (NA).

23. An isolated host cell comprising the nucleic acid construct of claim 22.

24. The immunogenic composition of claim 18 wherein the adjuvant comprises a mixture of QS-21, and 3 de-O-acylated monophosphoryl lipid A (3D-MPL).

25. The immunogenic composition of claim 3, wherein the integral membrane protein component is fused to LicKM at the LicKM N-terminus or at the LicKM C-terminus or is fused to a surface loop of LicKM.

* * * * *

UNITED STATES PATENT AND TRADEMARK OFFICE
CERTIFICATE OF CORRECTION

| | |
|---|---|
| PATENT NO. | : 8,124,103 B2 |
| APPLICATION NO. | : 11/706573 |
| DATED | : February 28, 2012 |
| INVENTOR(S) | : Vidadi Yusibov |

Page 1 of 1

It is certified that error appears in the above-identified patent and that said Letters Patent is hereby corrected as shown below:

Title page, Column 2 (other publications), line 1, please delete "Heaith" and insert --Health--, therefor.

Title page, Column 2 (other publications), line 1, please delete "Globai" and insert --Global--, therefor.

Column 1, line 10, please delete "'139" and insert --'378--, therefor.

Signed and Sealed this
Twenty-ninth Day of May, 2012

David J. Kappos
*Director of the United States Patent and Trademark Office*

SEQUENCE LISTING

<160> NUMBER OF SEQ ID NOS: 33

<210> SEQ ID NO 1
<211> LENGTH: 577
<212> TYPE: PRT
<213> ORGANISM: Influenza

<400> SEQUENCE: 1

```
Ala Lys Ala Gly Val Gln Ser Val Lys Met Glu Lys Ile Val Leu Leu
 1               5                  10                  15

Phe Ala Ile Val Ser Leu Val Lys Ser Asp Gln Ile Cys Ile Gly Tyr
            20                  25                  30

His Ala Asn Asn Ser Thr Glu Gln Val Asp Thr Ile Met Glu Lys Asn
        35                  40                  45

Val Thr Val Thr His Ala Gln Asp Ile Leu Glu Lys Thr His Asn Gly
    50                  55                  60

Lys Leu Cys Asp Leu Asp Gly Val Lys Pro Leu Ile Leu Arg Asp Cys
65                  70                  75                  80

Ser Val Ala Gly Trp Leu Leu Gly Asn Pro Met Cys Asp Glu Phe Ile
                85                  90                  95

Asn Val Pro Glu Trp Ser Tyr Ile Val Glu Lys Ala Asn Pro Val Asn
            100                 105                 110

Asp Leu Cys Tyr Pro Gly Asp Phe Asn Asp Tyr Glu Glu Leu Lys His
        115                 120                 125

Leu Leu Ser Arg Ile Asn His Phe Glu Lys Ile Gln Ile Ile Pro Lys
    130                 135                 140

Ser Ser Trp Ser Ser His Glu Ala Ser Leu Gly Val Ser Ser Ala Cys
145                 150                 155                 160

Pro Tyr Gln Gly Lys Ser Ser Phe Phe Arg Asn Val Val Trp Leu Ile
                165                 170                 175

Lys Lys Asn Ser Thr Tyr Pro Thr Ile Lys Arg Ser Tyr Asn Asn Thr
            180                 185                 190

Asn Gln Glu Asp Leu Leu Val Leu Trp Gly Ile His His Pro Asn Asp
        195                 200                 205

Ala Ala Glu Gln Thr Lys Leu Tyr Gln Asn Pro Thr Thr Tyr Ile Ser
    210                 215                 220

Val Gly Thr Ser Thr Leu Asn Gln Arg Leu Val Pro Arg Ile Ala Thr
225                 230                 235                 240

Arg Ser Lys Val Asn Gly Gln Ser Gly Arg Met Glu Phe Phe Trp Thr
                245                 250                 255

Ile Leu Lys Pro Asn Asp Ala Ile Asn Phe Glu Ser Asn Gly Asn Phe
            260                 265                 270

Ile Ala Pro Glu Tyr Ala Tyr Lys Ile Val Lys Lys Gly Asp Ser Thr
        275                 280                 285

Ile Met Lys Ser Glu Leu Glu Tyr Gly Asn Cys Asn Thr Lys Cys Gln
    290                 295                 300

Thr Pro Met Gly Ala Ile Asn Ser Ser Met Pro Phe His Asn Ile His
305                 310                 315                 320

Pro Leu Thr Ile Gly Glu Cys Pro Lys Tyr Val Lys Ser Asn Arg Leu
                325                 330                 335

Val Leu Ala Thr Gly Leu Arg Asn Ser Pro Gln Arg Glu Arg Arg Arg
            340                 345                 350

Lys Lys Arg Gly Leu Phe Gly Ala Ile Ala Gly Phe Ile Glu Gly Gly
        355                 360                 365
```

```
Trp Gln Gly Met Val Asp Gly Trp Tyr Gly Tyr His His Ser Asn Glu
    370                 375                 380

Gln Gly Ser Gly Tyr Ala Ala Asp Lys Glu Ser Thr Gln Lys Ala Ile
385                 390                 395                 400

Asp Gly Val Thr Asn Lys Val Asn Ser Ile Ile Asp Lys Met Asn Thr
                405                 410                 415

Gln Phe Glu Ala Val Gly Arg Glu Phe Asn Asn Leu Glu Arg Arg Ile
            420                 425                 430

Glu Asn Leu Asn Lys Lys Met Glu Asp Gly Phe Leu Asp Val Trp Thr
        435                 440                 445

Tyr Asn Ala Glu Leu Leu Val Leu Met Glu Asn Glu Arg Thr Leu Asp
    450                 455                 460

Phe His Asp Ser Asn Val Lys Asn Leu Tyr Asp Lys Val Arg Leu Gln
465                 470                 475                 480

Leu Arg Asp Asn Ala Lys Glu Leu Gly Asn Gly Cys Phe Glu Phe Tyr
                485                 490                 495

His Lys Cys Asp Asn Glu Cys Met Glu Ser Val Arg Asn Gly Thr Tyr
            500                 505                 510

Asp Tyr Pro Gln Tyr Ser Glu Glu Ala Arg Leu Lys Arg Glu Glu Ile
        515                 520                 525

Ser Gly Val Lys Leu Glu Ser Ile Gly Ile Tyr Gln Ile Leu Ser Ile
    530                 535                 540

Tyr Ser Thr Val Ala Ser Ser Leu Ala Leu Ala Leu Met Val Ala Gly
545                 550                 555                 560

Leu Ser Leu Trp Met Cys Ser Asn Gly Ser Leu Gln Cys Arg Ile Cys
                565                 570                 575

Ile

<210> SEQ ID NO 2
<211> LENGTH: 449
<212> TYPE: PRT
<213> ORGANISM: Influenza

<400> SEQUENCE: 2

Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Leu Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160
```

```
Ala Ser Ala Cys His Asp Gly Thr Ser Trp Leu Thr Ile Gly Ile Ser
            165                 170                 175

Gly Pro Asp Asn Gly Ala Val Ala Val Leu Lys Tyr Asn Gly Ile Ile
        180                 185                 190

Thr Asp Thr Ile Lys Ser Trp Arg Asn Asn Ile Leu Arg Thr Gln Glu
    195                 200                 205

Ser Glu Cys Ala Cys Val Asn Gly Ser Cys Phe Thr Val Met Thr Asp
210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Gly Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Gly Trp Ser Trp Pro Asp Gly Ala Glu Leu Pro Phe Thr Ile Asp
        435                 440                 445

Lys

<210> SEQ ID NO 3
<211> LENGTH: 566
<212> TYPE: PRT
<213> ORGANISM: Influenza

<400> SEQUENCE: 3

Met Lys Thr Ile Ile Ala Leu Ser Tyr Ile Leu Cys Leu Val Phe Ser
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80
```

```
Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Tyr Arg Pro Arg Val Arg
225                 230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510
```

```
Asn Asn Arg Phe Gln Ile Lys Gly Val Glu Leu Lys Ser Gly Tyr Lys
    515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 4
<211> LENGTH: 469
<212> TYPE: PRT
<213> ORGANISM: Influenza

<400> SEQUENCE: 4

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Val Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320
```

```
Leu Val Gly Asp Thr Pro Arg Lys Asn Asp Ser Ser Ser Ser His
            325                 330                 335

Cys Leu Asp Pro Asn Asn Glu Glu Gly His Gly Val Lys Gly Trp
        340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Glu Gly Trp Ser
        370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 5
<211> LENGTH: 22
<212> TYPE: PRT
<213> ORGANISM: Influenza

<400> SEQUENCE: 5

Leu Thr Glu Val Glu Thr Pro Ile Arg Asn Glu Trp Gly Cys Arg Cys
1               5                   10                  15

Asn Asp Ser Ser Asp Pro
            20

<210> SEQ ID NO 6
<211> LENGTH: 25
<212> TYPE: PRT
<213> ORGANISM: Influenza

<400> SEQUENCE: 6

Ala Lys Ala Gly Val Gln Ser Val Lys Met Glu Lys Ile Val Leu Leu
1               5                   10                  15

Phe Ala Ile Val Ser Leu Val Lys Ser
            20                  25

<210> SEQ ID NO 7
<211> LENGTH: 41
<212> TYPE: PRT
<213> ORGANISM: Influenza

<400> SEQUENCE: 7

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu
        35                  40

<210> SEQ ID NO 8
<211> LENGTH: 242
<212> TYPE: PRT
<213> ORGANISM: Influenza
```

```
<400> SEQUENCE: 8

Asn Thr Lys Cys Gln Thr Pro Met Gly Ala Ile Asn Ser Ser Met Pro
 1               5                  10                  15

Phe His Asn Ile His Pro Leu Thr Ile Gly Glu Cys Pro Lys Tyr Val
             20                  25                  30

Lys Ser Asn Arg Leu Val Leu Ala Thr Gly Leu Arg Asn Ser Pro Gln
         35                  40                  45

Arg Glu Arg Arg Arg Lys Lys Arg Gly Leu Phe Gly Ala Ile Ala Gly
     50                  55                  60

Phe Ile Glu Gly Gly Trp Gln Gly Met Val Asp Gly Trp Tyr Gly Tyr
 65                  70                  75                  80

His His Ser Asn Glu Gln Gly Ser Gly Tyr Ala Ala Asp Lys Glu Ser
                 85                  90                  95

Thr Gln Lys Ala Ile Asp Gly Val Thr Asn Lys Val Asn Ser Ile Ile
            100                 105                 110

Asp Lys Met Asn Thr Gln Phe Glu Ala Val Gly Arg Glu Phe Asn Asn
        115                 120                 125

Leu Glu Arg Arg Ile Glu Asn Leu Asn Lys Lys Met Glu Asp Gly Phe
    130                 135                 140

Leu Asp Val Trp Thr Tyr Asn Ala Glu Leu Leu Val Leu Met Glu Asn
145                 150                 155                 160

Glu Arg Thr Leu Asp Phe His Asp Ser Asn Val Lys Asn Leu Tyr Asp
                165                 170                 175

Lys Val Arg Leu Gln Leu Arg Asp Asn Ala Lys Glu Leu Gly Asn Gly
            180                 185                 190

Cys Phe Glu Phe Tyr His Lys Cys Asp Asn Glu Cys Met Glu Ser Val
        195                 200                 205

Arg Asn Gly Thr Tyr Asp Tyr Pro Gln Tyr Ser Glu Glu Ala Arg Leu
    210                 215                 220

Lys Arg Glu Glu Ile Ser Gly Val Lys Leu Glu Ser Ile Gly Ile Tyr
225                 230                 235                 240

Gln Ile

<210> SEQ ID NO 9
<211> LENGTH: 36
<212> TYPE: PRT
<213> ORGANISM: Influenza

<400> SEQUENCE: 9

Leu Ser Ile Tyr Ser Thr Val Ala Ser Ser Leu Ala Leu Ala Leu Met
 1               5                  10                  15

Val Ala Gly Leu Ser Leu Trp Met Cys Ser Asn Gly Ser Leu Gln Cys
             20                  25                  30

Arg Ile Cys Ile
         35

<210> SEQ ID NO 10
<211> LENGTH: 36
<212> TYPE: PRT
<213> ORGANISM: Influenza
```

-continued

```
<400> SEQUENCE: 10

Leu Ser Ile Tyr Ser Thr Val Ala Ser Ser Leu Ala Leu Ala Leu Met
 1               5                  10                  15

Val Ala Gly Leu Ser Leu Trp Met Cys Ser Asn Gly Ser Leu Gln Cys
             20                  25                  30

Arg Ile Cys Ile
         35

<210> SEQ ID NO 11
<211> LENGTH: 51
<212> TYPE: PRT
<213> ORGANISM: Influenza

<400> SEQUENCE: 11

Gln Lys Leu Pro Gly Asn Asp Asn Ser Thr Ala Thr Leu Cys Leu Gly
 1               5                  10                  15

His His Ala Val Pro Asn Gly Thr Ile Val Lys Thr Ile Thr Asn Asp
             20                  25                  30

Gln Ile Glu Val Thr Asn Ala Thr Glu Leu Val Gln Ser Ser Ser Thr
         35                  40                  45

Gly Gly Ile
     50

<210> SEQ ID NO 12
<211> LENGTH: 226
<212> TYPE: PRT
<213> ORGANISM: Influenza

<400> SEQUENCE: 12

Cys Asp Ser Pro His Gln Ile Leu Asp Gly Glu Asn Cys Thr Leu Ile
 1               5                  10                  15

Asp Ala Leu Leu Gly Asp Pro Gln Cys Asp Gly Phe Gln Asn Lys Lys
             20                  25                  30

Trp Asp Leu Phe Val Glu Arg Ser Lys Ala Tyr Ser Asn Cys Tyr Pro
         35                  40                  45

Tyr Asp Val Pro Asp Tyr Ala Ser Leu Arg Ser Leu Val Ala Ser Ser
     50                  55                  60

Gly Thr Leu Glu Phe Asn Asn Glu Ser Phe Asn Trp Ala Gly Val Thr
65                  70                  75                  80

Gln Asn Gly Thr Ser Ser Ala Cys Lys Arg Arg Ser Asn Lys Ser Phe
             85                  90                  95

Phe Ser Arg Leu Asn Trp Leu Thr His Leu Lys Tyr Lys Tyr Pro Ala
         100                 105                 110

Leu Asn Val Thr Met Pro Asn Asn Glu Lys Phe Asp Lys Leu Tyr Ile
     115                 120                 125

Trp Gly Val His His Pro Val Thr Asp Ser Asp Gln Ile Ser Leu Tyr
 130                 135                 140

Ala Gln Ala Ser Gly Arg Ile Thr Val Ser Thr Lys Arg Ser Gln Gln
145                 150                 155                 160

Thr Val Ile Pro Asn Ile Gly Tyr Arg Pro Arg Val Arg Asp Ile Ser
             165                 170                 175

Ser Arg Ile Ser Ile Tyr Trp Thr Ile Val Lys Pro Gly Asp Ile Leu
         180                 185                 190

Leu Ile Asn Ser Thr Gly Asn Leu Ile Ala Pro Arg Gly Tyr Phe Lys
     195                 200                 205
```

```
Ile Arg Ser Gly Lys Ser Ser Ile Met Arg Ser Asp Ala Pro Ile Gly
    210                 215                 220

Lys Cys
225
```

<210> SEQ ID NO 13
<211> LENGTH: 239
<212> TYPE: PRT
<213> ORGANISM: Influenza

<400> SEQUENCE: 13

```
Asn Ser Glu Cys Ile Thr Pro Asn Gly Ser Ile Pro Asn Asp Lys Pro
  1               5                  10                  15

Phe Gln Asn Val Asn Arg Ile Thr Tyr Gly Ala Cys Pro Arg Tyr Val
             20                  25                  30

Lys Gln Asn Thr Leu Lys Leu Ala Thr Gly Met Arg Asn Val Pro Glu
         35                  40                  45

Lys Gln Thr Arg Gly Ile Phe Gly Ala Ile Ala Gly Phe Ile Glu Asn
     50                  55                  60

Gly Trp Glu Gly Met Val Asp Gly Trp Tyr Gly Phe Arg His Gln Asn
 65                  70                  75                  80

Ser Glu Gly Thr Gly Gln Ala Ala Asp Leu Lys Ser Thr Gln Ala Ala
                 85                  90                  95

Ile Asn Gln Ile Asn Gly Lys Leu Asn Arg Leu Ile Gly Lys Thr Asn
            100                 105                 110

Glu Lys Phe His Gln Ile Glu Lys Glu Phe Ser Glu Val Glu Gly Arg
        115                 120                 125

Ile Gln Asp Leu Glu Lys Tyr Val Glu Asp Thr Lys Ile Asp Leu Trp
    130                 135                 140

Ser Tyr Asn Ala Glu Leu Leu Val Ala Leu Glu Asn Gln His Thr Ile
145                 150                 155                 160

Asp Leu Thr Asp Ser Glu Met Asn Lys Leu Phe Glu Arg Thr Lys Lys
                165                 170                 175

Gln Leu Arg Glu Asn Ala Glu Asp Met Gly Asn Gly Cys Phe Lys Ile
            180                 185                 190

Tyr His Lys Cys Asp Asn Ala Cys Ile Glu Ser Ile Arg Asn Gly Thr
        195                 200                 205

Tyr Asp His Asp Val Tyr Arg Asp Glu Ala Leu Asn Asn Arg Phe Gln
    210                 215                 220

Ile Lys Gly Val Glu Leu Lys Ser Gly Tyr Lys Asp Trp Ile Leu
225                 230                 235
```

<210> SEQ ID NO 14
<211> LENGTH: 34
<212> TYPE: PRT
<213> ORGANISM: Influenza

<400> SEQUENCE: 14

```
Trp Ile Ser Phe Ala Ile Ser Cys Phe Leu Leu Cys Val Ala Leu Leu
  1               5                  10                  15

Gly Phe Ile Met Trp Ala Cys Gln Lys Gly Asn Ile Arg Cys Asn Ile
             20                  25                  30

Cys Ile
```

<210> SEQ ID NO 15
<211> LENGTH: 21
<212> TYPE: PRT
<213> ORGANISM: Influenza

```
<400> SEQUENCE: 15

Met Asn Pro Asn Gln Lys Ile Ile Thr Ile Gly Ser Ile Cys Met Val
1               5                   10                  15

Thr Gly Ile Val Ser
            20

<210> SEQ ID NO 16
<211> LENGTH: 428
<212> TYPE: PRT
<213> ORGANISM: Influenza

<400> SEQUENCE: 16

Leu Met Leu Gln Ile Gly Asn Met Ile Ser Ile Trp Val Ser His Ser
1               5                   10                  15

Ile His Thr Gly Asn Gln His Gln Ser Glu Pro Ile Ser Asn Thr Asn
            20                  25                  30

Leu Leu Thr Glu Lys Ala Val Ala Ser Val Lys Leu Ala Gly Asn Ser
        35                  40                  45

Ser Leu Cys Pro Ile Asn Gly Trp Ala Val Tyr Ser Lys Asp Asn Ser
    50                  55                  60

Ile Arg Ile Gly Ser Lys Gly Asp Val Phe Val Ile Arg Glu Pro Phe
65                  70                  75                  80

Ile Ser Cys Ser His Leu Glu Cys Arg Thr Phe Phe Leu Thr Gln Gly
                85                  90                  95

Ala Leu Leu Asn Asp Lys His Ser Asn Gly Thr Val Lys Asp Arg Ser
            100                 105                 110

Pro His Arg Thr Leu Met Ser Cys Pro Val Gly Glu Ala Pro Ser Pro
        115                 120                 125

Tyr Asn Ser Arg Phe Glu Ser Val Ala Trp Ser Ala Ser Ala Cys His
    130                 135                 140

Asp Gly Thr Ser Trp Leu Thr Ile Gly Ile Ser Gly Pro Asp Asn Gly
145                 150                 155                 160

Ala Val Ala Val Leu Lys Tyr Asn Gly Ile Ile Thr Asp Thr Ile Lys
                165                 170                 175

Ser Trp Arg Asn Asn Ile Leu Arg Thr Gln Glu Ser Glu Cys Ala Cys
            180                 185                 190

Val Asn Gly Ser Cys Phe Thr Val Met Thr Asp Gly Pro Ser Asn Gly
        195                 200                 205

Gln Ala Ser His Lys Ile Phe Lys Met Glu Lys Gly Lys Val Val Lys
    210                 215                 220

Ser Val Glu Leu Asp Ala Pro Asn Tyr His Tyr Glu Glu Cys Ser Cys
225                 230                 235                 240

Tyr Pro Asp Ala Gly Glu Ile Thr Cys Val Cys Arg Asp Asn Trp His
                245                 250                 255

Gly Ser Asn Arg Pro Trp Val Ser Phe Asn Gln Asn Leu Glu Tyr Gln
            260                 265                 270

Ile Gly Tyr Ile Cys Ser Gly Val Phe Gly Asp Asn Pro Arg Pro Asn
        275                 280                 285

Asp Gly Thr Gly Ser Cys Gly Pro Val Ser Ser Asn Gly Ala Gly Gly
    290                 295                 300

Val Lys Gly Phe Ser Phe Lys Tyr Gly Asn Gly Val Trp Ile Gly Arg
305                 310                 315                 320

Thr Lys Ser Thr Asn Ser Arg Ser Gly Phe Glu Met Ile Trp Asp Pro
                325                 330                 335
```

```
Asn Gly Trp Thr Glu Thr Asp Ser Ser Phe Ser Val Lys Gln Asp Ile
            340                 345                 350

Val Ala Ile Thr Asp Trp Ser Gly Tyr Ser Gly Ser Phe Val Gln His
        355                 360                 365

Pro Glu Leu Thr Gly Leu Asp Cys Ile Arg Pro Cys Phe Trp Val Glu
    370                 375                 380

Leu Ile Arg Gly Arg Pro Lys Glu Ser Thr Ile Trp Thr Ser Gly Ser
385                 390                 395                 400

Ser Ile Ser Phe Cys Gly Val Asn Ser Asp Thr Val Gly Trp Ser Trp
                405                 410                 415

Pro Asp Gly Ala Glu Leu Pro Phe Thr Ile Asp Lys
            420                 425

<210> SEQ ID NO 17
<211> LENGTH: 37
<212> TYPE: PRT
<213> ORGANISM: Influenza

<400> SEQUENCE: 17

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe
        35

<210> SEQ ID NO 18
<211> LENGTH: 432
<212> TYPE: PRT
<213> ORGANISM: Influenza

<400> SEQUENCE: 18

Lys Gln Tyr Glu Phe Asn Ser Pro Pro Asn Asn Gln Val Met Leu Cys
1               5                   10                  15

Glu Pro Thr Ile Ile Glu Arg Asn Ile Thr Glu Ile Val Tyr Leu Thr
            20                  25                  30

Asn Thr Thr Ile Glu Lys Glu Ile Cys Pro Lys Leu Ala Glu Tyr Arg
        35                  40                  45

Asn Trp Ser Lys Pro Gln Cys Asn Ile Thr Gly Phe Ala Pro Phe Ser
    50                  55                  60

Lys Asp Asn Ser Ile Arg Leu Ser Ala Gly Gly Asp Ile Trp Val Thr
65                  70                  75                  80

Arg Glu Pro Tyr Val Ser Cys Asp Pro Asp Lys Cys Tyr Gln Phe Ala
                85                  90                  95

Leu Gly Gln Gly Thr Thr Leu Asn Asn Val His Ser Asn Asp Thr Val
            100                 105                 110

His Asp Arg Thr Pro Tyr Arg Thr Leu Leu Met Asn Glu Leu Gly Val
        115                 120                 125

Pro Phe His Leu Gly Thr Lys Gln Val Cys Ile Ala Trp Ser Ser Ser
    130                 135                 140

Ser Cys His Asp Gly Lys Ala Trp Leu His Val Cys Val Thr Gly Asp
145                 150                 155                 160

Asp Glu Asn Ala Thr Ala Ser Phe Ile Tyr Asn Gly Arg Leu Val Asp
                165                 170                 175

Ser Ile Val Ser Trp Ser Lys Lys Ile Leu Arg Thr Gln Glu Ser Glu
            180                 185                 190
```

```
Cys Val Cys Ile Asn Gly Thr Cys Thr Val Val Met Thr Asp Gly Ser
        195                 200                 205

Ala Ser Gly Lys Ala Asp Thr Lys Ile Leu Phe Ile Glu Glu Gly Lys
        210                 215                 220

Ile Val His Thr Ser Thr Leu Ser Gly Ser Ala Gln His Val Glu Glu
225                 230                 235                 240

Cys Ser Cys Tyr Pro Arg Tyr Pro Gly Val Arg Cys Val Cys Arg Asp
            245                 250                 255

Asn Trp Lys Gly Ser Asn Arg Pro Ile Val Asp Ile Asn Ile Lys Asp
        260                 265                 270

Tyr Ser Ile Val Ser Ser Tyr Val Cys Ser Gly Leu Val Gly Asp Thr
            275                 280                 285

Pro Arg Lys Asn Asp Ser Ser Ser Ser His Cys Leu Asp Pro Asn
        290                 295                 300

Asn Glu Glu Gly Gly His Gly Val Lys Gly Trp Ala Phe Asp Asp Gly
305                 310                 315                 320

Asn Asp Val Trp Met Gly Arg Thr Ile Ser Glu Lys Leu Arg Ser Gly
                325                 330                 335

Tyr Glu Thr Phe Lys Val Ile Glu Gly Trp Ser Asn Pro Asn Ser Lys
            340                 345                 350

Leu Gln Ile Asn Arg Gln Val Ile Val Asp Arg Gly Asn Arg Ser Gly
        355                 360                 365

Tyr Ser Gly Ile Phe Ser Val Glu Gly Lys Ser Cys Ile Asn Arg Cys
370                 375                 380

Phe Tyr Val Glu Leu Ile Arg Gly Arg Lys Gln Glu Thr Glu Val Leu
385                 390                 395                 400

Trp Thr Ser Asn Ser Ile Val Val Phe Cys Gly Thr Ser Gly Thr Tyr
                405                 410                 415

Gly Thr Gly Ser Trp Pro Asp Gly Ala Asp Ile Asn Leu Met Pro Ile
            420                 425                 430

<210> SEQ ID NO 19
<211> LENGTH: 870
<212> TYPE: DNA
<213> ORGANISM: Influenza

<400> SEQUENCE: 19
agatctgatc aaatctgcat tggataccac gctaacaact ctactgagca agtggataca      60
attatggaga agaacgtgac tgttactcac gctcaggata ttcttgaaaa gactcacaac     120
ggaaagttgg aggaggaaa cactaagtgc cagactccaa tgggagctat taactcttct     180
atgccattcc acaacattca cccacttact attggagagt gcccaaagta cgtgaagtct     240
aacaggcttg tgcttgctac tggacttagg aattctccac aaagagagag gagaaggaag     300 aagagggac ttttcggagc tattgctgga ttcattgagg aggatggcaa ggaatggtt      360 gatggatggt acggatacca tcactctaat gagcagggat ctggatatgc tgctgataag     420
gagtctactc agaaggctat tgatggagtg actaacaagg tgaactctat tattgataag     480
atgaacactc agttcgaagc tgttggaagg agttcaaca atcttgagag gaggattgag      540
aaccttaaca gaaaatgga ggatggattc cttgatgtgt ggacttacaa cgctgagctt     600
cttgtgctta tggagaacga gaggactctt gatttccacg attctaacgt gaagaacctt     660
tacgacaaag tgaggcttca gcttagggat aacgctaagg agcttggaaa cggttgcttc     720
gagttctacc acaagtgcga taatgagtgc atggagtctg ttaggaacgg aacttacgat     780
```

```
tacccacagt actctgagga agctagactt aagagggagg agatttctgg agtgaagttg    840
gagtctattg gtatctacca gattaagctt                                      870
```

<210> SEQ ID NO 20
<211> LENGTH: 283
<212> TYPE: PRT
<213> ORGANISM: Influenza

<400> SEQUENCE: 20

```
Asp Gln Ile Cys Ile Gly Tyr His Ala Asn Asn Ser Thr Glu Gln Val
 1               5                  10                  15

Asp Thr Ile Met Glu Lys Asn Val Thr Val Thr His Ala Gln Asp Ile
            20                  25                  30

Leu Glu Lys Thr His Asn Gly Lys Leu Asn Thr Lys Cys Gln Thr Pro
        35                  40                  45

Met Gly Ala Ile Asn Ser Ser Met Pro Phe His Asn Ile His Pro Leu
    50                  55                  60

Thr Ile Gly Glu Cys Pro Lys Tyr Val Lys Ser Asn Arg Leu Val Leu
65                  70                  75                  80

Ala Thr Gly Leu Arg Asn Ser Pro Gln Arg Glu Arg Arg Lys Lys
                85                  90                  95

Arg Gly Leu Phe Gly Ala Ile Ala Gly Phe Ile Glu Gly Gly Trp Gln
            100                 105                 110

Gly Met Val Asp Gly Trp Tyr Gly Tyr His His Ser Asn Glu Gln Gly
        115                 120                 125

Ser Gly Tyr Ala Ala Asp Lys Glu Ser Thr Gln Lys Ala Ile Asp Gly
    130                 135                 140

Val Thr Asn Lys Val Asn Ser Ile Ile Asp Lys Met Asn Thr Gln Phe
145                 150                 155                 160

Glu Ala Val Gly Arg Glu Phe Asn Asn Leu Glu Arg Arg Ile Glu Asn
                165                 170                 175

Leu Asn Lys Lys Met Glu Asp Gly Phe Leu Asp Val Trp Thr Tyr Asn
            180                 185                 190

Ala Glu Leu Leu Val Leu Met Glu Asn Glu Arg Thr Leu Asp Phe His
        195                 200                 205

Asp Ser Asn Val Lys Asn Leu Tyr Asp Lys Val Arg Leu Gln Leu Arg
    210                 215                 220

Asp Asn Ala Lys Glu Leu Gly Asn Gly Cys Phe Glu Phe Tyr His Lys
225                 230                 235                 240

Cys Asp Asn Glu Cys Met Glu Ser Val Arg Asn Gly Thr Tyr Asp Tyr
                245                 250                 255

Pro Gln Tyr Ser Glu Glu Ala Arg Leu Lys Arg Glu Glu Ile Ser Gly
            260                 265                 270

Val Lys Leu Glu Ser Ile Gly Ile Tyr Gln Ile
        275                 280
```

<210> SEQ ID NO 21
<211> LENGTH: 711
<212> TYPE: DNA
<213> ORGANISM: Influenza

<400> SEQUENCE: 21

```
agatcttgcg atcttgatgg agtgaagcca cttattctta gggattgctc tgttgctgga    60
tggcttcttg gaaacccaat gtgcgatgag ttcattaacg tgccagagtg gtcttatatt   120
gtggagaagg ctaacccagt gaacgatctt tgttacccag gagatttcaa cgattacgag   180
```

```
gagcttaagc accttctttc taggattaac cacttcgaga agattcagat tattccaaag    240
tcatcttggt catctcacga ggcttctctt ggagtttctt ctgcttgccc ataccaggga    300
aagtcatctt tcttcaggaa cgttgtgtgg cttattaaga agaactctac ttacccaact    360
attaagaggt cttacaacaa cactaaccag gaggatcttc ttgtgctttg gggaattcac    420
catccaaatg atgctgctga gcagactaag ttgtaccaga acccaactac ttacatttct    480
gtgggaactt ctactcttaa ccagaggctt gtgccaagaa ttgctactag gtctaaggtg    540
aacggacaat ctggaaggat ggagttcttc tggactattc ttaagccaaa cgatgctatt    600
aacttcgagt ctaacggaaa cttcattgct ccagagtacg cttacaagat tgtgaagaag    660
ggagattcta ctattatgaa gtctgagctt gagtacggaa actgcaagct t              711

<210> SEQ ID NO 22
<211> LENGTH: 1699
<212> TYPE: DNA
<213> ORGANISM: Influenza

<400> SEQUENCE: 22
ggatccatta attaaaatgg gattcgtgct tttctctcag cttccttctt tccttcttgt     60
gtctactctt cttcttttcc ttgtgatttc tcactcttgc cgtgctgatc aaatctgcat    120
tggataccac gctaacaact ctactgagca agtggataca attatggaga gaacgtgac    180 tgttactcac gctcaggata ttcttgaaaa gactcacaac ggaaagttgt gcgatcttga    240
tggagtgaag ccacttattc ttagggattg ctctgttgct ggatggcttc ttggaaaccc    300
aatgtgcgat gagttcatta acgtgccaga gtggtcttat attgtggaga aggctaaccc    360
agttaatgat ctttgctacc caggagattt caacgattac gaggagctta agcaccttct    420
ttctaggatt aaccacttcg agaagattca gattattcca aagtcatctt ggtcatctca    480
cgaggcttct cttggagttt cttctgcttg cccataccag ggaaagtcat ctttcttcag    540
gaacgttgtg tggcttatta agaagaactc tacttaccca actattaaga ggtcttacaa    600
caacactaac caggaggatc ttcttgtgct ttggggaatt caccatccaa atgatgctgc    660
tgagcagact aagttgtacc agaacccaac tacttacatt tctgtgggaa cttctactct    720
taaccagagg cttgtgccaa gaattgctac taggtctaag gtgaacggac aatctggaag    780
gatggagttc ttctggacta ttcttaagcc aaacgatgct attaacttcg agtctaacgg    840
aaacttcatt gctccagagt acgcttacaa gattgtgaag aagggagatt ctactattat    900
gaagtctgag cttgagtacg gaaactgcaa cactaagtgc caaactccaa tgggagctat    960
taactcttct atgccattcc acaacattca cccacttact attggagagt gcccaaagta   1020
cgtgaagtct aacaggcttg tgcttgctac tggacttagg aattctccac aaagagagag   1080
gagaaggaag aagaggggac ttttcggagc tattgctgga ttcattgagg gaggatggca   1140
aggaatggtt gatggatggt acggatacca tcactctaat gagcagggat ctggatatgc   1200
tgctgataag gagtctactc agaaggctat tgatggagtg actaacaagg tgaactctat   1260
tattgataag atgaacactc agttcgaagc tgttggaagg gagttcaaca atcttgagag   1320
gaggattgag aaccttaaca gaaaatggga ggatggattc cttgatgtgt ggacttacaa   1380
cgctgagctt cttgtgttga tggagaacga gaggactctt gatttccacg attctaacgt   1440
gaagaacctt tacgacaaag tgaggctcca gcttagggat aacgctaagg agcttggaaa   1500
cggttgcttc gagttctacc acaagtgcga taatgagtgc atggagtctg ttaggaacgg   1560
aacttacgat tacccacagt actctgagga agctagactt aagagggagg agatttctgg   1620
```

```
agtgaagttg gagtctattg gtatctacca gattcaccat caccatcacc acaaggatga   1680
gctttgatga ctcgagctc                                                1699
```

<210> SEQ ID NO 23
<211> LENGTH: 891
<212> TYPE: DNA
<213> ORGANISM: Influenza

<400> SEQUENCE: 23

```
agatctcaaa agttgccagg aaacgataac tctactgcta ctctttgcct tggacatcac     60
gctgttccaa acggaactat tgtgaaaact attactaacg atcagattga ggtgacaaac    120
gctactgagc ttgttcagtc atcttctact ggaggaattg gaggaggaaa ctctgagtgc    180
attacaccta tggatctat tccaaacgat aagccattcc agaacgtgaa caggattact    240
tatggagctt gcccaagata cgtgaagcag aacactctta agttggctac tggaatgagg    300
aatgtgccag agaagcagac taggggaatt ttcggagcta ttgctggatt cattgagaat    360
ggatgggagg gaatggttga tggatggtac ggattcaggc atcagaattc tgagggaact    420
ggacaagctg ctgatcttaa gtctactcag gctgctatta accagattaa cggaaagttg    480
aacaggctta ttggaaagac taacgagaag ttccaccaga ttgagaagga gttctctgag    540
gttgagggaa ggattcagga tcttgagaag tacgtggagg atacaaagat tgatctttgg    600
tcttacaacg ctgagcttct tgttgctctt gagaaccagc acactattga tcttactgat    660
tctgagatga acaagttgtt cgagaggact aagaagcagc ttagggagaa cgctgaggat    720
atgggaaatg gatgcttcaa aatctaccac aagtgcgata cgcttgcat tgagtctatt    780 aggaacggaa cttacgatca cgatgtgtac cgtgatgagg ctcttaacaa caggttccag    840
attaagggag tggagcttaa gtctggatac aaggattgga ttcttaagct t             891
```

<210> SEQ ID NO 24
<211> LENGTH: 290
<212> TYPE: PRT
<213> ORGANISM: Influenza

<400> SEQUENCE: 24

```
Gln Lys Leu Pro Gly Asn Asp Asn Ser Thr Ala Thr Leu Cys Leu Gly
  1               5                  10                  15

His His Ala Val Pro Asn Gly Thr Ile Val Lys Thr Ile Thr Asn Asp
             20                  25                  30

Gln Ile Glu Val Thr Asn Ala Thr Glu Leu Val Gln Ser Ser Ser Thr
         35                  40                  45

Gly Gly Ile Asn Ser Glu Cys Ile Thr Pro Asn Gly Ser Ile Pro Asn
     50                  55                  60

Asp Lys Pro Phe Gln Asn Val Asn Arg Ile Thr Tyr Gly Ala Cys Pro
 65                  70                  75                  80

Arg Tyr Val Lys Gln Asn Thr Leu Lys Leu Ala Thr Gly Met Arg Asn
                 85                  90                  95

Val Pro Glu Lys Gln Thr Arg Gly Ile Phe Gly Ala Ile Ala Gly Phe
            100                 105                 110

Ile Glu Asn Gly Trp Glu Gly Met Val Asp Gly Trp Tyr Gly Phe Arg
        115                 120                 125

His Gln Asn Ser Glu Gly Thr Gly Gln Ala Ala Asp Leu Lys Ser Thr
    130                 135                 140

Gln Ala Ala Ile Asn Gln Ile Asn Gly Lys Leu Asn Arg Leu Ile Gly
145                 150                 155                 160
```

```
Lys Thr Asn Glu Lys Phe His Gln Ile Glu Lys Glu Phe Ser Glu Val
            165                 170                 175
Glu Gly Arg Ile Gln Asp Leu Glu Lys Tyr Val Glu Asp Thr Lys Ile
        180                 185                 190
Asp Leu Trp Ser Tyr Asn Ala Glu Leu Leu Val Ala Leu Glu Asn Gln
            195                 200                 205
His Thr Ile Asp Leu Thr Asp Ser Glu Met Asn Lys Leu Phe Glu Arg
    210                 215                 220
Thr Lys Lys Gln Leu Arg Glu Asn Ala Glu Asp Met Gly Asn Gly Cys
225                 230                 235                 240
Phe Lys Ile Tyr His Lys Cys Asp Asn Ala Cys Ile Glu Ser Ile Arg
                245                 250                 255
Asn Gly Thr Tyr Asp His Asp Val Tyr Arg Asp Glu Ala Leu Asn Asn
            260                 265                 270
Arg Phe Gln Ile Lys Gly Val Glu Leu Lys Ser Gly Tyr Lys Asp Trp
        275                 280                 285
Ile Leu
    290

<210> SEQ ID NO 25
<211> LENGTH: 690
<212> TYPE: DNA
<213> ORGANISM: Influenza

<400> SEQUENCE: 25
agatcttgcg attctccaca ccagattctt gatggagaga actgcactct tattgatgct     60
cttcttggag atccacagtg cgatggattc agaacaaga agtgggatct tttcgtggaa    120
aggtctaagg cttactctaa ctgctaccca tacgatgttc agattacgc ttctcttagg    180
agtcttgtgg cttcttctgg aactcttgag ttcaacaacg agtctttcaa ctgggctgga    240
gttactcaga acggaacttc ttctgcttgt aagaggaggt ctaacaagtc tttcttctct    300
aggcttaact ggcttactca ccttaagtac aagtacccag ctcttaacgt gactatgcca    360
aacaacgaga agttcgataa gttgtacatt tggggagttc accaccagt tactgattct    420
gatcagattt ctctttacgc tcaggcttct ggaaggatta ctgtgtctac taagaggtct    480
cagcagactg tgattccaaa cattggatac cgtccaagag tgagggatat ttcttctagg    540
atttctatct actggactat tgtgaagcca ggagatattc ttcttattaa ctctactgga    600
aaccttattg ctccaagggg atacttcaag attaggagtg aaagtcatc tattatgagg    660
agtgatgctc aattggaaa gtgcaagctt                                     690

<210> SEQ ID NO 26
<211> LENGTH: 1699
<212> TYPE: DNA
<213> ORGANISM: Influenza

<400> SEQUENCE: 26
ggatccatta ttaaaatgg gattcgtgct tttctctcag cttccttctt tccttcttgt      60
gtctactctt cttctttcc ttgtgatttc tcactcttgc cgtgctcaaa agttgccagg    120
aaacgataac tctactgcta ctcttttgcct tggacatcac gctgttccaa acggaactat    180
tgtgaaaact attactaacg atcagattga ggtgacaaac gctactgagc ttgttcagtc    240
atcttctact ggaggaattt gcgattctcc acaccagatt cttgatggag agaactgcac    300
tcttattgat gctcttcttg gagatccaca gtgcgatgga ttccagaaca gaagtggga    360
tcttttcgtg gaaaggtcta aggcttactc taactgctac ccatacgatg ttccagatta    420
```

```
cgcttctctt aggagtcttg tggcttcttc tggaactctt gagttcaaca acgagtcttt      480
caactgggct ggagttactc agaacggaac ttcttctgct tgtaagagga ggtctaacaa      540
gtctttcttc tctaggctta actggcttac tcaccttaag tacaagtacc cagctcttaa      600
cgtgactatg ccaaacaacg agaagttcga taagttgtac atttgggggag ttcaccaccc     660 agttactgat tctgatcaga tttctcttta cgctcaggct tctggaagga ttactgtgtc      720
tactaagagg tctcagcaga ctgtgattcc aaacattgga taccgtccaa gagtgaggga      780
tatttcttct aggatttcta tctactggac tattgtgaag ccaggagata ttcttcttat      840
taactctact ggaaacctta ttgctccaag gggatacttc aagattagga gtggaaagtc      900
atctattatg aggagtgatg ctccaattgg aaagtgcaac tctgagtgca ttactccaaa      960
cggatctatt ccaaacgata agccattcca gaacgtgaac aggattactt atggagcttg    1020
cccaagatac gtgaagcaga acactcttaa gttggctact ggaatgagga atgtgccaga    1080
gaagcagact aggggaattt tcggagctat tgctggattc attgagaatg gatgggaggg    1140
aatggttgat ggatggtacg gattcaggca ccagaattca gagggaactg gacaagctgc    1200
tgatcttaag tctactcagg ctgctattaa ccagattaac ggaaagttga acaggcttat    1260
tggaaagact aacgagaagt ccaccagatg tgagaaggag ttctctgagg ttgagggaag    1320
gattcaggat cttgagaagt acgtggagga tacaaagatt gatctttggt cttacaacgc    1380
tgagcttctt gttgctcttg agaaccagca cactattgat ttgactgatt ctgagatgaa    1440
caagttgttc gagaggacta agaagcagct aggagaaac gctgaggata tgggaaatgg    1500
atgcttcaaa atctaccaca agtgcgataa cgcttgcatt gagtctatta ggaacggaac    1560
ttacgatcac gatgtgtacc gtgatgaggc tcttaacaac aggttccaga ttaagggagt    1620
ggagcttaag tctggataca aggattggat tcttcatcat caccaccacc acaaggatga    1680
gctttgatga ctcgagctc                                                 1699
```

<210> SEQ ID NO 27
<211> LENGTH: 1446
<212> TYPE: DNA
<213> ORGANISM: Influenza

<400> SEQUENCE: 27

```
ggatccttaa ttaaaatggg attcgtgctt ttctctcagc ttccttcttt ccttcttgtg       60
tctactcttc ttcttttcct tgtgattttct cactcttgcc gtgctcaaaa tgtcgacctt     120
atgcttcaga ttgaaacat gatttctatt tgggtgtcac actctattca cactggaaac      180
cagcatcagt ctgagccaat ttctaacact aaccttttga ctgagaaggc tgtggcttct     240
gttaagttgg ctgaaactc ttctctttgc cctattaacg gatgggctgt gtactctaag     300
gataactcta ttaggattgg atctaaggga gatgtgttcg tgattaggga gccattcatt     360
tcttgctctc accttgagtg ccgtactttc ttccttactc agggtgctct tcttaacgat    420
aagcactcta acggaactgt gaaggatagg tctccacaca ggactcttat gtcttgtcca    480
gttggagaag ctccatctcc atacaactct agattcgagt ctgttgcttg gagtgcttct    540
gcttgccatg atggaacttc atggcttact attggaattt ctggaccaga taacggagct    600
gttgctgtgc ttaagtacaa cggaattatt actgatacca tcaagtcttg gaggaacaac    660
attcttagga ctcaggagtc tgagtgtgct tgcgttaacg gatcttgctt cactgtgatg    720
actgatggac catctaatgg acaggcttct cacaagattt caagatgga gaaggggaaag    780 gttgtgaagt ctgtggaact tgatgctcca aactaccatt acgaggagtg ttcttgctat    840
```

```
ccagatgctg agagagattac ttgtgtgtgc cgtgataatt ggcatggatc taacaggcca      900
tgggtgtcat tcaatcagaa ccttgagtac cagattggtt acatttgctc tggagtgttc      960
ggagataatc caaggccaaa cgatggaact ggatcttgtg gaccagtgtc atctaatgga     1020
gctggaggag tgaagggatt ctcttttcaag tacggaaacg gagtttggat tggaaggact    1080
aagtctacta actctaggag tggattcgag atgatttggg acccaaacgg atggactgag     1140
actgattctt ctttctctgt gaagcaggat attgtggcta ttactgattg gagtggatac     1200
tctggatctt tcgttcagca cccagagctt actggacttg attgcattag gccatgcttc     1260
tgggttgaac ttattagggg aaggccaaag gagtctacta tttggacttc tggatcttct     1320
atttctttct gcggagtgaa ttctgatact gtgggatggt cttggccaga tggagctgag     1380
cttccattca ctattgataa ggtcgaccat catcatcatc accacaagga tgagctttga     1440
ctcgag                                                                 1446

<210> SEQ ID NO 28
<211> LENGTH: 1458
<212> TYPE: DNA
<213> ORGANISM: Influenza

<400> SEQUENCE: 28
ggatccttaa ttaaaatggg attcgtgctt ttctctcagc ttccttcttt ccttcttgtg        60
tctactcttc ttcttttcct tgtgatttct cactcttgcc gtgctcaaaa tgtcgacaag       120
cagtacgagt tcaactctcc accaaacaac caggttatgc tttgcgagcc aactattatt       180
gagaggaaca ttactgagat tgtgtacctt actaacacta ctattgagaa ggagatttgc       240
ccaaagttgg ctgagtaccg taattggtct aagccacagt gcaacattac tggattcgct       300
ccattctcta aggataactc aattaggctt tctgctggag agatatttg ggttacaagg        360
gagccatacg tttcttgcga tccagataag tgctaccagt tcgctcttgg acaaggaact       420
actcttaaca acgtgcactc taacgatact gtgcacgata ggactccata ccgtactctt       480
ttgatgaacg agcttggagt tccattccac cttggaacta gcaagtgtg cattgcttgg        540
tcatcttcat cttgccacga tggaaaggct tggcttcatg tttgcgtgac tggagatgat       600
gagaacgcta ctgcttcttt catctacaac ggaaggcttg tggattctat tgtttcttgg       660
tctaagaaga ttcttaggac tcaggagtct gagtgtgtgt gcattaacgg aacttgcact       720
gtggttatga ctgatggatc tgcttctgga aaggctgata caaagattct tttcattgag       780
gagggaaaga ttgtgcacac ttctactctt tctggatctg ctcagcatgt tgaggagtgt       840
tcttgctacc caaggtatcc aggagttaga tgtgtgtgcc gtgataactg aagggatct         900
aacaggccaa ttgtggatat taacattaag gattactcta ttgtgtcatc ttatgtgtgc       960
tctggacttg ttggagatac tccaaggaag aacgattctt cttcatcttc acactgcctt     1020
gatccaaata cgaggaggg aggacatgga gttaagggat gggctttcga tgatggaaac       1080
gatgtttgga tgggaaggac tatttctgag aagttgagga gcggatacga gactttcaaa     1140
gtgattgagg gatggtctaa cccaaattct aagctgcaga ttaacaggca agtgattgtg     1200
gatagggaa acaggagtgg atactctgga attttctctg tggagggaaa gtcttgcatt      1260
aacagatgct tctacgtgga gcttattagg ggaaggaagc aggagactga ggttttgtgg     1320
acttctaact ctattgtggt gttctgcgga acttctggaa cttacggaac tggatcttgg     1380
ccagatggag ctgatattaa ccttatgcca attgtcgacc atcatcacca tcaccacaag      1440
gatgagcttt gactcgag                                                    1458
```

<210> SEQ ID NO 29
<211> LENGTH: 1458
<212> TYPE: DNA
<213> ORGANISM: Artificial Sequence
<220> FEATURE:
<223> OTHER INFORMATION: Synthetic DNA

<400> SEQUENCE: 29

```
ggatccttaa ttaaaatggg attcgtgctt ttctctcagc ttccttcttt ccttcttgtg      60
tctactcttc ttcttttcct tgtgatttct cactcttgcc gtgctcaaaa tgtcgacaag     120
cagtacgagt tcaactctcc accaaacaac caggttatgc tttgcgagcc aactattatt     180
gagaggaaca ttactgagat tgtgtacctt actaacacta ctattgagaa ggagatttgc     240
ccaaagttgg ctgagtaccg taattggtct aagccacagt gcaacattac tggattcgct     300
ccattctcta aggataactc aattaggctt tctgctggag agatatttg gttacaagg      360
gagccatacg tttcttgcga tccagataag tgctaccagt tcgctcttgg acaaggaact     420
actcttaaca acgtgcactc taacgatact gtgcacgata ggactccata ccgtactctt     480
ttgatgaacg agcttggagt tccattccac cttggaacta gcaagtgtg cattgcttgg      540
tcatcttcat cttgccacga tggaaaggct tggcttcatg tttgcgtgac tggagatgat     600
gagaacgcta ctgcttcttt catctacaac ggaaggcttg tggattctat tgtttcttgg     660
tctaagaaga ttcttaggac tcaggagtct gagtgtgtgt gcattaacgg aacttgcact     720
gtggttatga ctgatggatc tgcttctgga aaggctgata caaagattct tttcattgag     780
gagggaaaga ttgtgcacac ttctactctt tctggatctg ctcagcatgt tgaggagtgt     840
tcttgctacc caaggtatcc aggagttaga tgtgtgtgcc gtgataactg aagggatct      900
aacaggccaa ttgtggatat taacattaag gattactcta ttgtgtcatc ttatgtgtgc     960
tctggacttg ttggagatac tccaaggaag aacgattctt cttcatcttc acactgcctt    1020
gatccaaata cgaggaggg aggacatgga gttaagggat gggctttcga tgatggaaac    1080
gatgtttgga tgggaaggac tatttctgag aagttgagga gcggatacga gactttcaaa    1140
gtgattgagg atggtctaa cccaaattct aagctgcaga ttaacaggca agtgattgtg    1200
gataggggaa acaggagtgg atactctgga attttctctg tggagggaaa gtcttgcatt    1260
aacagatgct tctacgtgga gcttattagg ggaaggaagc aggagactga ggttttgtgg    1320
acttctaact ctattgtggt gttctgcgga acttctggaa cttacggaac tggatcttgg    1380
ccagatggag ctgatattaa ccttatgcca attgtcgacc atcatcacca tcaccacaag    1440
gatgagcttt gactcgag                                                  1458
```

<210> SEQ ID NO 30
<211> LENGTH: 230
<212> TYPE: PRT
<213> ORGANISM: Artificial Sequence
<220> FEATURE:
<223> OTHER INFORMATION: Synthetic Protein

<400> SEQUENCE: 30

```
Met Gly Gly Ser Tyr Pro Tyr Lys Ser Gly Glu Tyr Arg Thr Lys Ser
 1               5                  10                  15

Phe Phe Gly Tyr Gly Tyr Tyr Glu Val Arg Met Lys Ala Ala Lys Asn
            20                  25                  30

Val Gly Ile Val Ser Ser Phe Phe Thr Tyr Thr Gly Pro Ser Asp Asn
        35                  40                  45

Asn Pro Trp Asp Glu Ile Asp Ile Glu Phe Leu Gly Lys Asp Thr Thr
    50                  55                  60
```

```
Lys Val Gln Phe Asn Trp Tyr Lys Asn Gly Val Gly Asn Glu Tyr
 65                  70                  75                  80

Leu His Asn Leu Gly Phe Asp Ala Ser Gln Asp Phe His Thr Tyr Gly
                 85                  90                  95

Phe Glu Trp Arg Pro Asp Tyr Ile Asp Phe Tyr Val Asp Gly Lys Lys
            100                 105                 110

Val Tyr Arg Gly Thr Arg Asn Ile Pro Val Thr Pro Gly Lys Ile Met
        115                 120                 125

Met Asn Leu Trp Pro Gly Ile Gly Val Asp Glu Trp Leu Gly Arg Tyr
130                 135                 140

Asp Gly Arg Thr Pro Leu Gln Ala Glu Tyr Glu Tyr Val Lys Tyr Tyr
145                 150                 155                 160

Pro Asn Gly Arg Ser Glu Phe Lys Leu Val Val Asn Thr Pro Phe Val
                165                 170                 175

Ala Val Phe Ser Asn Phe Asp Ser Ser Gln Trp Glu Lys Ala Asp Trp
            180                 185                 190

Ala Asn Gly Ser Val Phe Asn Cys Val Trp Lys Pro Ser Gln Val Thr
        195                 200                 205

Phe Ser Asn Gly Lys Met Ile Leu Thr Leu Asp Arg Glu Tyr Val Asp
210                 215                 220

His His His His His His
225                 230

<210> SEQ ID NO 31
<211> LENGTH: 822
<212> TYPE: DNA
<213> ORGANISM: Artificial Sequence
<220> FEATURE:
<223> OTHER INFORMATION: Synthetic DNA

<400> SEQUENCE: 31
ggatccttaa ttaaaatggg atttgttctc ttttcacaat tgccttcatt tcttcttgtc      60
tctacacttc tcttattcct agtaatatcc cactcttgcc gtgcccaaaa tggaggttct     120
tatccatata gtctggtga gtatagaact aagtctttct ttggatatgg ttattatgaa     180
gttaggatga aggctgcaaa gaacgttgga attgttcttc tttctttac ttatactgga     240 ccatctgata caacccatg ggatgagatt gatattgagt ttcttggaaa ggatactact     300
aaggttcaat tcaactggta taagaatggt gttggtggaa acgagtatct tcataacctt     360
ggatttgatg cttctcaaga ttttcatact tatggttttg agtggagacc agattatatt     420 gattttatg ttgatggaaa gaaggtttat agaggtacta gaaacattcc agttactcct     480
ggaaagatta tgatgaatct ttggccagga attggtgttg atgaatggct tggtagatat     540
gatggaagaa ctccacttca agctgagtat gagtatgtta agtattatcc aaacggtaga     600
tctgaattca gcttgttgt taatactcca tttgttgctg ttttctctaa ctttgattct     660
tctcaatggg aaaaggctga ttgggctaac ggttctgttt ttaactgtgt ttggaagcca     720
tctcaagtta cttttttctaa cggaaagatg attcttactt tggatagaga gtatgtcgac     780
catcatcatc atcatcataa ggatgaactt tgactcgagc tc                         822

<210> SEQ ID NO 32
<211> LENGTH: 265
<212> TYPE: PRT
<213> ORGANISM: Artificial Sequence
<220> FEATURE:
<223> OTHER INFORMATION: Synthetic Protein
```

<400> SEQUENCE: 32

```
Met Gly Phe Val Leu Phe Ser Gln Leu Pro Ser Phe Leu Leu Val Ser
 1               5                  10                  15
Thr Leu Leu Phe Leu Val Ile Ser His Ser Cys Arg Ala Gln Asn
             20                  25                  30
Gly Gly Ser Tyr Pro Tyr Lys Ser Gly Glu Tyr Arg Thr Lys Ser Phe
             35                  40                  45
Phe Gly Tyr Gly Tyr Tyr Glu Val Arg Met Lys Ala Ala Lys Asn Val
 50                  55                  60
Gly Ile Val Ser Ser Phe Phe Thr Tyr Thr Gly Pro Ser Asp Asn Asn
 65                  70                  75                  80
Pro Trp Asp Glu Ile Asp Ile Glu Phe Leu Gly Lys Asp Thr Thr Lys
                 85                  90                  95
Val Gln Phe Asn Trp Tyr Lys Asn Gly Val Gly Asn Glu Tyr Leu
                 100                 105                 110
His Asn Leu Gly Phe Asp Ala Ser Gln Asp Phe His Thr Tyr Gly Phe
             115                 120                 125
Glu Trp Arg Pro Asp Tyr Ile Asp Phe Tyr Val Asp Gly Lys Lys Val
 130                 135                 140
Tyr Arg Gly Thr Arg Asn Ile Pro Val Thr Pro Gly Lys Ile Met Met
145                 150                 155                 160
Asn Leu Trp Pro Gly Ile Gly Val Asp Glu Trp Leu Gly Arg Tyr Asp
                 165                 170                 175
Gly Arg Thr Pro Leu Gln Ala Glu Tyr Glu Tyr Val Lys Tyr Tyr Pro
                 180                 185                 190
Asn Gly Arg Ser Glu Phe Lys Leu Val Val Asn Thr Pro Phe Val Ala
             195                 200                 205
Val Phe Ser Asn Phe Asp Ser Ser Gln Trp Glu Lys Ala Asp Trp Ala
 210                 215                 220
Asn Gly Ser Val Phe Asn Cys Val Trp Lys Pro Ser Gln Val Thr Phe
225                 230                 235                 240
Ser Asn Gly Lys Met Ile Leu Thr Leu Asp Arg Glu Tyr Val Asp His
                 245                 250                 255
His His His His Lys Asp Glu Leu
                 260                 265
```

<210> SEQ ID NO 33
<211> LENGTH: 233
<212> TYPE: PRT
<213> ORGANISM: Influenza

<400> SEQUENCE: 33

```
Cys Asp Leu Asp Gly Val Lys Pro Leu Ile Leu Arg Asp Cys Ser Val
 1               5                  10                  15
Ala Gly Trp Leu Leu Gly Asn Pro Met Cys Asp Glu Phe Ile Asn Val
             20                  25                  30
Pro Glu Trp Ser Tyr Ile Val Glu Lys Ala Asn Pro Val Asn Asp Leu
                 35                  40                  45
Cys Tyr Pro Gly Asp Phe Asn Asp Tyr Glu Glu Leu Lys His Leu Leu
 50                  55                  60
Ser Arg Ile Asn His Phe Glu Lys Ile Gln Ile Ile Pro Lys Ser Ser
 65                  70                  75                  80
Trp Ser Ser His Glu Ala Ser Leu Gly Val Ser Ser Ala Cys Pro Tyr
             85                  90                  95
```

-continued

```
Gln Gly Lys Ser Ser Phe Phe Arg Asn Val Val Trp Leu Ile Lys Lys
            100             105             110

Asn Ser Thr Tyr Pro Thr Ile Lys Arg Ser Tyr Asn Asn Thr Asn Gln
            115             120             125

Glu Asp Leu Leu Val Leu Trp Gly Ile His His Pro Asn Asp Ala Ala
            130             135             140

Glu Gln Thr Lys Leu Tyr Gln Asn Pro Thr Thr Tyr Ile Ser Val Gly
145             150             155             160

Thr Ser Thr Leu Asn Gln Arg Leu Val Pro Arg Ile Ala Thr Arg Ser
                165             170             175

Lys Val Asn Gly Gln Ser Gly Arg Met Glu Phe Phe Trp Thr Ile Leu
            180             185             190

Lys Pro Asn Asp Ala Ile Asn Phe Glu Ser Asn Gly Asn Phe Ile Ala
            195             200             205

Pro Glu Tyr Ala Tyr Lys Ile Val Lys Lys Gly Asp Ser Thr Ile Met
    210             215             220

Lys Ser Glu Leu Glu Tyr Gly Asn Cys
225             230
```